(12) United States Patent
Wabl

(10) Patent No.: US 12,049,516 B2
(45) Date of Patent: Jul. 30, 2024

(54) TRANSGENIC MAMMALS AND METHODS OF USE THEREOF

(71) Applicant: TRIANNI, INC., San Franscico, CA (US)

(72) Inventor: Matthias Wabl, San Francisco, CA (US)

(73) Assignee: TRIANNI, INC., San Francisco, CA (US)

(*) Notice: Subject to any disclaimer, the term of this patent is extended or adjusted under 35 U.S.C. 154(b) by 958 days.

(21) Appl. No.: 16/849,847

(22) Filed: Apr. 15, 2020

(65) Prior Publication Data

US 2020/0308307 A1 Oct. 1, 2020

Related U.S. Application Data

(60) Division of application No. 15/603,334, filed on May 23, 2017, now Pat. No. 10,662,256, which is a continuation-in-part of application No. 13/818,184, filed as application No. PCT/US2011/045333 on Jul. 26, 2011, now Pat. No. 10,881,084.

(60) Provisional application No. 62/340,234, filed on May 23, 2016, provisional application No. 61/367,809, filed on Jul. 26, 2010.

(51) Int. Cl.
| | | |
|---|---|---|
| C07K 16/46 | (2006.01) | |
| A01K 67/0278 | (2024.01) | |
| C07K 16/00 | (2006.01) | |
| A61K 39/00 | (2006.01) | |

(52) U.S. Cl.
CPC ........ *C07K 16/462* (2013.01); *A01K 67/0278* (2013.01); *C07K 16/00* (2013.01); *C12Y 304/24046* (2013.01); *A01K 2217/072* (2013.01); *A01K 2217/15* (2013.01); *A01K 2227/105* (2013.01); *A61K 2039/552* (2013.01); *C07K 2317/20* (2013.01); *C07K 2317/24* (2013.01); *C07K 2317/51* (2013.01); *C07K 2317/515* (2013.01); *C07K 2317/56* (2013.01)

(58) Field of Classification Search
CPC .................................................. C07K 16/462
See application file for complete search history.

(56) References Cited

U.S. PATENT DOCUMENTS

| | | |
|---|---|---|
| 4,892,824 A | 1/1990 | Skaletsky |
| 5,591,669 A | 1/1997 | Krimpenfort et al. |
| 5,593,598 A | 1/1997 | McGinness et al. |
| 5,612,205 A | 3/1997 | Kay et al. |
| 5,633,425 A | 5/1997 | Lonberg et al. |
| 5,661,016 A | 8/1997 | Lonberg et al. |
| 5,789,215 A | 8/1998 | Berns et al. |
| 5,789,650 A | 8/1998 | Lonberg et al. |
| 5,814,318 A | 9/1998 | Lonberg et al. |
| 5,874,299 A | 2/1999 | Lonberg et al. |
| 5,877,397 A | 3/1999 | Lonberg et al. |
| 5,939,598 A | 8/1999 | Kucherlapati et al. |
| 5,985,615 A | 11/1999 | Jakobovits et al. |
| 6,023,010 A | 2/2000 | Krimpenfort et al. |
| 6,091,001 A | 7/2000 | Jakobovits et al. |
| 6,114,598 A | 9/2000 | Kucherlapati et al. |
| 6,130,364 A | 10/2000 | Jakobovits et al. |
| 6,162,963 A | 12/2000 | Kucherlapati et al. |
| 6,492,575 B1 | 12/2002 | Wagner et al. |
| 6,570,061 B1 | 5/2003 | Rajewsky et al. |
| 6,586,251 B2 | 7/2003 | Economides |
| 6,596,541 B2 | 7/2003 | Murphy |
| 6,653,113 B1 | 11/2003 | Berns et al. |
| 6,673,986 B1 | 1/2004 | Kucherlapati et al. |
| 6,998,514 B2 | 2/2006 | Bruggeman |
| 7,041,870 B2 | 5/2006 | Kazuma et al. |
| 7,041,871 B1 | 5/2006 | Lonberg |
| 7,064,244 B2 | 6/2006 | Jakobovits et al. |
| 7,105,348 B2 | 9/2006 | Murphy |
| 7,129,084 B2 | 10/2006 | Buelow |
| 7,145,056 B2 | 12/2006 | Jakobovits et al. |
| 7,205,148 B2 | 4/2007 | Economides et al. |
| 7,294,754 B2 | 11/2007 | Poueymirou et al. |
| 7,473,557 B2 | 1/2009 | Economides et al. |
| 7,476,536 B2 | 1/2009 | Kuroiwa et al. |
| 7,501,552 B2 | 3/2009 | Lonberg |
| 7,541,513 B2 | 6/2009 | Bruggeman |
| 7,659,442 B2 | 2/2010 | Poueymirou et al. |
| 7,868,223 B2 | 1/2011 | Tomizuka et al. |
| 8,158,419 B2 | 4/2012 | Lonberg |
| 8,232,449 B2 | 7/2012 | Tanamachi |

(Continued)

FOREIGN PATENT DOCUMENTS

| | | |
|---|---|---|
| CA | 2089661 C | 3/1992 |
| EP | 0817835 A1 | 1/1998 |

(Continued)

OTHER PUBLICATIONS

Garcia-Arocena D. (2014, The Jackson Laboratory, Same Mutation, Different Phenotype?) (Year: 2014).*

(Continued)

*Primary Examiner* — Anoop K Singh
*Assistant Examiner* — David A Montanari
(74) *Attorney, Agent, or Firm* — MEDLER FERRO WOODHOUSE & MILLS PLLC

(57) ABSTRACT

The present invention relates to transgenic mammals that express canine-based immunoglobulins, including transgenic rodents that express canine-based immunoglobulins for the development of canine therapeutic antibodies.

5 Claims, 11 Drawing Sheets

Specification includes a Sequence Listing.

(56) References Cited

U.S. PATENT DOCUMENTS

| | | |
|---|---|---|
| 8,293,480 B2 | 10/2012 | Lonberg |
| 8,367,888 B2 | 2/2013 | Bruggeman |
| 8,502,018 B2 | 8/2013 | Murphy |
| 8,754,287 B2 | 6/2014 | MacDonald et al. |
| 9,012,717 B2 | 4/2015 | MacDonald et al. |
| 9,580,491 B2 | 2/2017 | Green et al. |
| 10,494,445 B2 | 12/2019 | Green et al. |
| 10,526,420 B2 | 1/2020 | Green et al. |
| 10,575,504 B2 | 3/2020 | Green et al. |
| 10,604,587 B2 † | 3/2020 | Green |
| 10,618,977 B2 | 4/2020 | Green et al. |
| 10,626,188 B2 | 4/2020 | Green et al. |
| 10,662,255 B2 | 5/2020 | Green et al. |
| 2003/0017534 A1 | 1/2003 | Buelow |
| 2006/0015957 A1 | 1/2006 | Lonberg |
| 2007/0061900 A1 | 3/2007 | Murphy |
| 2009/0055943 A1 | 2/2009 | Economides |
| 2009/0111126 A1 | 4/2009 | Akamatsu |
| 2009/0136950 A1 | 5/2009 | Dubridge |
| 2010/0317539 A1 | 12/2010 | Yu |
| 2011/0145937 A1 | 6/2011 | MacDonald et al. |
| 2011/0236378 A1 | 9/2011 | Green |
| 2011/0258710 A1 | 10/2011 | Murphy |
| 2011/0283376 A1 | 11/2011 | Murphy |
| 2012/0047585 A1 | 2/2012 | Rohrer et al. |
| 2012/0073004 A1 | 3/2012 | MacDonald |
| 2012/0090041 A1 | 4/2012 | Buelow |
| 2012/0096572 A1 | 4/2012 | MacDonald et al. |
| 2013/0137101 A1 | 5/2013 | Economides |
| 2013/0263292 A1 | 10/2013 | Liang |
| 2013/0333057 A1 | 12/2013 | MacDonald et al. |
| 2014/0283150 A1 | 9/2014 | Bradley et al. |
| 2014/0283153 A1 | 9/2014 | Trianni |
| 2015/0183820 A1 | 7/2015 | Honda et al. |
| 2017/0058052 A1 | 3/2017 | Wabl et al. |
| 2017/0188557 A1 | 7/2017 | Green et al. |
| 2017/0218090 A1 | 8/2017 | Green et al. |
| 2017/0226162 A1 | 8/2017 | Killeen et al. |
| 2017/0303517 A1 | 10/2017 | Wabl |
| 2018/0230238 A1 | 8/2018 | Wabl et al. |
| 2020/0181285 A1 | 6/2020 | Green et al. |
| 2020/0181286 A1 | 6/2020 | Green et al. |
| 2020/0407464 A1 † | 12/2020 | Green |

FOREIGN PATENT DOCUMENTS

| | | |
|---|---|---|
| EP | 1399559 A2 | 3/2004 |
| EP | 1399575 A2 | 3/2004 |
| EP | 2264163 A2 | 12/2010 |
| EP | 2517556 A2 | 10/2012 |
| EP | 2517557 A2 | 10/2012 |
| GB | 2398784 A | 9/2004 |
| GB | 2561352 A | 10/2018 |
| WO | 90/04036 A1 | 4/1990 |
| WO | 90/10077 A1 | 9/1990 |
| WO | 1992/03918 A1 † | 3/1992 |
| WO | 94/25585 A1 | 11/1994 |
| WO | 96/40915 A2 | 12/1996 |
| WO | 99/45962 A1 | 6/1999 |
| WO | 01/09187 A2 | 2/2001 |
| WO | 02/12437 A2 | 2/2002 |
| WO | 02/066618 A1 | 8/2002 |
| WO | 02/066630 A1 | 8/2002 |
| WO | 2008/070367 A2 | 6/2008 |
| WO | 2008/081197 A1 | 7/2008 |
| WO | 2008/151081 A1 | 12/2008 |
| WO | 2009/013620 A2 | 1/2009 |
| WO | 2009/157771 A2 | 12/2009 |
| WO | 2010/039900 A2 | 4/2010 |
| WO | 2011/004192 A1 | 1/2011 |
| WO | 2011/123708 A2 | 10/2011 |
| WO | 2011/158009 A1 | 12/2011 |
| WO | 2011/163311 A1 | 12/2011 |
| WO | 2012/018610 A2 | 2/2012 |
| WO | 2012/123949 A1 | 9/2012 |
| WO | 2013/022782 A1 | 2/2013 |
| WO | 2013/092720 A1 | 6/2013 |
| WO | 2013/096142 A1 | 6/2013 |
| WO | 2013/138681 A1 | 9/2013 |
| WO | 2013/171505 A2 | 11/2013 |
| WO | 2014/013075 A2 | 1/2014 |
| WO | 2015/112790 A2 | 7/2015 |
| WO | 2015/188141 A2 | 12/2015 |
| WO | 2017/035252 A1 | 3/2017 |
| WO | 2017/095939 A1 | 6/2017 |
| WO | 2018/128691 A1 | 7/2018 |
| WO | 2018/189520 A1 | 10/2018 |
| WO | 2019/113065 A1 | 6/2019 |
| WO | 2020/074874 A1 | 4/2020 |

OTHER PUBLICATIONS

Heimain-Patterson et al. (2011, Amyotrophic Lateral Schlerosis, vol. 00, pp. 1-8) (Year: 2011).*
2004, Barthold S., Genetica, vol. 122, pp. 75-88 (Year: 2004).*
Tong et al. (2010, Nature, vol. 467(7312), pp. 211-213) (Year: 2010).*
Hong et al. (2012, Stem Cells and Development, vol. 21(9), pp. 1571-1586) (Year: 2012).*
U.S. Appl. No. 61/361,302, filed Jul. 2, 2010 in the name of Ablexis, LLC.
U.S. Appl. No. 61/319,690, filed Mar. 31, 2010 in the name of Ablexis, LLC.
Martin, Jolyon et al., "Comprehensive annotation and evolutionary insights into the canine (*Canis lupus familiaris*) antigen receptor loci", Immunogenetics, 2018, vol. 70, pp. 223-236.
Bürckstümmer, Tilmann et al., "An Efficient tandem affinity puricification procedure for interaction proteomics in mammalian cells," Nature Methods, Dec. 2006, vol. 3, No. 12, pp. 1013-1019.
Lanitis, Evripidis et al., "Chimeric Antigen Receptor T Cells with Dissociated Signaling Domains Exhibit Focused Antitumor Activity with Reduced Potential for Toxicity In Vivo," Cancer Immunology Research, Jul. 2013, vol. 1, No. 1, pp. 43-53.
Melidoni, Anna N. et al., "Selecting antagonistic antibodies that control differentiation through inducible expression in embryonic stem cells," PNAS, Oct. 29, 2013, vol. 110, No. 44, pp. 17802-17807.
Tunyaplin, Chainarong et al., "Characterization of the B lymphocyte-induced maturation protein-1 (Blimp-1) gene, mRNA isoforms and basal promoter," Nucleic Acids Research, 2000, vol. 28, No. 24, pp. 4846-4855.
Young, Carissa L. et al., "Recombinant protein expression and purification: A comprehensive review of affinity tags and microbial applications," Biotechnology Journal, 2012, vol. 7, pp. 623-634.
Any references not provided herewith were previously cited and submitted in U.S. Appl. No. 15/603,334, filed May 23, 2017 to which this application claims priority.
Altschul et al., "Basic local alignment search tool," *J Mol Biol* 215:403-410 (1990).
Avitahl et al., "A 125 bp region of the Ig $V_H1$ promoter is sufficient to confer lymphocyte-specific expression in transgenic mice," *Int Immunol* 8(9):1359-1366 (1996).
Bao et al., "Molecular characterization of the VH repertoire in *Canis familiaris*," *Vet Immunol Immunopathol* 137:64-75 (2010).
Barthold, "Genetically altered mice: phenotypes, no phenotypes, and Faux phenotypes," *Genetica* 122: 75-88 (2004).
Bentley et al., "Unrearranged immunoglobulin variable region genes have a functional promoter," *Nucleic Acids Res* 10:1841-1856 (1982).
Berman et al., "Content and organization of the human Ig $V_H$ locus: definition of three new $V_H$ families and linkage to the Ig $C_H$ locus," *EMBO J* 7(3):727-738 (1988).
Blankenstein et al., "Immunoglobulin $V_H$ region genes of the mouse are organized in overlapping cluster," *Eur J Immunol.* 17:1351-1357 (1987).
Brekke et al., "Assembly and analysis of the mouse immunoglobulin kappa gene sequence," *Immunogenetics* 56:490-505 (2004).

(56) References Cited

OTHER PUBLICATIONS

Brevini et al., "No shortcuts to pig embryonic stem cells," *Theriogenology* 74: 544-550 (2010).
Bruggemann, "The Preparation of Human Antibodies from Mice Harbouring Human Immunoglobulin Loci," *Transgenic Animals: Generation and Use*, pp. 397-402, Ed. L.M. Houdebine, CRC Press (1997).
Buta et al., "Reconsidering pluripotency tests: Do we sill need teratoma assays?" *Stem Cell Research* 11: 552-562 (2013).
Casellas et al., "IgK allelic inclusion is a consequence of receptor editing," *J Exp Med* 204(1):153-160 (2007).
Cesari et al., "Elk-1 knock-out mice engineered by Flp recombinase-mediated cassette exchange," *Genesis* 38:87-92 (2004).
Choe et al., "Fc-Binding Ligands of Immunoglobulin G: An Overview of High Affinity Proteins and Peptides," *Materials* 9: 994 (2016).
Church et al., "Lineage-specific biology revealed by a finished genome assembly of the mouse," *PLoS Biol* 7:e1000112 (2009).
Clargo et al., "The rapid generation of recombinant functional monoclonal antibodies from individual, antigen-specific bone marrow-derived plasma cells isolated using a novel fluorescence-based method," *mAbs* 6(1): 143-159 (2013).
Clarke et al., "An immunoglobulin promoter region is unaltered by DNA rearrangement and somatic mutation during B-cell development," *Nucleic Acids Res* 10:7731-7749 (1982).
De Bono, Bernard et al., "$V_H$ Gene Segments in the Mouse and Human Genomes", J. Mol. Biol., 2004, vol. 342, pp. 131-143.
Decaire et al., "A Publicly Available PCR Methods Laboratory Manual and Supporting Material," *J Microbiol Biol Educ* 16:269-270 (2015).
Downing et al., "Technical assessment of the first 20 years of research using mouse embryonic stem cell lines," *Stem Cells* 22:1168-1180 (2004).
Doyen et al., "Analysis of promoter and enhancer cell type specificities and the regulation of immunoglobulin gene expression," *Gene* 50:321-331 (1986).
Featherstone et al., "The Mouse Immunoglobulin Heavy Chain V-D Intergenic Sequence Contains Insulators That May Regulate Ordered V(D)J Recombination," *J Biol Chem* 285:9327-9338 (2010).
Fishwild et al., "High-avidity human IgG kappa monoclonal antibodies from a novel strain of minilocus transgenic mice," *Nat Biotechnol*, 14:845-851 (1996).
Garcia-Arocena, "Same Mutation, Different Phenotype?" The Jackson Laboratory, Blog Post dated Nov. 11, 2014. Accessed at https://www.jax.org/news-and-insights/jax-blog/2014/november/same-mutation-different-phenotype.
Gellert, "Molecular analysis of V(D)J recombination," *Annu Rev Genet* 26:425-446 (1992).
Gomez et al., "Derivation of cat embryonic stem-like cells from in vitro-produced blastocytes on homologous and heterologous feeder cells," *Theriogenology* 74: 498-515 (2010).
Gopal et al., "Contribution of promoter to tissue-specific expression of the mouse immunoglobulin kappa gene," *Science* 229:1102-1104 (1985).
Gunasekaran et al., "Enhancing Antibody Fc Heterodimer Formation through Electrostatic Steering Effects," *J Biol Chem* 285:19637-19646 (2010).
Hauser, Jannek et al., "Allelic Exclusion of IgH through Inhibition of E2A in a VDJ Recombination Complex", The Journal of Immunology, vol. 192, 2014, pp. 2460-2470.
Heiman-Patterson et al., "Effect of genetic background on phenotype variability in transgenic mouse models of amyotrophic lateral sclerosis: A window of opportunity in the search for genetic modifiers," *Amyotrophic Laterla Sclerosis* 00: 1-8 (2011).
Hengartner et al., "Assignment of genes for immunoglobulin kappa and heavy chains to chromosomes 6 and 12 in mouse," *Proc Natl Acad Sci USA* 75:4494-4498 (1978).
Hong et al., "Derivation and Characterization of Embryonic Stem Cell Lines Derived from Transgenic Fischer 344 and Dark Agouti Rats," *Stem Cells and Development* 21(9): 1571-1586 (2012).

Honjo et al., ed. *Immunoglobulin Genes*. San Diego, CA: Academic Press Inc., 1989; Chapters 4-6 and 17.
Ichihara et al., "Organization of human immunoglobulin heavy chain diversity gene loci," *EMBO J* 7(13):4141-4150 (1988).
International Human Genome Sequencing Consortium, "Finishing the euchromatic sequence of the human genome," *Nature* 431:931-945 (2004).
Ivics et al., "Germline transgenesis in rodents by pronuclear microinjection of *Sleeping Beauty* transposons," *Nature Protocols* 9(4); 773-793 (2014).
Johnston et al., "Complete Sequence Assembly and Characterization of the C57BL/6 Mouse Ig Heavy Chain V Region," *J Immunol* 176:4221-4234 (2006).
Jones et al., "Replacing the complementarity-determining regions in a human antibody with those from a amouse," *Nature* 321:522-525 (1986).
Jung et al., "Unraveling V(D)J Recombination: Insights into Gene Regulation," *Cell* 116:299-311 (2004).
Kabat et al., "Variable region genes for the immunoglobulin framework are assembled from small segments of DNA—a hypothesis," *Proc Natl Acad Sci USA* 75:2429-2433 (1978).
Kabat et al., "Evidence supporting somatic assembly of the DNA segments (minigenes), coding for the framework, and complementarity-determining segments of immunoglobulin variable regions," *J Exp Med* 149:1299-1313 (1979).
Kawasaki et al., "One-Megabase Sequence Analysis of the Human Immunoglobulin λ Gene Locus," *Genome Res* 7:250-261 (1997).
Kitamura et al., "Targeted disruption of μ chain membrane exon causes loss of heavy-chain allelic exclusion," *Nature* 356:154-156 (1992).
Kontermann et al., "Bispecific antibodies," *Drug Discov Today* 20(7):838-847 (2015).
Kozak, "An analysis of 5'-noncoding sequences from 699 vertebrate messenger RNAs," *Nucleic Acids Res* 15:8125-8148 (1987).
Kurosawa et al., "Organization, Structure, and Assembly of Immunoglobulin Heavy Chain Diversity DNA Segments," *J Exp Med* 155:201-218 (1982).
Lander et al., "Initial sequencing and analysis of the human genome," *Nature* 2001, 409:860-921 (2001).
Landsteiner et al., "On the Specificity of Serological Reactions with Simple Chemical Compounds (Inhibition Reactions)," *J Exp Med* 54:295-305 (1931).
Lee et al., "Genome data mining for everyone," *BMB Reports* 41(11):757-764 (2008).
Lefranc et al., "IMGT unique numbering for immunoglobulin and T cell receptor variable domains and Ig superfamily V-like domains," *Dev Comp Immunol* 27:55-77 (2003).
Li et al., "Biochemical Analysis of the Regulatory T Cell Protein Lymphocyte Activation Gene-3 (LAG-3; CD223)," *Journal of Immunology* 173: 6806-6812 (2004).
Liu et al., "A Novel Antibody Engineering Strategy for Making Monovalent Bispecific Heterodimeric IgG Antibodies by Electrostatic Steering Mechanism," *J Biol Chem* 290:7535-7362 (2015).
Lutz et al., "Pro-B cells sense productive immunoglobulin heavy chain rearrangement irrespective of polypeptide production," *Proc Nat Acad Sci USA* 108(26):10644-10649 (2011).
Ma et al., "DNA Synthesis, Assembly and Applications in Synthetic Biology," *Curr Opin Chem Biol* 16:260-267 (2012).
Manz et al., "Analysis and sorting of live cells according to secreted molecules relocated to a cell-surface affinity matrix," *Proceedings of the National Academy of Science USA* 92: 1921-1925 (1995).
Mason et al., "Transcription cell type specificity is conferred by an immunoglobulin VH gene promoter that includes a functional consensus sequence," *Cell* 41:479-487 (1985).
Matsuda et al., "The Complete Nucleotide Sequence of the Human Immunoglobulin Heavy Chain Variable Region Locus," *J Exp Med* 188(11):2151-2162 (1998).
McLenachan et al., "Flow-cytometric analysis of mouse embryonic stem cell lipofection using small and large DNA constructs," *Genomics* 89:708-720 (2007).
Meng et al., "Optimized production of transgenic buffalo embryos and offspring by cytoplasmic zygote injection," *Journal of Animal Science and Biotechnology* 6: 44 (2015).

(56) References Cited

OTHER PUBLICATIONS

Misra et al., "Gene targeting in the mouse: advances in introduction of transgenes into the genome by homologous recombination," *Endocrine* 19:229-238 (2002).
Munoz et al., "Conventional pluripotency markers are unspecific for bovine embryonic-derived cell-lines," *Theriogenology* 69: 1159-1164 (2008).
Mouse Genome Sequencing Consortium, "Initial sequencing and comparative analysis of the mouse genome," *Nature* 420:520-562 (2002).
Paris et al., "Equine embryos and embryonic stem cells: Defining reliable markers of pluripotency," *Theriogenology* 74: 516-524 (2010).
Pinder et al., "Isolation and Characterization of Antigen-Specific Plasmablasts Using a Novel Flow Cytometry-Based Ig Capture Assay," *Journal of Immunology* 199(12): 4180-4188 (2017).
Priat et al., "A whole-genome radiation hybrid map of the dog genome," *Genomics* 54(3):361-378 (1998).
Price et al., "Engineered cell surface expression of membrane immunoglobulin as a means to identify monoclonal antibody-secreting hybridomas," *Journal of Immunological Methods* 343: 28-41 (2009).
Rajewsky et al., "Allelic exclusion model questioned," Scientific Correspondence, *Nature* 359:371-372 (1992).
Ristevski, "Making better transgenic models: conditional, temporal, and spatial approaches," *Mol Biotechnol* 29:153-163 (2005).
Roebroek et al., "Mutant Lrp1 knock-in mice generated by recombinase-mediated cassette exchange reveal differential importance of the NPXY motifs in the intracellular domain of LRP1 for normal fetal development," *Mol Cell Biol* 26:605-616 (2006).
Saiki et al., "Analysis of enzymatically amplified beta-globin and HLA-DQ alpha DNA with allele-specific oligonucleotide probes," *Nature* 324:163-166 (1986).
Sakano et al., "Identification and nucleotide sequence of a diversity DNA segment (D) of immunoglobulin heavy-chain genes," *Nature* 290:562-565 (1981).
Schellenberg et al., "Pre-mRNA splicing: a complex picture in higher definition," *Trends Biochem Sci* 33:243-246 (2008).
Sharon, "The invariant tryptophan in an H chain V region is not essential to antibody binding," *J Immunol* 140:2666-2669 (1988).
Sonoda et al., "B Cell Development under the Condition of Allelic Inclusion," *Immunity* 6:225-233 (1997).
Tonegawa, "Somatic generation of antibody diversity," *Nature* 302:575-581 (1983).
Tong et al., "Production of p53 gene knockout rats by homologous recombination in embryonic stem cells," *Nature* 467: 211-215 (2010).
Toor et al., "Structural insights into RNA splicing," *Curr Opin Struct Biol* 19:260-266 (2009).
Venter et al., "The sequence of the human genome," *Science* 291:1304-1351 (2001).
Vetterman et al., "Allelic exclusion of immunoglobulin genes: models and mechanisms," *Immunol Rev* 237:22-42 (2010).
Van Keuren et al., "Generating Transgenic Mice from Bacterial Artificial Chromosomes: Transgenesis Efficiency, Integration and Expression Outcomes," *Transgenic Research* 18(5): 769-785 (2009).
Verkoczy, Laurent et al., "Human Ig knockin mice to study the development and regulation of HIV-1 broadly neutralizing antibodies", Immunological Reviews, 2017, vol. 275, pp. 89-107.
Von Heijne, "Protein targeting signals," *Curr Opin Cell Biol* 2:604-608 (1990).
Wabl et al., "Allelic exclusion model questioned," Scientific Correspondence, *Nature* 359:370-371 (1992).
Wallace, Helen A.C. et al., "Manipulating the Mouse Genome to Engineer Precise Functional Syntenic Replacements with Human Sequence", Cell, Jan. 12, 2007, vol. 128, pp. 197-209.
Waisman, Ari et al., IgG1 B cell receptor signaling is inhibited by CD22 and promotes the development of B cells whose survival is less dependent on Igα/β.
Wang, Feng et al., "Reshaping Antibody Diversity", Cell, Jun. 6, 2013, vol. 153, No. 6, pp. 1379-1393.
West et al., "Genome Editing in Large Animals," *Journal of Equine Veterinary Science* 41: 1-6 (2014).
Xiong et al., "Chemical gene synthesis: strategies, softwares, error corrections, and applications," *FEMS Microbiol Rev* 32:522-540 (2008).
Zhang, Shaosen et al., "A New and Robust Method of Tethering IgG Surrogate Antigens on Lipid Bilayer Membranes to Facilitate the TIRFM Based Live Cell and Single Molecule Imaging Experiments", PloS ONE, May 2013, vol. 8, No. 5, pp. 1-14.
Zhou, Hongzhe et al., "Generation of Monoclonal Antibodies against Highly Conserved Antigens", PloS ONE, Jun. 2009, vol. 4, No. 6, pp. 1-6.
Final Office Action in co-pending U.S. Appl. No. 13/818,184, dated Jun. 1, 2018.
Non-Final Office Action issued in U.S. Appl. No. 13/818,184, dated Mar. 8, 2019.
Non-final Office Action issued in U.S. Appl. No. 15/603,347, dated Jun. 28, 2019.
Dale A. Ramsden et al., Conservation of sequence in recombination signal sequence spacers, pp. 1785-1796, Pub. Apr. 13, 1994, Oxford University Press.†
Charlotte Proudhon et al., Long range regulation of V(D)J recombination, pp. 1-60, Pub. Jul. 3, 2015, Department of Health & Human Services, United States.†
USPTO, Non-Final Office Action issued against U.S. Appl. No. 15/603,334, pp. cover & 1-17, Aug. 22, 2019, USPTO.†
Yonghua Bao et al., Molecular characterization of the VH repertoire in Canis Familiaris, pp. 64-75, Pub. Apr. 16, 2010, Elsevier B. V.†
Trianni, Inc., Amendment Reply under 37 C.F.R. § 1.111 submitted in response to Office Action mailed regarding U.S. Appl. No. 15/603,334, pp. 1-9, Sep. 19, 2019.†
Wabl and Killeen, Response to Accompany Request for Continued Examination relating to U.S. Appl. No. 13/818,184, pp. 1-22, Jul. 10, 2017.†

\* cited by examiner
† cited by third party

TRANSGENIC MAMMALS AND METHODS OF USE THEREOF

FIELD OF THE INVENTION

This invention relates to production of immunoglobulin molecules, including methods for generating transgenic mammals capable of producing canine antigen-specific antibody-secreting cells for the generation of monoclonal antibodies.

BACKGROUND OF THE INVENTION

In the following discussion certain articles and methods are described for background and introductory purposes. Nothing contained herein is to be construed as an "admission" of prior art. Applicant expressly reserves the right to demonstrate, where appropriate, that the articles and methods referenced herein do not constitute prior art under the applicable statutory provisions.

Antibodies have emerged as important biological pharmaceuticals because they (i) exhibit exquisite binding properties that can target antigens of diverse molecular forms, (ii) are physiological molecules with desirable pharmacokinetics that make them well tolerated in treated humans and animals, and (iii) are associated with powerful immunological properties that naturally ward off infectious agents. Furthermore, established technologies exist for the rapid isolation of antibodies from laboratory animals, which can readily mount a specific antibody response against virtually any foreign substance not present natively in the body.

In their most elemental form, antibodies are composed of two identical heavy (H) chains that are each paired with an identical light (L) chain. The N-termini of both H and L chains consist of a variable domain ($V_H$ and $V_L$, respectively) that together provide the paired H-L chains with a unique antigen-binding specificity. The exons that encode the antibody $V_H$ and $V_L$ domains do not exist in the germline DNA. Instead, each $V_H$ exon is generated by the recombination of randomly selected V, D, and J gene segments present in the H chain locus (Igh; see schematic of the mouse Igh locus in FIG. 1); likewise, individual $V_L$ exons are produced by the chromosomal rearrangements of randomly selected V and J gene segments in a light chain locus. The canine genome contains two alleles that can express the H chain (one allele from each parent), two alleles that can express the kappa (κ) L chain, and two alleles that can express the lambda (λ) L chain. There are multiple V, D, and J gene segments at the H chain locus as well as multiple V and J gene segments at both L chain loci. Downstream of the J genes at each immunoglobulin (Ig) locus exists one or more exons that encode the constant region of the antibody. In the heavy chain locus, exons for the expression of different antibody classes (isotypes) also exist. In canine animals, the encoded isotypes are IgM, IgD, IgG1, IgG2, IgG3, IgG4, IgE, and IgA. Polymorphic variants (referred to as allotypes) also exist among canine strains for IgG2, IgE and IgA and are useful as allelic markers.

During B cell development, gene rearrangements occur first on one of the two homologous chromosomes that contain the H chain variable gene segments. The resultant $V_H$ exon is then spliced at the RNA level to the exons that encode the constant region of the H chain ($C_H$). Subsequently, the VJ rearrangements occur on one L chain allele at a time until a functional L chain is produced, after which the L chain polypeptides can associate with the H chain homodimers to form a fully functional B cell receptor for antigen (BCR).

The genes encoding various canine (e.g., the domestic dog and wolf) and mouse immunoglobulins have been extensively characterized, although the sequence and annotation of the canine Ig loci in the genome databases is not yet complete. Priat, et al., describe whole-genome radiation mapping of the dog genome in Genomics, 54:361-78 (1998), and Bao, et al., describe the molecular characterization of the $V_H$ repertoire in *Canis familiaris* in Veterinary Immunology and Immunopathology, 137:64-75 (2010). Blankenstein and Krawinkel describe the mouse variable heavy chain region in Eur. J. Immunol., 17:1351-1357 (1987). The generation of transgenic animals—such as mice having varied immunoglobulin loci—has allowed the use of such transgenic animals in various research and development applications, e.g., in drug discovery and basic research into various biological systems. For example, the generation of transgenic mice bearing human immunoglobulin genes is described in International Application WO 90/10077 and WO 90/04036. WO 90/04036 describes a transgenic mouse with an integrated human immunoglobulin "mini" locus. WO 90/10077 describes a vector containing the immunoglobulin dominant control region for use in generating transgenic animals.

Numerous methods have been developed for modifying the mouse endogenous immunoglobulin variable region gene locus with, e.g., human immunoglobulin sequences to create partly or fully-human antibodies for drug discovery purposes. Examples of such mice include those described in, e.g., U.S. Pat. Nos. 7,145,056; 7,064,244; 7,041,871; 6,673,986; 6,596,541; 6,570,061; 6,162,963; 6,130,364; 6,091,001; 6,023,010; 5,593,598; 5,877,397; 5,874,299; 5,814,318; 5,789,650; 5,661,016; 5,612,205; and 5,591,669. However, many of the fully humanized immunoglobulin transgenic mice exhibit suboptimal antibody production because B cell development in these mice is severely hampered by inefficient V(D)J recombination, and by inability of the fully human antibodies/BCRs to function optimally with mouse signaling proteins. Other humanized immunoglobulin transgenic mice, in which the mouse coding sequence have been "swapped" with human sequences, are very time consuming and expensive to create due to the approach of replacing individual mouse exons with the synthetic human counterpart.

The use of antibodies that function as drugs is not necessarily limited to the prevention or therapy of human disease. Companion animals such as dogs suffer from some of the same afflictions as humans, e.g., cancer, atopic dermatitis and chronic pain. Monoclonal antibodies targeting CD20, IgE and Nerve Growth Factor, respectively, are already in veterinary use as for treatment of these conditions. However, before clinical use these monoclonal antibodies, which were made in mice, had to be caninized, i.e., their amino acid sequence had to be changed from mouse to dog, in order to prevent an immune response in the recipient dogs. Based on the foregoing, it is clear that a need exists for efficient and cost-effective methods to produce canine antibodies for the treatment of diseases in dogs. More particularly, there is a need in the art for small, rapidly breeding, non-canine mammals capable of producing antigen-specific canine immunoglobulins. Such non-canine mammals are useful for generating hybridomas capable of large-scale production of canine monoclonal antibodies.

In accordance with the foregoing object, transgenic non-human animals are provided which are capable of producing an antibody with canine V regions.

SUMMARY OF THE INVENTION

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description including those aspects illustrated in the accompanying drawings and defined in the appended claims.

The present invention comprises a non-canine mammalian cell and a non-canine mammal having a genome comprising an exogenously introduced partly canine immunoglobulin locus, where the introduced locus comprises coding sequences of the canine immunoglobulin variable region genes and non-coding sequences based on the endogenous immunoglobulin variable region locus of the non-canine mammalian host. Thus, the non-canine mammalian cell or mammal of the invention is capable of expressing a chimeric B cell receptor (BCR) or antibody comprising H and L chain variable regions that are fully canine in conjunction with the respective constant regions that are native to the non-canine mammalian host cell or mammal. Preferably, the transgenic cells and animals of the invention have genomes in which part or all of the endogenous immunoglobulin variable region gene locus is removed.

At a minimum, the production of chimeric canine monoclonal antibodies in a non-canine mammalian host requires the host to have at least one locus that expresses chimeric canine immunoglobulin H or L chain. In most aspects, there are one heavy chain locus and two light chain loci that, respectively, express chimeric canine immunoglobulin H and L chains.

In some aspects, the partly canine immunoglobulin locus comprises canine $V_H$ coding sequences and non-coding regulatory or scaffold sequences present in the endogenous $V_H$ gene locus of the non-canine mammalian host. In these aspects, the partly canine immunoglobulin locus further comprises canine $D_H$ and $J_H$ gene segment coding sequences in conjunction with the non-coding regulatory or scaffold sequences present in the vicinity of the endogenous $D_H$ and $J_H$ gene segments of the non-canine mammalian host cell genome.

In other aspects, the partly canine immunoglobulin locus comprises canine $V_L$ coding sequences and non-coding regulatory or scaffold sequences present in the endogenous $V_L$ gene locus of the non-canine mammalian host. More preferably, the exogenously introduced, partly canine immunoglobulin locus comprising canine $V_L$ coding sequences further comprises canine L-chain J gene segment coding sequences and non-coding regulatory or scaffold sequences present in the vicinity of the endogenous L-chain J gene segments of the non-canine mammalian host cell genome.

In certain aspects, the non-canine mammal is a rodent, preferably a mouse or rat.

In one specific aspect, the invention provides a method for generating a non-canine mammalian cell comprising a partly canine immunoglobulin locus, said method comprising: a) introducing two or more recombinase targeting sites into the genome of a non-canine mammalian host cell and integrating at least one site upstream and at least one site downstream of a genomic region comprising endogenous immunoglobulin variable region genes; and b) introducing into the non-canine mammalian host cell via recombinase-mediated cassette exchange (RMCE) an engineered partly canine immunoglobulin variable gene locus comprising canine immunoglobulin variable region gene coding sequences and non-coding regulatory or scaffold sequences corresponding to the non-coding regulatory or scaffold sequences present in the endogenous immunoglobulin variable region gene locus of the non-canine mammalian host.

In another aspect, the method further comprises deleting the genomic region flanked by the two exogenously introduced recombinase targeting sites prior to step b.

In a specific aspect of this method, the exogenously introduced, engineered partly canine immunoglobulin locus comprises canine $V_H$ gene segment coding sequences, and further comprises i) canine $D_H$ and $J_H$ gene segment coding sequences and ii) non-coding regulatory or scaffold sequences upstream of the canine $D_H$ gene segments (pre-D sequences, FIG. 1) that correspond to the sequences present upstream of the endogenous $D_H$ gene segments in the genome of the non-canine mammalian host. Furthermore, these upstream scaffold sequences may contain non-immunoglobulin genes, such as ADAM6 (FIG. 1) needed for male fertility (Nishimura et al. Developmental Biol. 233(1): 204-213 (2011)). The partly canine immunoglobulin locus is introduced into the host cell using recombinase targeting sites that have been previously introduced upstream of the endogenous immunoglobulin $V_H$ gene locus and downstream of the endogenous $J_H$ gene locus on the same chromosome.

In other aspects, the non-coding regulatory or scaffold sequences derive (at least partially) from other sources, e.g., they could be rationally or otherwise designed sequences, sequences that are a combination of canine and other designed sequences, or sequences from other species.

In yet another specific aspect of the method, the introduced engineered partly canine immunoglobulin locus comprises canine immunoglobulin $V_L$ gene segment coding sequences, and further comprises i) canine L-chain J gene segment coding sequences and ii) non-coding regulatory or scaffold sequences corresponding to the non-coding regulatory or scaffold sequences present in the endogenous L chain locus of the non-canine mammalian host cell genome. The engineered partly canine immunoglobulin locus is preferably introduced into the host cell using recombinase targeting sites that have been previously introduced upstream of the endogenous immunoglobulin $V_L$ gene locus and downstream of the endogenous J gene locus on the same chromosome.

Preferably, the engineered partly canine immunoglobulin locus is synthesized as a single nucleic acid, and introduced into the non-canine mammalian host cell as a single nucleic acid region. The engineered partly canine immunoglobulin locus may also be synthesized in two or more contiguous segments, and introduced to the mammalian host cell as discrete segments. The engineered partly canine immunoglobulin locus can also be produced using recombinant methods and isolated prior being introduced into the non-canine mammalian host cell.

In another aspect, the invention provides methods for generating a non-canine mammalian cell comprising an engineered partly canine immunoglobulin locus, said method comprising: a) introducing into the genome of a non-canine mammalian host cell two or more sequence-specific recombination sites that are not capable of recombining with one another, wherein at least one recombination site is introduced upstream of an endogenous immunoglobulin variable region gene locus while at least one recombination site is introduced downstream of the endogenous immunoglobulin variable region gene locus on the same chromosome; b) providing a vector comprising an engineered partly canine immunoglobulin locus having i) canine immunoglobulin variable region gene coding sequences and ii) non-coding regulatory or scaffold sequences based on an endogenous immunoglobulin variable region gene locus of the host cell genome, wherein the partly canine immunoglobulin locus is flanked by the same two sequence-specific recombination sites that flank the endogenous immunoglobulin variable region gene locus of the host cell of a); c) introducing into the host cell the vector of step b) and a site specific recombinase capable of recognizing the two recombinase sites; d) allowing a recombination event to occur between the genome of the cell of a) and the engineered partly canine immunoglobulin locus, resulting in a replacement of the endogenous immunoglobulin variable region gene locus with the engineered partly canine immunoglobulin variable region gene locus. In a specific aspect of this method, the partly canine immunoglobulin locus comprises $V_H$ immunoglobulin gene segment coding sequences, and further comprises i) canine $D_H$ and $J_H$ gene segment coding sequences, ii) non-coding regulatory or scaffold sequences surrounding the codons of individual $V_H$, $D_H$, and $J_H$ gene segments present endogenously in the genome of the non-canine mammalian host, and iii) pre-D sequences based on the endogenous genome of the non-canine mammalian host cell. The recombinase targeting sites are introduced upstream of the endogenous immunoglobulin $V_H$ gene locus and downstream of the endogenous $D_H$ and $J_H$ gene locus.

Thus, in some embodiments, there is provided a transgenic rodent with a genome deleted of a rodent endogenous immunoglobulin variable gene locus and into which the deleted rodent endogenous immunoglobulin variable gene locus has been replaced with an engineered partly canine immunoglobulin locus comprising canine immunoglobulin variable gene coding sequences and non-coding regulatory or scaffold sequences based on the rodent endogenous immunoglobulin variable gene locus, wherein the engineered partly canine immunoglobulin locus of the transgenic rodent is functional and expresses immunoglobulin chains comprised of canine variable domains and rodent constant domains. In some aspects, the engineered partly canine immunoglobulin locus comprises canine $V_H$, $D_H$, and $J_H$ coding sequences, and in some aspects, the engineered partly canine immunoglobulin locus comprises canine $V_L$ and $J_L$ coding sequences. Some aspects provide a cell of B lymphocyte lineage from the transgenic rodent, a part or whole immunoglobulin molecule comprising canine variable domains and rodent constant domains derived from the cell of B lymphocyte lineage, a hybridoma cell derived from the cell of B lymphocyte, a part or whole immunoglobulin molecule comprising canine variable domains and rodent constant domains derived from the hybridoma cell, an immortalized cell derived from the cell of B lymphocyte lineage, a part or whole immunoglobulin molecule comprising canine variable domains and rodent constant domains derived from the immortalized cell. Other aspects of the invention provide a transgenic rodent, wherein the engineered partly canine immunoglobulin locus comprises canine $V_L$ and $J_L$ coding sequences, and a transgenic rodent, wherein the engineered partly canine immunoglobulin loci comprise canine $V_H$, $D_H$, and $J_H$ or $V_L$ and $J_L$ coding sequences. In some aspects, the rodent is a mouse. In some aspects, the non-coding regulatory sequences comprise the following sequences of endogenous host origin: promoters preceding each V gene segment, splice sites, and recombination signal sequences for V(D)J recombination; in other aspects, the engineered partly canine immunoglobulin locus further comprises one or more of the following sequences of endogenous host origin: ADAM6 gene, a Pax-5-Activated Intergenic Repeat (PAIR) elements, or CTCF binding sites from a heavy chain intergenic control region 1.

Preferably, the non-canine mammalian cell for use in each of the above methods is a mammalian cell, and more preferably a mammalian embryonic stem (ES) cell.

Once the cells have been subjected to the replacement of the endogenous immunoglobulin variable region gene locus by the introduced partly canine immunoglobulin variable region gene locus, the cells are selected and preferably isolated. In a preferred aspect of the invention, the cells are non-canine mammalian ES cells, preferably rodent ES cells, and at least one isolated ES cell clone is then utilized to create a transgenic non-canine mammal expressing the engineered partly canine immunoglobulin variable region gene locus.

An embodiment of the invention provides a method for generating the transgenic rodent, said method comprising: a) integrating at least one target site for a site-specific recombinase in a rodent cell's genome upstream of an endogenous immunoglobulin variable gene locus and at least one target site for a site-specific recombinase downstream of the endogenous immunoglobulin variable gene locus, wherein the endogenous immunoglobulin variable locus comprises $V_H$, $D_H$ and $J_H$ gene segments, or Vκ and Jκ gene segments, or Vλ and Jλ gene segments, or Vλ, Jλ and Cλ gene segments; b) providing a vector comprising an engineered partly canine immunoglobulin locus, said engineered partly canine immunoglobulin locus comprising chimeric canine immunoglobulin gene segments, wherein each of the partly canine immunoglobulin gene segment comprises canine immunoglobulin variable gene coding sequences and rodent non-coding regulatory or scaffold sequences, with the partly canine immunoglobulin variable gene locus being flanked by target sites for a site-specific recombinase wherein the target sites are capable of recombining with the target sites introduced into the rodent cell; c) introducing into the cell the vector and a site-specific recombinase capable of recognizing the target sites; d) allowing a recombination event to occur between the genome of the cell and the engineered partly canine immunoglobulin locus resulting in a replacement of the endogenous immunoglobulin variable gene locus with the engineered partly canine immunoglobulin locus; e) selecting a cell that comprises the engineered partly canine immunoglobulin variable locus generated in step d); and utilizing the cell to create a transgenic rodent comprising partly canine the engineered partly canine immunoglobulin variable locus. In some aspects, the cell is a rodent embryonic stem (ES) cell, and in some aspects the cell is a mouse embryonic stem (ES) cell. Some aspects of this method further comprise after, after step a) and before step b), a step of deleting the endogenous immunoglobulin variable gene locus by introduction of a recombinase that recognizes a first set of target sites, wherein the deleting step leaves in place at least one set of target sites that are not capable of recombining with one another in the rodent cell's genome. In some aspects, the vector comprises canine $V_H$, $D_H$, and $J_H$, coding sequences, and in some aspects the vector comprises canine $V_L$ and $J_L$ coding sequences. In some aspects, the vector further comprises a promoter, splice sites, and recombination signal sequences.

In another aspect, the invention provides a method for generating a transgenic non-canine mammal comprising an exogenously introduced, engineered partly canine immunoglobulin variable region gene locus, said method comprising: a) introducing into the genome of a non-canine mammalian host cell one or more sequence-specific recombination sites that flank an endogenous immunoglobulin variable region gene locus and are not capable of recombining with one another; b) providing a vector comprising a partly canine immunoglobulin locus having i) canine variable region gene coding sequences and ii) non-coding regulatory or scaffold sequences based on the endogenous host immunoglobulin variable region gene locus, wherein the coding and non-coding regulatory or scaffold sequences are flanked by the same sequence-specific recombination sites as those introduced to the genome of the host cell of a); c) introducing into the cell the vector of step b) and a site-specific recombinase capable of recognizing one set of recombinase sites; d) allowing a recombination event to occur between the genome of the cell of a) and the engineered partly canine immunoglobulin variable region gene locus, resulting in a replacement of the endogenous immunoglobulin variable region gene locus with the partly canine immunoglobulin locus; e) selecting a cell which comprises the partly canine immunoglobulin locus; and f) utilizing the cell to create a transgenic animal comprising the partly canine immunoglobulin locus.

In a specific aspect, the engineered partly canine immunoglobulin locus comprises canine $V_H$, $D_H$, and $J_H$ gene segment coding sequences, and non-coding regulatory and scaffold pre-D sequences (including a fertility-enabling gene) present in the endogenous genome of the non-canine mammalian host. The sequence-specific recombination sites are then introduced upstream of the endogenous immunoglobulin $V_H$ gene segments and downstream of the endogenous $J_H$ gene segments.

The invention provides another method for generating a transgenic non-canine animal comprising an engineered partly canine immunoglobulin locus, said method comprising: a) providing a non-canine mammalian cell having a genome that comprises two sets of sequence-specific recombination sites that are not capable of recombining with one another, and which flank a portion of an endogenous immunoglobulin variable region gene locus of the host genome; b) deleting the portion of the endogenous immunoglobulin locus of the host genome by introduction of a recombinase that recognizes a first set of sequence-specific recombination sites, wherein such deletion in the genome retains a second set of sequence-specific recombination sites; c) providing a vector comprising an engineered partly canine immunoglobulin variable region gene locus having canine coding sequences and non-coding regulatory or scaffold sequences based on the endogenous immunoglobulin variable region gene locus, where the coding and non-coding regulatory or scaffold sequences are flanked by the second set of sequence-specific recombination sites; d) introducing the vector of step c) and a site-specific recombinase capable of recognizing the second set of sequence-specific recombination sites into the cell; e) allowing a recombination event to occur between the genome of the cell and the partly canine immunoglobulin locus, resulting in a replacement of the endogenous immunoglobulin locus with the engineered partly canine immunoglobulin variable locus; f) selecting a cell that comprises the partly canine immunoglobulin variable region gene locus; and g) utilizing the cell to create a transgenic animal comprising the engineered partly canine immunoglobulin variable region gene locus.

The invention provides yet another method for generating a transgenic non-canine mammal comprising an engineered partly canine immunoglobulin locus, said method comprising: a) providing a non-canine mammalian embryonic stem ES cell having a genome that contains two sequence-specific recombination sites that are not capable of recombining with each other, and which flank the endogenous immunoglobulin variable region gene locus; b) providing a vector comprising an engineered partly canine immunoglobulin locus comprising canine immunoglobulin variable gene coding sequences and non-coding regulatory or scaffold sequences based on the endogenous immunoglobulin variable region gene locus, where the partly canine immunoglobulin locus is flanked by the same two sequence-specific recombination sites that flank the endogenous immunoglobulin variable region gene locus in the ES cell; c) bringing the ES cell and the vector into contact with a site-specific recombinase capable of recognizing the two recombinase sites under appropriate conditions to promote a recombination event resulting in the replacement of the endogenous immunoglobulin variable region gene locus with the engineered partly canine immunoglobulin variable region gene locus in the ES cell; d) selecting an ES cell that comprises the engineered partly canine immunoglobulin locus; and e) utilizing the cell to create a transgenic animal comprising the engineered partly canine immunoglobulin locus.

In a specific aspect of the invention, the transgenic non-canine mammal is a rodent, e.g., a mouse or a rat.

The invention further provides a non-canine mammalian cell and a non-canine transgenic mammal expressing an introduced immunoglobulin variable region gene locus having canine variable region gene coding sequences and non-coding regulatory or scaffold sequences based on the endogenous non-canine immunoglobulin locus of the host genome, where the non-canine mammalian cell and transgenic animal express chimeric antibodies consisting of fully canine H and/or L chain variable domains in conjunction with their respective constant regions that are native to the non-canine mammalian cell or animal.

Further, the invention also provides B cells from transgenic animals that are capable of expressing partly canine antibodies having fully canine variable sequences, wherein such B cells are immortalized to provide a source of a monoclonal antibody specific for a particular antigen.

The invention additionally provides canine immunoglobulin variable region gene sequences cloned from B cells for use in the production and/or optimization of antibodies for diagnostic, preventative and therapeutic uses.

Also, the invention provides hybridoma cells that are capable of producing partly canine monoclonal antibodies having fully canine immunoglobulin variable region sequences.

The invention also provides methods for removing the $V_H$ and $V_L$ exons that encode the H and L chain immunoglobulin variable domains from the monoclonal antibody-producing hybridomas and reconfigure them to contain canine constant regions, thereby creating a fully canine antibody that is not immunogenic when injected into dogs.

These and other aspects, objects and features are described in more detail below.

DEFINITIONS

Figure 1:
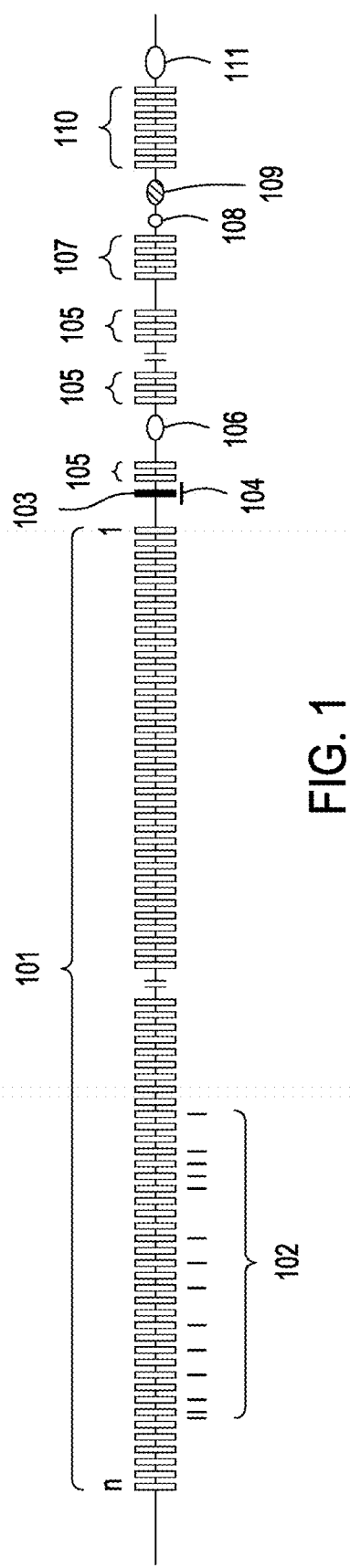
FIG. 1 is a schematic diagram of the endogenous mouse Igh locus located at the telomeric end of chromosome 12.

The terms used herein are intended to have the plain and ordinary meaning as understood by those of ordinary skill in the art. the following definitions are intended to aid the reader in understanding the present invention, but are not intended to vary or otherwise limit the meaning of such terms unless specifically indicated.

The term "locus" as used herein refers to a chromosomal segment or nucleic acid sequence that, respectively, is present endogenously in the genome or is (or about to be) exogenously introduced into the genome. For example, an immunoglobulin locus may include part or all of the genes (i.e., V, D, J gene segments as well as constant region genes) and intervening sequences (i.e., introns, enhancers, etc.) supporting the expression of immunoglobulin H or L chain polypeptides. Thus, a locus (e.g., $V_H$ gene locus) may refer to a specific portion of a larger locus (e.g., immunoglobulin H chain locus).

The term "immunoglobulin variable region gene" as used herein refers to a V, D, or J gene segment that encodes a portion of an immunoglobulin H or L chain variable domain.

The term "immunoglobulin variable region gene locus" as used herein refers to part of, or the entire, chromosomal segment or nucleic acid strand containing clusters of the V, D, or J gene segments and may include the non-coding regulatory or scaffold sequences.

"Partly canine" as used herein refers to a strand of nucleic acids, or their expressed protein and RNA products, comprising sequences corresponding to the sequences found in a given locus of both a canine and a non-canine mammalian host. "Partly canine" as used herein also refers to an animal comprising nucleic acid sequences from both a canine and a non-canine mammal, preferably a rodent. In the context of partly canine sequences of the invention, the partly canine nucleic acids have coding sequences of canine immunoglobulin H or L chain variable region gene segments and sequences based on the non-coding regulatory or scaffold sequences of the endogenous immunoglobulin locus of the non-canine mammal. The term "based on" when used with reference to endogenous non-coding regulatory or scaffold sequences from a non-canine mammalian host cell genome refers to the non-coding regulatory or scaffold sequences that are present in the corresponding endogenous locus of the mammalian host cell genome. "Non-coding regulatory sequences" refer to sequences that are known to be essential for (i) V(D)J recombination, (ii) isotype switching, and (iii) proper expression of the full-length immunoglobulin H or L chains following V(D)J recombination. "Non-coding regulatory sequences" may further include the following sequences of endogenous origin: enhancer and locus control elements such as the CTCF and PAIR sequences (Proudhon, et al., Adv. Immunol. 128:123-182 (2015)); promoters preceding each endogenous V gene segment; splice sites; introns; recombination signal sequences flanking each V, D, or J gene segment. Preferably, the "non-coding regulatory sequences" of the partly canine immunoglobulin locus share at least 70% homology with the corresponding non-coding sequences found in the targeted endogenous immunoglobulin locus of the non-canine mammalian host cell. "Scaffold sequences" refer to non-immunoglobulin genes, such as ADAM6, and other sequences with unknown functions present in the endogenous immunoglobulin locus of the host cell genome. In certain aspects, the non-coding regulatory or scaffold sequences are derived (at least partially) from other sources—e.g., they could be rationally or otherwise designed sequences, sequences that are a combination of canine and other designed sequences, or sequences from other species. It is to be understood that the phrase "non-coding regulatory or scaffold sequence" is inclusive in meaning (i.e., referring to both the non-coding regulatory sequence and the scaffold sequence existing in a given locus).

The term "homology targeting vector" refers to a nucleic acid sequence used to modify the endogenous genome of a mammalian host cell by homologous recombination; such nucleic acid sequence may comprise (i) targeting sequences with significant homologies to the corresponding endogenous sequences flanking a locus to be modified that is present in the genome of the non-canine mammalian host, (ii) at least one sequence-specific recombination site, (iii) non-coding regulatory or scaffold sequences, and (iv) optionally one or more selectable marker genes. As such, a homology targeting vector can be used in the present invention to introduce a sequence-specific recombination site into particular region of a host cell genome.

"Site-specific recombination" or "sequence-specific recombination" refers to a process of DNA rearrangement between two compatible recombination sequences (also referred to as "sequence-specific recombination sites" or "site-specific recombination sequences") including any of the following three events: a) deletion of a preselected nucleic acid flanked by the recombination sites; b) inversion of the nucleotide sequence of a preselected nucleic acid flanked by the recombination sites, and c) reciprocal exchange of nucleic acid sequences proximate to recombination sites located on different nucleic acid strands. It is to be understood that this reciprocal exchange of nucleic acid segments can be exploited as a targeting strategy to introduce an exogenous nucleic acid sequence into the genome of a host cell.

The term "targeting sequence" refers to a sequence homologous to DNA sequences in the genome of a cell that flank or are adjacent to the region of an immunoglobulin locus to be modified. The flanking or adjacent sequence may be within the locus itself or upstream or downstream of coding sequences in the genome of the host cell. Targeting sequences are inserted into recombinant DNA vectors which are used to transfect, e.g., ES cells such that sequences to be inserted into the host cell genome, such as the sequence of a recombination site, are flanked by the targeting sequences of the vector.

The term "site-specific targeting vector" as used herein refers to a vector comprising a nucleic acid encoding a sequence-specific recombination site, an engineered partly canine locus, and optionally a selectable marker gene, which is used to modify an endogenous immunoglobulin locus in a host using recombinase-mediated site-specific recombination. The recombination site of the targeting vector is suitable for site-specific recombination with another corresponding recombination site that has been inserted into a genomic sequence of the host cell (e.g., via a homology targeting vector), adjacent to an immunoglobulin locus that is to be modified. Integration of an engineered partly canine sequence into a recombination site in an immunoglobulin locus results in replacement of the endogenous locus by the exogenously introduced partly canine region.

The term "transgene" is used herein to describe genetic material that has been or is about to be artificially inserted into the genome of a cell, and particularly a cell of a mammalian host animal. The term "transgene" as used herein refers to a partly canine nucleic acid, e.g., a partly canine nucleic acid in the form of an engineered expression construct and/or a targeting vector.

"Transgenic animal" refers to a non-canine animal, usually a mammal, having an exogenous nucleic acid sequence present as an extrachromosomal element in a portion of its cells or stably integrated into its germ line DNA (i.e., in the genomic sequence of most or all of its cells). In the present invention, a partly canine nucleic acid is introduced into the germ line of such transgenic animals by genetic manipulation of, for example, embryos or embryonic stem cells of the host animal according to methods well known in the art.

A "vector" includes plasmids and viruses and any DNA or RNA molecule, whether self-replicating or not, which can be used to transform or transfect a cell.

DETAILED DESCRIPTION OF THE INVENTION

The practice of the techniques described herein may employ, unless otherwise indicated, conventional techniques and descriptions of organic chemistry, polymer technology, molecular biology (including recombinant techniques), cell biology, biochemistry, and sequencing technology, which are within the skill of those who practice in the art. Such conventional techniques include polymer array synthesis, hybridization and ligation of polynucleotides, and detection of hybridization using a label. Specific illustrations of suitable techniques can be had by reference to the examples herein. However, other equivalent conventional procedures can, of course, also be used. Such conventional techniques and descriptions can be found in standard laboratory manuals such as Green, et al., Eds. (1999), Genome Analysis: A Laboratory Manual Series (Vols. I-IV); Weiner, Gabriel, Stephens, Eds. (2007), Genetic Variation: A Laboratory Manual; Dieffenbach and Veksler, Eds. (2007), PCR Primer: A Laboratory Manual; Bowtell and Sambrook (2003), DNA Microarrays: A Molecular Cloning Manual; Mount (2004), Bioinformatics: Sequence and Genome Analysis; Sambrook and Russell (2006), Condensed Protocols from Molecular Cloning: A Laboratory Manual; and Sambrook and Russell (2002), Molecular Cloning: A Laboratory Manual (all from Cold Spring Harbor Laboratory Press); Stryer, L. (1995) Biochemistry (4th Ed.) W.H. Freeman, New York N.Y.; Gait, "Oligonucleotide Synthesis: A Practical Approach" 1984, IRL Press, London; Nelson and Cox (2000), Lehninger, Principles of Biochemistry $3^{rd}$ Ed., W. H. Freeman Pub., New York, N.Y.; and Berg et al. (2002) Biochemistry, $5^{th}$ Ed., W.H. Freeman Pub., New York, N.Y., all of which are herein incorporated in their entirety by reference for all purposes.

Note that as used herein and in the appended claims, the singular forms "a," "an," and "the" include plural referents unless the context clearly dictates otherwise. Thus, for example, reference to "a locus" refers to one or more loci, and reference to "the method" includes reference to equivalent steps and methods known to those skilled in the art, and so forth.

Unless defined otherwise, all technical and scientific terms used herein have the same meaning as commonly understood by one of ordinary skill in the art to which this invention belongs. All publications mentioned herein are incorporated by reference for the purpose of describing and disclosing devices, formulations and methodologies that may be used in connection with the presently described invention.

Where a range of values is provided, it is understood that each intervening value, between the upper and lower limit of that range and any other stated or intervening value in that stated range is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either both of those included limits are also included in the invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

In the humoral immune system, a diverse antibody repertoire is produced by combinatorial and junctional diversity of IgH (Igh) and IgL chain (Igl) gene loci by a process termed V(D)J recombination. In the developing B cell, the first recombination event to occur is between one D and one J gene segment of the heavy chain locus, and the DNA between these two gene segments is deleted. This D-J recombination is followed by the joining of one V gene segment from a region upstream of the newly formed DJ complex, forming a rearranged VDJ exon. All other sequences between the recombined V and D gene segments of the newly generated VDJ exon are deleted from the genome of the individual B cell. This rearranged exon is ultimately expressed on the B cell surface as the variable region of the H-chain polypeptide, which is associated with an L-chain polypeptide to form the B cell receptor (BCR). The murine and canine Ig loci are highly complex in the numbers of features they contain and in how their coding regions are diversified by V(D)J rearrangement; however, this complexity does not extend to the basic details of the structure of each variable region gene segment. The V, D and J gene segments are highly uniform in their compositions and organizations. For example, V gene segments have the following features that are arranged in essentially invariant sequential fashion in immunoglobulin loci: a short transcriptional promoter region (<600 bp in length), an exon encoding the majority of the signal peptide for the antibody chain; an intron; an exon encoding a small part of the signal peptide of the antibody chain and the majority of the antibody variable domain, and a 3' recombination signal sequence necessary for V(D)J rearrangement. Similarly, D gene segments have the following necessary and invariant features: a 5' recombination signal sequence, a coding region and a 3' recombination signal sequence. The J gene segments have the following necessary and invariant features: a 5' recombination signal sequence, a coding region and a 3' splice donor sequence.

The present invention provides non-canine mammalian cells comprising an exogenously introduced, engineered partly canine nucleic acid sequence comprising coding sequences for canine variable regions and non-coding regulatory or scaffold sequences present in the immunoglobulin locus of the mammalian host genome, e.g., mouse genomic non-coding sequences when the host mammal is a mouse. The canine genome $V_H$ region comprises approximately 80 $V_H$, 6 $D_H$ and 3 $J_H$ gene segments mapping to a 1.28 Mb region of canine chromosome 8. The lambda coding region maps to canine chromosome 26, while the kappa coding region maps to canine chromosome 17. The partly canine nucleic acid sequence allows the transgenic animal to produce a heavy chain repertoire comprising canine $V_H$ regions, while retaining the regulatory sequences and other elements that can be found within the intervening sequences of the host genome (e.g., rodent) that help to promote efficient antibody production and antigen recognition in the host. Similar to humans and mice, two types of Ig light chains (κ and λ) are expressed in dogs, though the κ to λ ratio differs significantly among these animals. In mice, approximately 96% of light chains in the serum antibodies are the κ type, while the κ type in humans accounts for only 66% of the total population of Ig L chains. In contrast, the L chain repertoire in dogs is dominated by λ.

The present invention comprises the use of a synthetic, or recombinantly produced, partly canine nucleic acids engineered to comprise both canine coding sequences and non-canine non-coding regulatory or scaffold sequences from an immunoglobulin $V_H$, Vλ or Vκ locus, or, in some aspects, a combination thereof.

In an aspect of the invention the synthetic H chain DNA segment contains the ADAM6 gene needed for male fertility, Pax-5-Activated Intergenic Repeats (PAIR) elements involved in Igh locus contraction and CTCF binding sites from the heavy chain intergenic control region 1, involved in regulating normal VDJ rearrangement ((Proudhon, et al., Adv. Immunol., 128:123-182 (2015)), or various combinations thereof. The locations of these endogenous non-coding regulatory and scaffold sequences in the mouse Igh locus are depicted in FIG. 1, which illustrates from left to right: the ~100 functional heavy chain variable region gene segments (101); PAIR, Pax-5 Activated Intergenic Repeats involved in Igh locus contraction for VDJ recombination (102); Adam6a, a disintegrin and metallopeptidase domain 6A gene required for male fertility (103); Pre-D region, a 21609 bp fragment upstream of the most distal $D_H$ gene segment, Ighd-5 $D_H$ (104); Intergenic Control Region 1 (IGCR1) that contains CTCF insulator sites to regulate $V_H$ gene segment usage (106); $D_H$, diversity gene segments (10-15 depending on the mouse strain) (105); four joining $J_H$ gene segments (107); Eμ, the intronic enhancer involved in VDJ recombination (108); Sμ, the μ switch region for isotype switching (109); eight heavy chain constant region genes: Cμ, Cδ, Cγ3, Cγ1, Cγ2b, C2γa/c, Cε, and Cα (110); 3' Regulatory Region (3'RR) that controls isotype switching and somatic hypermutation (111). FIG. 1 is modified from a figure taken from Proudhon, et al., Adv. Immunol., 128:123-182 (2015).

In preferred aspects of the invention, the engineered partly canine region to be integrated into a mammalian host cell comprises all or a substantial number of the known canine $V_H$ gene segments. In some instances, however, it may be desirable to use a subset of such $V_H$ gene segments, and in specific instances even as few as one canine $V_H$ coding sequence may be introduced into the cell or the animal of the invention.

The preferred aspects of the invention comprise non-canine mammals and mammalian cells comprising an engineered partly canine immunoglobulin locus that comprises coding sequences of canine $V_H$, canine $D_H$, and canine $J_H$ genes, and that further comprises non-coding regulatory and scaffold sequences, including pre-D sequences, based on the endogenous Igh locus of the non-canine mammalian host. In certain aspects, the exogenously introduced, engineered partly canine region can comprise a fully recombined V(D)J exon.

In a specific aspect of the invention, the transgenic non-canine mammal is a rodent, preferably a mouse, comprising an exogenously introduced, engineered partly canine immunoglobulin locus comprising codons for multiple canine $V_H$, canine $D_H$, and canine $J_H$ genes with intervening sequences, including a pre-D region, based on the intervening (non-coding regulatory or scaffold) sequences in the rodent. In a particularly preferred aspect, the transgenic non-canine rodent further comprises partly canine Igl loci comprising coding sequences of canine Vκ or Vλ genes, and Jκ or Jλ genes, respectively, in conjunction with their intervening (non-coding regulatory or scaffold) sequences corresponding to the immunoglobulin intervening sequences present in the Igl loci of the rodent.

In an exemplary embodiment, as set forth in more detail in the Examples section, the entire endogenous $V_H$ immunoglobulin locus of the mouse genome is deleted and subsequently replaced with 80 canine $V_H$ gene segments containing interspersed non-coding sequences corresponding to the non-coding sequences of the J558 $V_H$ locus of the mouse genome. The complete, exogenously introduced, engineered immunoglobulin locus further comprises canine $D_H$ and $J_H$ gene segments, as well as the mouse pre-D region. Thus, the canine $V_H$, $D_H$, and $J_H$ codon sequences are embedded in the rodent intergenic and intronic sequences.

The methods of the invention utilize a combination of homologous recombination and site-specific recombination to create the cells and animals of the invention. In some embodiments, a homology targeting vector is first used to introduce the sequence-specific recombination sites into the mammalian host cell genome at a desired location in the endogenous immunoglobulin loci. Preferably, in the absence of a recombinase protein, the sequence-specific recombination site inserted into the genome of a mammalian host cell by homologous recombination does not affect expression and amino acid codons of any genes in the mammalian host cell. This approach maintains the proper transcription and translation of the immunoglobulin genes which produce the desired antibody after insertion of recombination sites and, optionally, any additional sequence such as a selectable marker gene. However, in some cases it is possible to insert a recombinase site and other sequences into an immunoglobulin locus sequence such that an amino acid sequence of the antibody molecule is altered by the insertion, but the antibody still retains sufficient functionality for the desired purpose. Examples of such codon-altering homologous recombination may include the introduction of polymorphisms into the endogenous locus and changing the constant region exons so that a different isotype is expressed from the endogenous locus. The invention envisions encompassing such insertions as well.

In specific aspects of the invention, the homology targeting vector can be utilized to replace certain sequences within the endogenous genome as well as to insert certain sequence-specific recombination sites and one or more selectable marker genes into the host cell genome. It is understood by those of ordinary skill in the art that a selectable marker gene as used herein can be exploited to weed out individual cells that have not undergone homologous recombination and cells that harbor random integration of the targeting vector.

Exemplary methodologies for homologous recombination are described in U.S. Pat. Nos. 6,689,610; 6,204,061; 5,631,153; 5,627,059; 5,487,992; and 5,464,764, each of which is incorporated by reference in its entirety.

Site/Sequence-Specific Recombination

Site/sequence-specific recombination differs from general homologous recombination in that short specific DNA sequences, which are required for recognition by a recombinase, are the only sites at which recombination occurs. Depending on the orientations of these sites on a particular DNA strand or chromosome, the specialized recombinases that recognize these specific sequences can catalyze i) DNA excision or ii) DNA inversion or rotation. Site-specific recombination can also occur between two DNA strands if these sites are not present on the same chromosome. A number of bacteriophage- and yeast-derived site-specific recombination systems, each comprising a recombinase and specific cognate sites, have been shown to work in eukaryotic cells and are therefore applicable for use in the present invention, and these include the bacteriophage P1 Cre/lox, yeast FLP-FRT system, and the Dre system of the tyrosine family of site-specific recombinases. Such systems and methods of use are described, e.g., in U.S. Pat. Nos. 7,422,889; 7,112,715; 6,956,146; 6,774,279; 5,677,177; 5,885,836; 5,654,182; and 4,959,317, each of which is incorporated herein by reference to teach methods of using such recombinases.

Other systems of the tyrosine family of site-specific recombinases such as bacteriophage lambda integrase, HK2022 integrase, and in addition systems belonging to the separate serine family of recombinases such as bacteriophage phiC31, R4Tp901 integrases are known to work in mammalian cells using their respective recombination sites, and are also applicable for use in the present invention.

Since site-specific recombination can occur between two different DNA strands, site-specific recombination occurrence can be utilized as a mechanism to introduce an exogenous locus into a host cell genome by a process called recombinase-mediated cassette exchange (RMCE). The RMCE process can be exploited by the combined usage of wild-type and mutant sequence-specific recombination sites for the same recombinase protein together with negative selection. For example, a chromosomal locus to be targeted may be flanked by a wild-type LoxP site on one end and by a mutant LoxP site on the other. Likewise, an exogenous vector containing a sequence to be inserted into the host cell genome may be similarly flanked by a wild-type LoxP site on one end and by a mutant LoxP site on the other. When this exogenous vector is transfected into the host cell in the presence of Cre recombinase, Cre recombinase will catalyze RMCE between the two DNA strands, rather than the excision reaction on the same DNA strands, because the wild-type LoxP and mutant LoxP sites on each DNA strand are incompatible for recombination with each other. Thus, the LoxP site on one DNA strand will recombine with a LoxP site on the other DNA strand; similarly, the mutated LoxP site on one DNA strand will only recombine with a likewise mutated LoxP site on the other DNA strand.

The methods of the invention preferably utilize combined variants of the sequence-specific recombination sites that are recognized by the same recombinase for RMCE. Examples of such sequence-specific recombination site variants include those that contain a combination of inverted repeats or those which comprise recombination sites having mutant spacer sequences. For example, two classes of variant recombinase sites are available to engineer stable Cre-loxP integrative recombination. Both exploit sequence mutations in the Cre recognition sequence, either within the 8 bp spacer region or the 13-bp inverted repeats. Spacer mutants such as lox511 (Hoess, et al., Nucleic Acids Res, 14:2287-2300 (1986)), lox5171 and lox2272 (Lee and Saito, Gene, 216:55-65 (1998)), m2, m3, m7, and m11 (Langer, et al., Nucleic Acids Res, 30:3067-3077 (2002)) recombine readily with themselves but have a markedly reduced rate of recombination with the wild-type site. This class of mutants has been exploited for DNA insertion by RMCE using non-interacting Cre-Lox recombination sites and non-interacting FLP recombination sites (Baer and Bode, Curr Opin Biotechnol, 12:473-480 (2001); Albert, et al., Plant J, 7:649-659 (1995); Seibler and Bode, Biochemistry, 36:1740-1747 (1997); Schlake and Bode, Biochemistry, 33:12746-12751 (1994)).

Inverted repeat mutants represent the second class of variant recombinase sites. For example, LoxP sites can contain altered bases in the left inverted repeat (LE mutant) or the right inverted repeat (RE mutant). An LE mutant, lox71, has 5 bp on the 5' end of the left inverted repeat that is changed from the wild type sequence to TACCG (Araki, et al, Nucleic Acids Res, 25:868-872 (1997)). Similarly, the RE mutant, lox66, has the five 3'-most bases changed to CGGTA. Inverted repeat mutants are used for integrating plasmid inserts into chromosomal DNA with the LE mutant designated as the "target" chromosomal loxP site into which the "donor" RE mutant recombines. Post-recombination, loxP sites are located in cis, flanking the inserted segment. The mechanism of recombination is such that post-recombination one loxP site is a double mutant (containing both the LE and RE inverted repeat mutations) and the other is wild type (Lee and Sadowski, Prog Nucleic Acid Res Mol Biol, 80:1-42 (2005); Lee and Sadowski, J Mol Biol, 326:397-412 (2003)). The double mutant is sufficiently different from the wild-type site that it is unrecognized by Cre recombinase and the inserted segment is not excised.

In certain aspects, sequence-specific recombination sites can be introduced into introns, as opposed to coding nucleic acid regions or regulatory sequences. This avoids inadvertently disrupting any regulatory sequences or coding regions necessary for proper antibody expression upon insertion of sequence-specific recombination sites into the genome of the animal cell.

Introduction of the sequence-specific recombination sites may be achieved by conventional homologous recombination techniques. Such techniques are described in references such as e.g., Sambrook and Russell (2001) (Molecular cloning: a laboratory manual 3rd ed. (Cold Spring Harbor, N.Y.: Cold Spring Harbor Laboratory Press) and Nagy, A. (2003). (Manipulating the mouse embryo: a laboratory manual, 3rd ed. (Cold Spring Harbor, N.Y.: Cold Spring Harbor Laboratory Press). Genetic Recombination: Nucleic acid, Homology (biology), Homologous recombination, Non-homologous end joining, DNA repair, Bacteria, Eukaryote, Meiosis, Adaptive immune system, V(D)J recombination by Frederic P. Miller, Agnes F. Vandome, and John McBrewster (Paperback—Dec. 23, 2009).

Specific recombination into the genome can be facilitated using vectors designed for positive or negative selection as known in the art. In order to facilitate identification of cells that have undergone the replacement reaction, an appropriate genetic marker system may be employed and cells selected by, for example, use of a selection tissue culture medium. However, in order to ensure that the genome sequence is substantially free of extraneous nucleic acid sequences at or adjacent to the two end points of the replacement interval, desirably the marker system/gene can be removed following selection of the cells containing the replaced nucleic acid.

In one preferred aspect of the methods of the present invention, cells in which the replacement of all or part of the endogenous immunoglobulin locus has taken place are negatively selected against upon exposure to a toxin or drug. For example, cells that retain expression of HSV-TK can be selected against by using nucleoside analogues such as ganciclovir. In another aspect of the invention, cells comprising the deletion of the endogenous immunoglobulin locus may be positively selected for by use of a marker gene, which can optionally be removed from the cells following or as a result of the recombination event. A positive selection system that may be used is based on the use of two non-functional portions of a marker gene, such as HPRT, that are brought together through the recombination event. These two portions are brought into functional association upon a successful replacement reaction being carried out and wherein the functionally reconstituted marker gene is flanked on either side by further sequence-specific recombination sites (which are different from the sequence-specific recombination sites used for the replacement reaction), such that the marker gene can be excised from the genome, using an appropriate site-specific recombinase.

The recombinase may be provided as a purified protein, or as a protein expressed from a vector construct transiently transfected into the host cell or stably integrated into the host cell genome. Alternatively, the cell may be used first to generate a transgenic animal, which then may be crossed with an animal that expresses said recombinase.

Because the methods of the invention can take advantage of two or more sets of sequence-specific recombination sites within the engineered genome, multiple rounds of RMCE can be exploited to insert the partly canine immunoglobulin variable region genes into a non-canine mammalian host cell genome.

Although not yet routine for the insertion of large DNA segments, CRISPR technology is another method to introduce the chimeric canine Ig locus.

Generation of Transgenic Animals

In specific aspects, the invention provides methods for the creation of transgenic animals, preferably rodents, and more preferably mice, comprising the introduced partly canine immunoglobulin locus.

In one aspect, the host cell utilized for replacement of the endogenous immunoglobulin genes is an embryonic stem (ES) cell, which can then be utilized to create a transgenic mammal. Thus, in accordance with one aspect, the methods of the invention further comprise: isolating an embryonic stem cell which comprises the introduced partly canine immunoglobulin locus and using said ES cell to generate a transgenic animal that contains the replaced partly canine immunoglobulin locus.

EXAMPLES

The following examples are put forth so as to provide those of ordinary skill in the art with a complete disclosure and description of how to make and use the present invention, and are not intended to limit the scope of what the inventors regard as their invention, nor are they intended to represent or imply that the experiments below are all of or the only experiments performed. It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

Efforts have been made to ensure accuracy with respect to terms and numbers used (e.g., vectors, amounts, temperature, etc.) but some experimental errors and deviations should be accounted for. Unless indicated otherwise, parts are parts by weight, molecular weight is weight average molecular weight, temperature is in degrees centigrade, and pressure is at or near atmospheric.

The examples illustrate targeting by both a 5' vector and a 3' vector that flank a site of recombination and introduction of synthetic DNA. It will be apparent to one skilled in art upon reading the specification that the 5' vector targeting can take place first followed by the 3', or the 3' vector targeting can take place followed by the 5' vector. In some circumstances, targeting can be carried out simultaneously with dual detection mechanisms.

Example 1

Figure 2:
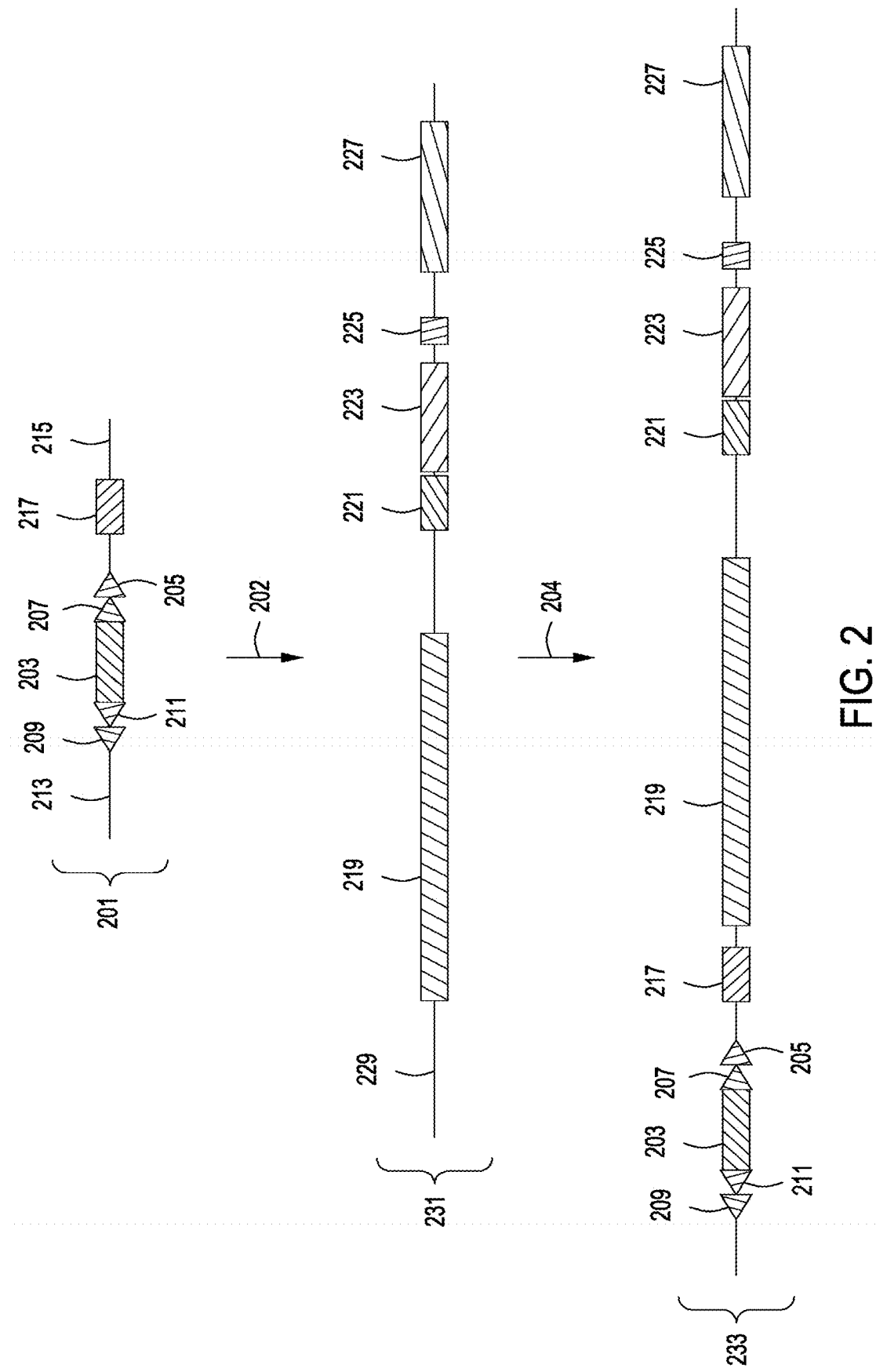
FIG. 2 is a schematic diagram illustrating the strategy of targeting by homologous recombination to introduce a first set of sequence-specific recombination sites into a region upstream of the H chain variable region gene locus in the genome of a non-canine mammalian host cell.

Introduction of an Engineered Partly Canine Immunoglobulin Variable Region Gene Locus into the Immunoglobulin H Chain Variable Region Gene Locus of a Non-Canine Mammalian Host Cell Genome An exemplary method illustrating the introduction of an engineered partly canine immunoglobulin locus into the genomic locus of a non-mammalian ES cell is illustrated in more detail in FIGS. 2-6. In FIG. 2, a homology targeting vector (201) is provided comprising a puromycin phosphotransferase-thymidine kinase fusion protein (puro-TK) (203) flanked by two different recombinase recognition sites (e.g., FRT (207) and loxP (205) for Flp and Cre, respectively) and two different mutant sites (e.g., modified mutant FRT (209) and mutant loxP (211)) that lack the ability to recombine with their respective wild-type counterparts/sites (i.e., wild-type FRT (207) and wild-type loxP (205)). The targeting vector comprises a diphtheria toxin receptor (DTR) cDNA (217) for use in negative selection of cells containing the introduced construct in future steps. The targeting vector also optionally comprises a visual marker such as a green fluorescent protein (GFP) (not shown). The regions 213 and 215 are homologous to the 5' and 3' portions, respectively, of a contiguous region (229) in the endogenous non-canine locus that is 5' of the genomic region comprising the endogenous non-canine $V_H$ gene segments (219). The homology targeting vector (201) is introduced (202) into the ES cell, which has an immunoglobulin locus (231) comprising endogenous $V_H$ gene segments (219), the pre-D region (221), the $D_H$ gene segments (223), $J_H$ gene segments (225), and the immunoglobulin constant gene region genes (227). The site-specific recombination sequences and the DTR cDNA from the homology targeting vector (201) are integrated (204) into the non-canine genome at a site 5' of the endogenous mouse $V_H$ gene locus, resulting in the genomic structure illustrated at 233. The ES cells that do not have the exogenous vector (201) integrated into their genome can be selected against (killed) by including puromycin in the culture medium; only the ES cells that have stably integrated the exogenous vector (201) into their genome and constitutively express the puro-TK gene are resistant to puromycin.

Figure 3:
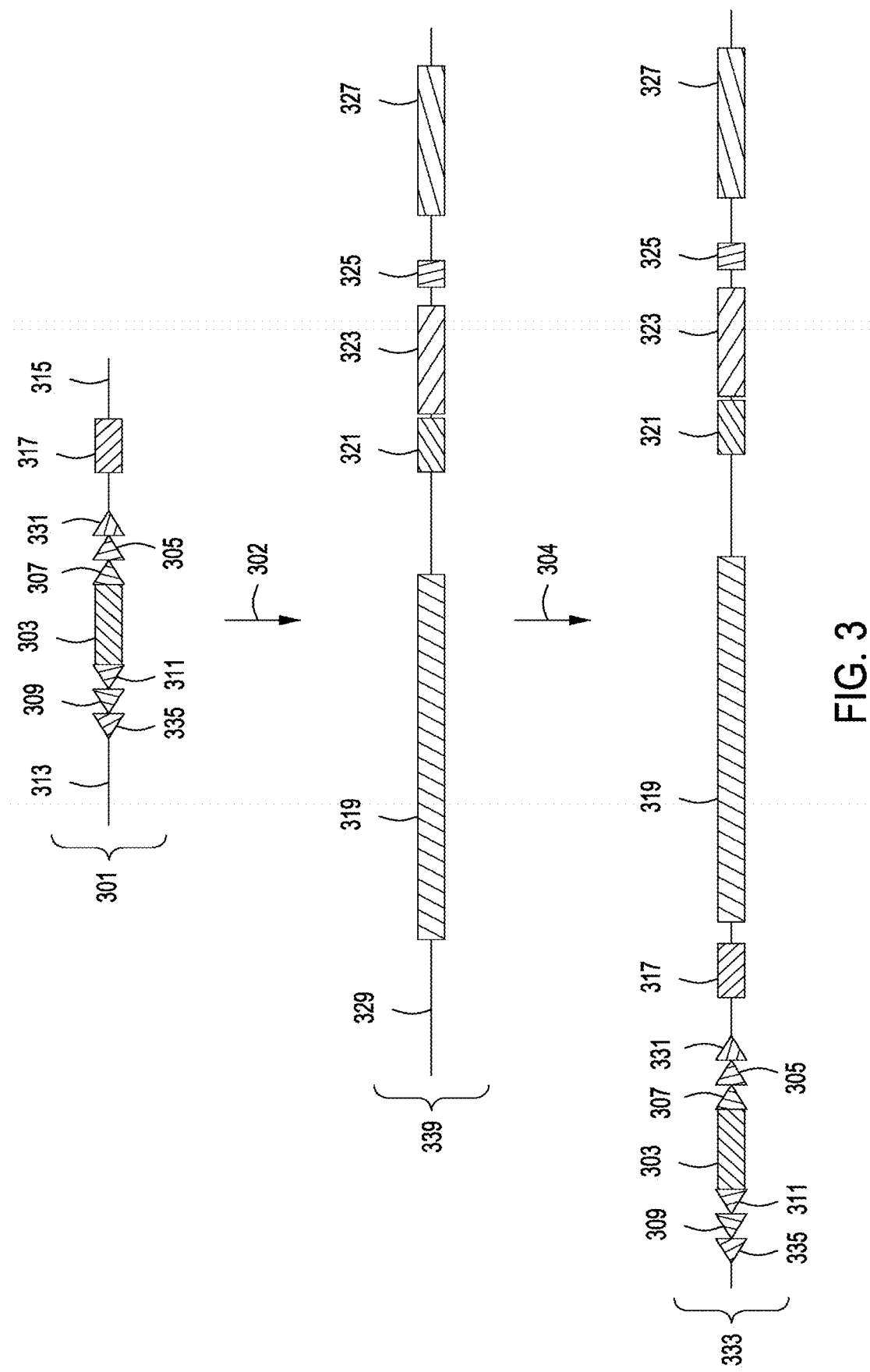
FIG. 3 is another schematic diagram illustrating the strategy of targeting by homologous recombination to introduce a first set of sequence-specific recombination sites into a region upstream of the H chain variable region gene locus in the genome of a non-canine mammalian host cell.

FIG. 3 illustrates effectively the same approach as FIG. 2, except that an additional set of sequence-specific recombination sites is added, e.g., a Rox site (331) and a modified Rox site (335) for use with the Dre recombinase. In FIG. 3, a homology targeting vector (301) is provided comprising a puro-TK fusion protein (303) flanked by wild type recombinase recognition sites for FRT (307), loxP (305), and Rox (331) and mutant sites for FRT (309) loxP (311) and Rox (333) recombinases that lack the ability to recombine with the wild-type sites 307, 305 and 331, respectively. The targeting vector also comprises a diphtheria toxin receptor (DTR) cDNA (317). The regions 313 and 315 are homologous to the 5' and 3' portions, respectively, of a contiguous region (329) in the endogenous non-canine locus that is 5' of the genomic region comprising the endogenous mouse $V_H$ gene segments (319). The homology targeting is introduced (302) into the mouse immunoglobulin locus (339), which comprises the endogenous $V_H$ gene segments (319), the pre-D region (321), the $D_H$ gene segments (323), $J_H$ (325) gene segments, and the constant region genes (327) of the Igh locus. The site-specific recombination sequences and the DTR cDNA (317) in the homology targeting vector (301) are integrated (304) into the mouse genome at a site 5' of the endogenous mouse $V_H$ gene locus, resulting in the genomic structure illustrated at 333.

Figure 4:
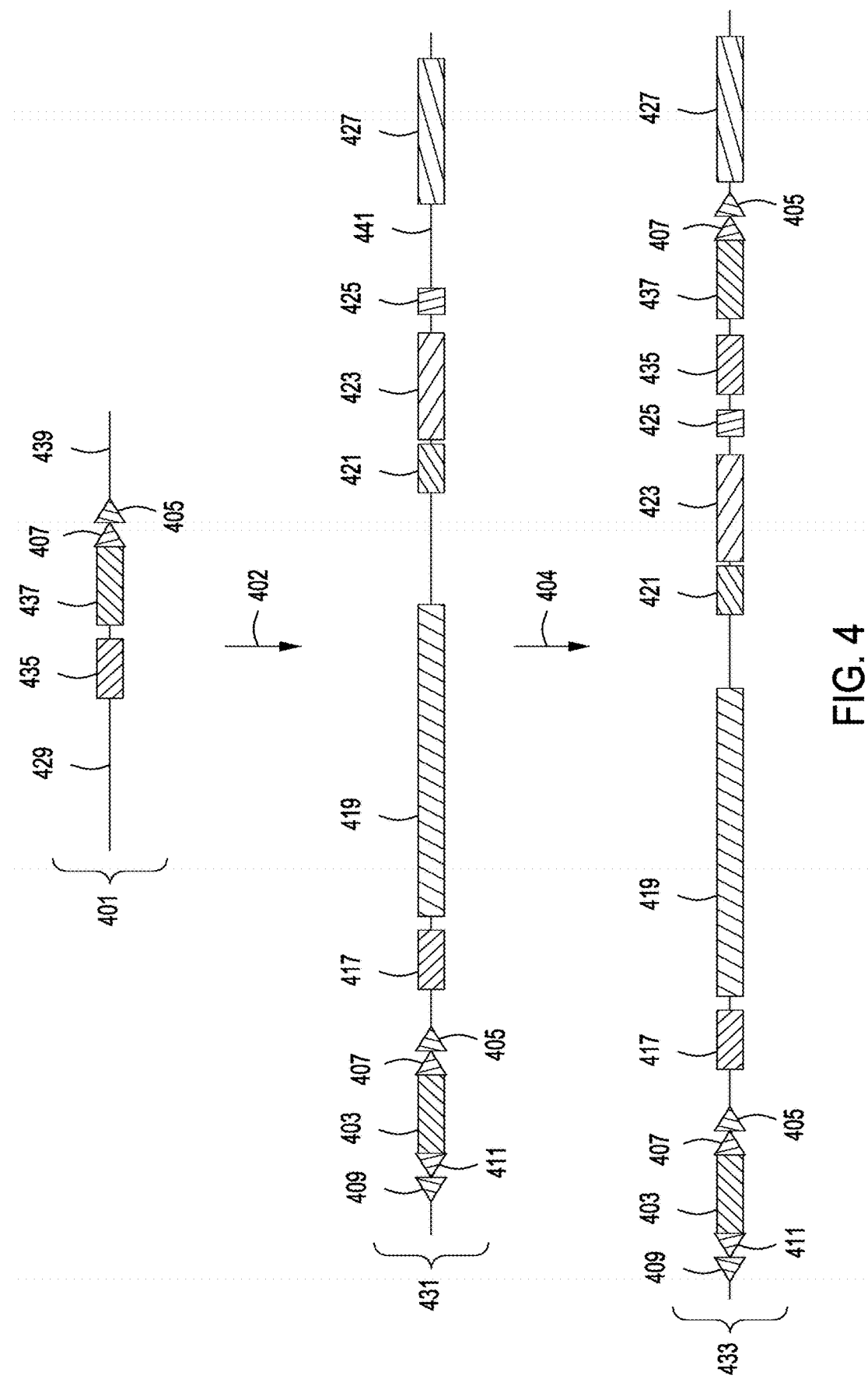
FIG. 4 is a schematic diagram illustrating the introduction of a second set of sequence-specific recombination sites into a region downstream of the H chain variable region gene locus in the genome of a non-canine mammalian cell via a homology targeting vector.

As illustrated in FIG. 4, a second homology targeting vector (401) is provided comprising an optional hypoxanthine-guanine phosphoribosyltransferase (HPRT) gene (435) that can be used for positive selection in HPRT-deficient ES cells; a neomycin resistance gene (437); recombinase recognition sites FRT (407) and loxP (405), for Flp and Cre, respectively, which have the ability to recombine with FRT (407) and loxP (405) sites previously integrated into the mouse genome from the first homology targeting vector. The previous homology targeting vector also consists of mutant FRT site (409), mutant loxP site (411), a puro-TK fusion protein (403), and a DTR cDNA at a site 5' of the endogenous mouse $V_H$ gene locus (419). The regions 429 and 439 are homologous to the 5' and 3' portions, respectively, of a contiguous region (441) in the endogenous mouse non-canine locus that is downstream of the endogenous $J_H$ gene segments (425) and upstream of the constant region genes (427). The homology targeting vector is introduced (402) into the modified mouse immunoglobulin locus (431), which comprises the endogenous $V_H$ gene segments (419), the pre-D region (421), the $D_H$ gene segments (423) the $J_H$ gene segments (425), and the constant region genes (427). The site-specific recombination sequences (407, 405), the HPRT gene (435) and a neomycin resistance gene (437) of the homology targeting vector are integrated (404) into the mouse genome upstream of the endogenous mouse constant region genes (427), resulting in the genomic structure illustrated at 433.

Figure 5:
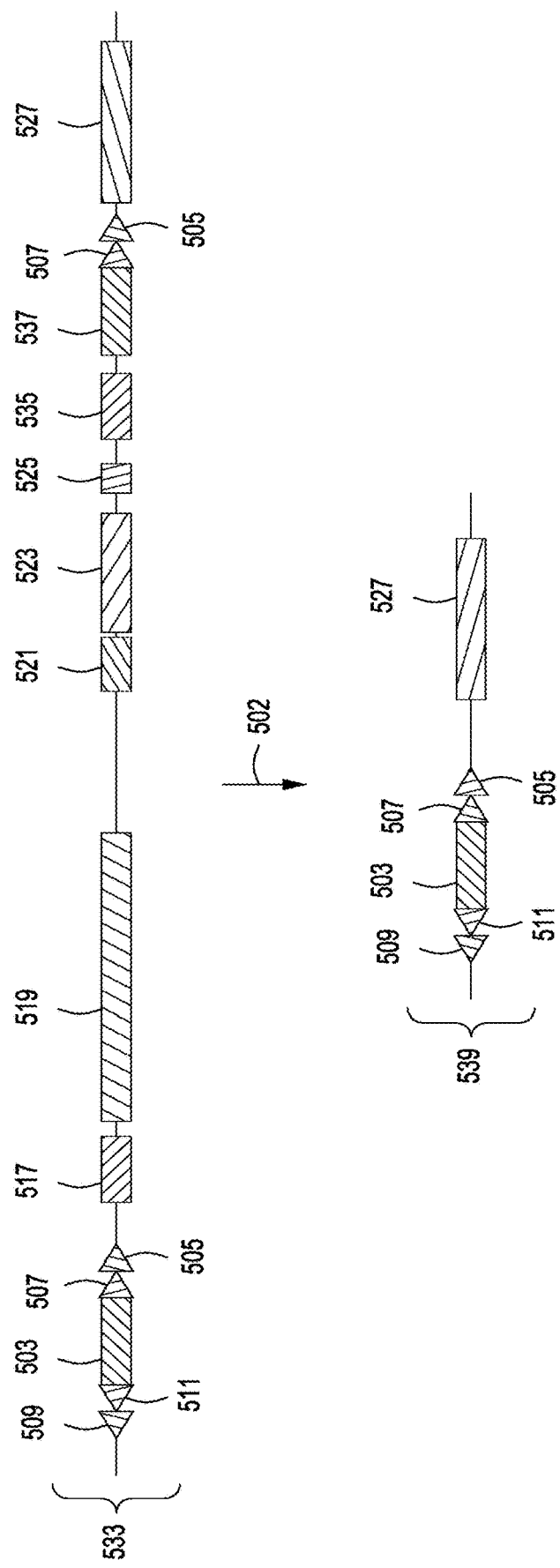
FIG. 5 is a schematic diagram illustrating deletion of the endogenous immunoglobulin H chain variable region gene locus from the genome of the non-canine mammalian host cell.

Once the recombination sites are integrated into the mammalian host cell genome, the endogenous region of the immunoglobulin domain is then subjected to recombination by introducing one of the recombinases corresponding to the sequence-specific recombination sites integrated into the genome, e.g., either Flp or Cre. Illustrated in FIG. 5 is a modified Igh locus of the mammalian host cell genome comprising two integrated DNA fragments. One fragment comprising mutant FRT site (509), mutant LoxP site (511), puro-TK gene (503), wild-type FRT site (507), and wild-type LoxP site (505), and DTR cDNA (517) is integrated upstream of the $V_H$ gene locus (519). The other DNA fragment comprising HPRT gene (535), neomycin resistance gene (537), wild-type FRT site (507), and wild-type LoxP site (505) is integrated downstream of the pre-D (521), $D_H$ (523) and $J_H$ (525) gene loci, but upstream of the constant region genes (527). In the presence of Flp or Cre (502), all the intervening sequences between the wild-type FRT or wild-type LoxP sites including the DTR gene (517), the endogenous Igh variable region gene loci (519, 521, 525), and the HPRT (535) and neomycin resistance (537) genes are deleted, resulting in a genomic structure illustrated at 539. The procedure depends on the second targeting having occurred on the same chromosome rather than on its homolog (i.e., in cis rather than in trans). If the targeting occurs in cis as intended in this invention, the cells are not sensitive to negative selection after Cre- or Flp-mediated recombination by diphtheria toxin introduced into the media, because the DTR gene which causes sensitivity to diphtheria toxin should be absent (deleted) from the host cell genome. Likewise, ES cells that harbor random integration of the first and/or second targeting vector(s) are rendered sensitive to diphtheria toxin by presence of the undeleted DTR gene.

ES cells that are insensitive to diphtheria toxin are then screened for the deletion of the endogenous variable region gene loci. The primary screening method for the deleted endogenous immunoglobulin locus can be carried out by Southern blotting, or by polymerase chain reaction (PCR) followed by confirmation with a secondary screening technique such as Southern blotting.

Figure 6:
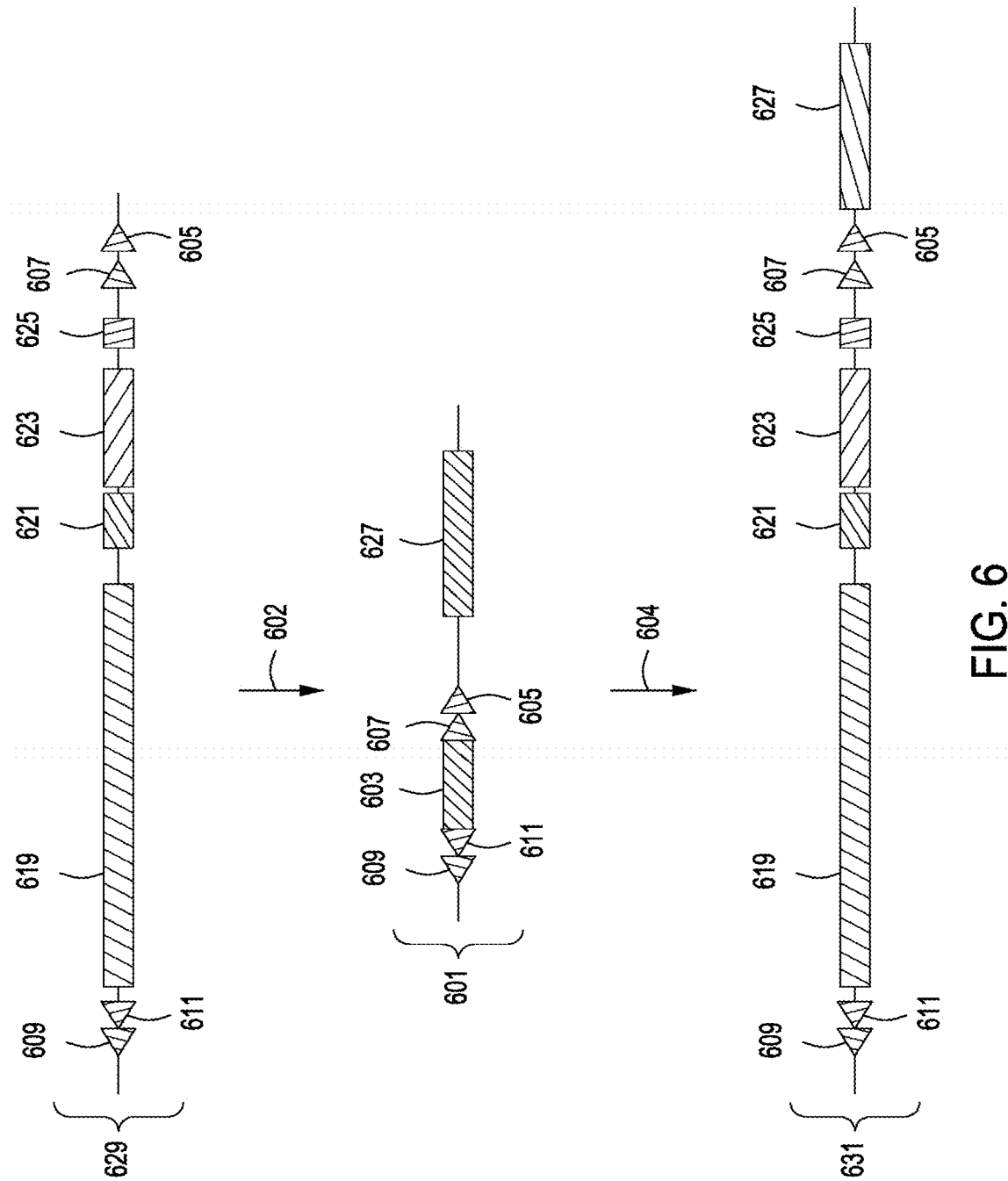
FIG. 6 is a schematic diagram illustrating the RMCE strategy to introduce an engineered partly canine immunoglobulin H chain locus into the non-canine mammalian host cell genome that has been previously modified to delete the endogenous immunoglobulin H chain variable region gene locus.

FIG. 6 illustrates introduction of the engineered partly canine sequence into a non-canine genome previously modified to delete part of the endogenous Igh locus that encodes the heavy chain variable region domains as well as all the intervening sequences between the $V_H$ and $J_H$ gene locus. A site-specific targeting vector (629) comprising partly canine $V_H$ gene locus (619), endogenous non-canine pre-D gene region (621), partly canine $D_H$ gene locus (623), partly canine $J_H$ gene locus (625), as well as flanking mutant FRT (609), mutant LoxP (611), wild-type FRT (607), and wild-type LoxP (605) sites is introduced (602) into the host cell. Specifically, the partly canine $V_H$ locus (619) comprises 47 functional canine $V_H$ coding sequences in conjunction with the intervening sequences based on the endogenous non-canine genome sequences; the pre-D region (621) comprises a 21.6 kb mouse sequence with significant homology to the corresponding region of the endogenous canine Igh locus; the $D_H$ gene locus (623) comprises codons of 6 $D_H$ gene segments embedded in the intervening sequences surrounding the endogenous non-canine $D_H$ gene segments; and the $J_H$ gene locus (625) comprises codons of 5 canine $J_H$ gene segments embedded in the intervening sequences based on the endogenous non-canine genome. The Igh locus (601) of the host cell genome has been previously modified to delete all the $V_H$, $D_H$, and $J_H$ gene segments including the intervening sequences as described in FIG. 5. As a consequence of this modification, the endogenous non-canine host cell Igh locus (601) is left with a puro-TK fusion gene, which is flanked by a mutant FRT site (609) and a mutant LoxP site (611) upstream as well as a wild-type FRT (607) and a wild-type LoxP (605) downstream. Upon introduction of the appropriate recombinase (604), the partly canine immunoglobulin locus is integrated into the genome upstream of the endogenous non-canine constant region genes (627), resulting in the genomic structure illustrated at 631.

The sequences of the canine $V_H$, $D_H$ and $J_H$ gene segment coding regions are in Table 1.

Primary screening procedure for the introduction of the partly canine immunoglobulin locus can be carried out by Southern blotting, or by PCR with confirmation from secondary screening methods such as Southern blotting. The screening methods are designed to detect the presence of the inserted $V_H$ and/or $J_H$ gene loci, as well as all the intervening sequences.

Example 2

Figure 7:
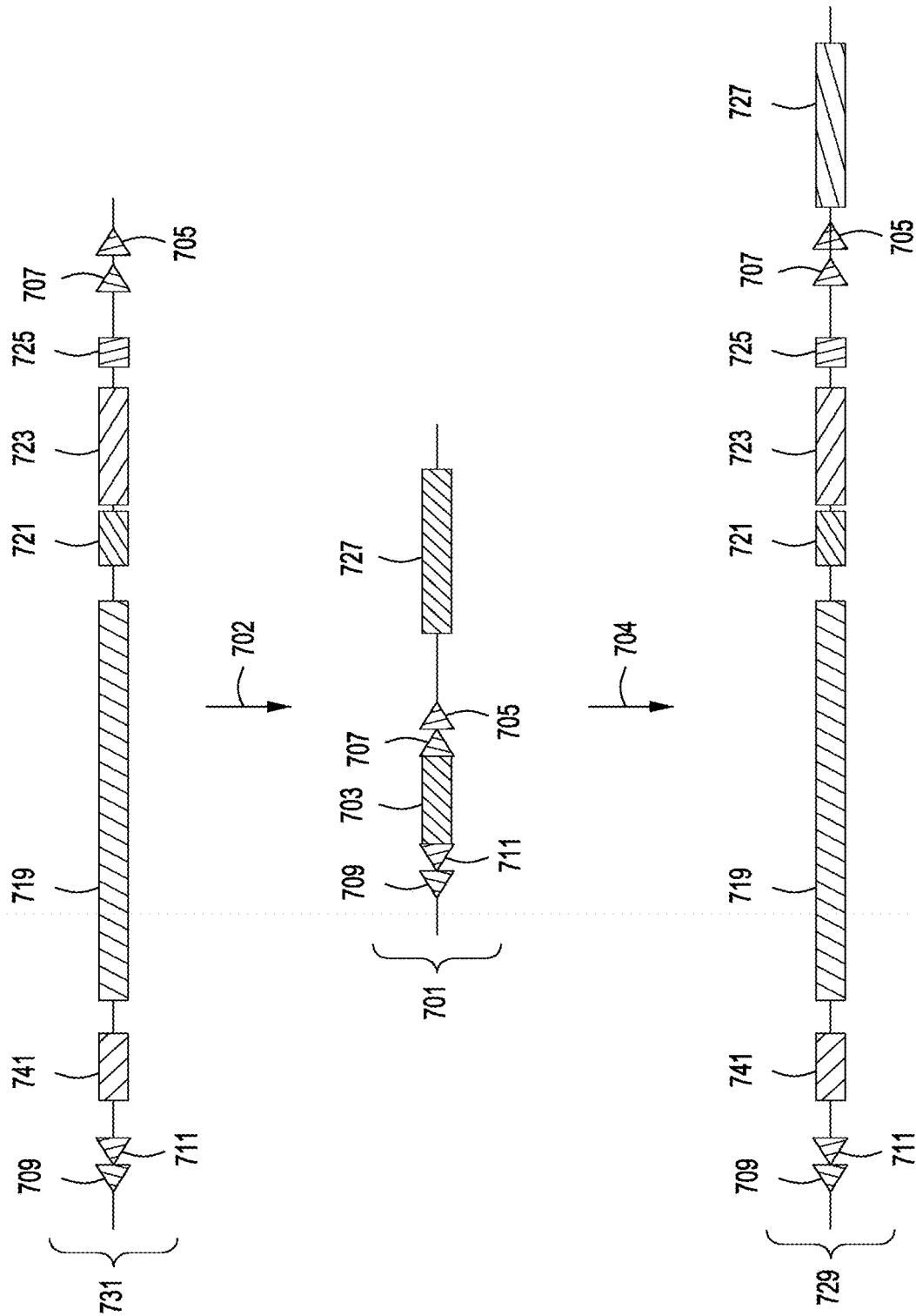
FIG. 7 is a schematic diagram illustrating the RMCE strategy to introduce an engineered partly canine immunoglobulin H chain locus comprising additional regulatory sequences into the non-canine mammalian host cell genome that has been previously modified to delete the endogenous immunoglobulin H chain variable region genes.

Introduction of an Engineered Partly Canine Immunoglobulin Variable Region Gene Locus Comprising Additional Non-Coding Regulatory or Scaffold Sequences into the Immunoglobulin H Chain Variable Region Gene Locus of a Non-Canine Mammalian Host Cell Genome In certain aspects, the partly canine immunoglobulin locus comprises the elements as described in Example 1, but with additional non-coding regulatory or scaffold sequences e.g., sequences strategically added to introduce additional regulatory sequences, to ensure the desired spacing within the introduced immunoglobulin locus, to ensure that certain coding sequences are in adequate juxtaposition with other sequences adjacent to the replaced immunoglobulin locus, and the like. FIG. 7 illustrates the introduction of a second exemplary engineered partly canine sequence to the modified non-canine genome as produced in FIGS. 2-5 and described in Example 1 above.

FIG. 7 illustrates introduction of the engineered partly canine sequence into the mouse genome previously modified to delete part of the endogenous non-canine Igh locus that encodes the heavy chain variable region domains as well as all the intervening sequences between the endogenous $V_H$ and $J_H$ gene loci. A site-specific targeting vector (731) comprising an engineered partly canine immunoglobulin locus to be inserted into the non-canine host genome is introduced (702) into the genomic region (701). The site-specific targeting vector (731) comprising a partly canine $V_H$ gene locus (719), mouse pre-D region (721), partly canine $D_H$ gene locus (723), partly canine $J_H$ gene locus (725), PAIR elements (741), as well as flanking mutant FRT (709), mutant LoxP (711) wild-type FRT (707) and wild-type LoxP (705) sites is introduced (702) into the host cell. Specifically, the engineered partly canine $V_H$ gene locus (719) comprises 80 canine $V_H$ gene segment coding regions in conjunction with intervening sequences based on the endogenous non-canine genome sequences; the pre-D region (721) comprises a 21.6 kb non-canine sequence present upstream of the endogenous non-canine genome; the $D_H$ region (723) comprises codons of 6 canine $D_H$ gene segments embedded in the intervening sequences surrounding the endogenous non-canine $D_H$ gene segments; and the $J_H$ gene locus (725) comprises codons of 3 canine $J_H$ gene segments embedded in the intervening sequences based on the endogenous non-canine genome sequences. The Igh locus (701) of the host cell genome has been previously modified to delete all the $V_H$, $D_H$, and $J_H$ gene segments including the intervening sequences as described in relation to FIG. 5. As a consequence of this modification, the endogenous non-canine Igh locus (701) is left with a puro-TK fusion gene (703), which is flanked by a mutant FRT site (709) and a mutant LoxP site (711) upstream as well as a wild-type FRT (707) and a wild-type LoxP (705) downstream. Upon introduction of the appropriate recombinase (704), the engineered partly canine immunoglobulin locus is integrated into the genome upstream of the endogenous mouse constant region genes (727), resulting in the genomic structure illustrated at 729.

The primary screening procedure for the introduction of the engineered partly canine immunoglobulin region can be carried out by Southern blotting, or by PCR with confirmations from secondary screening methods such as Southern blotting. The screening methods are designed to detect the presence of the inserted $V_H$ and/or $J_H$ gene loci, as well as all the intervening sequences.

Example 3

Figure 8:
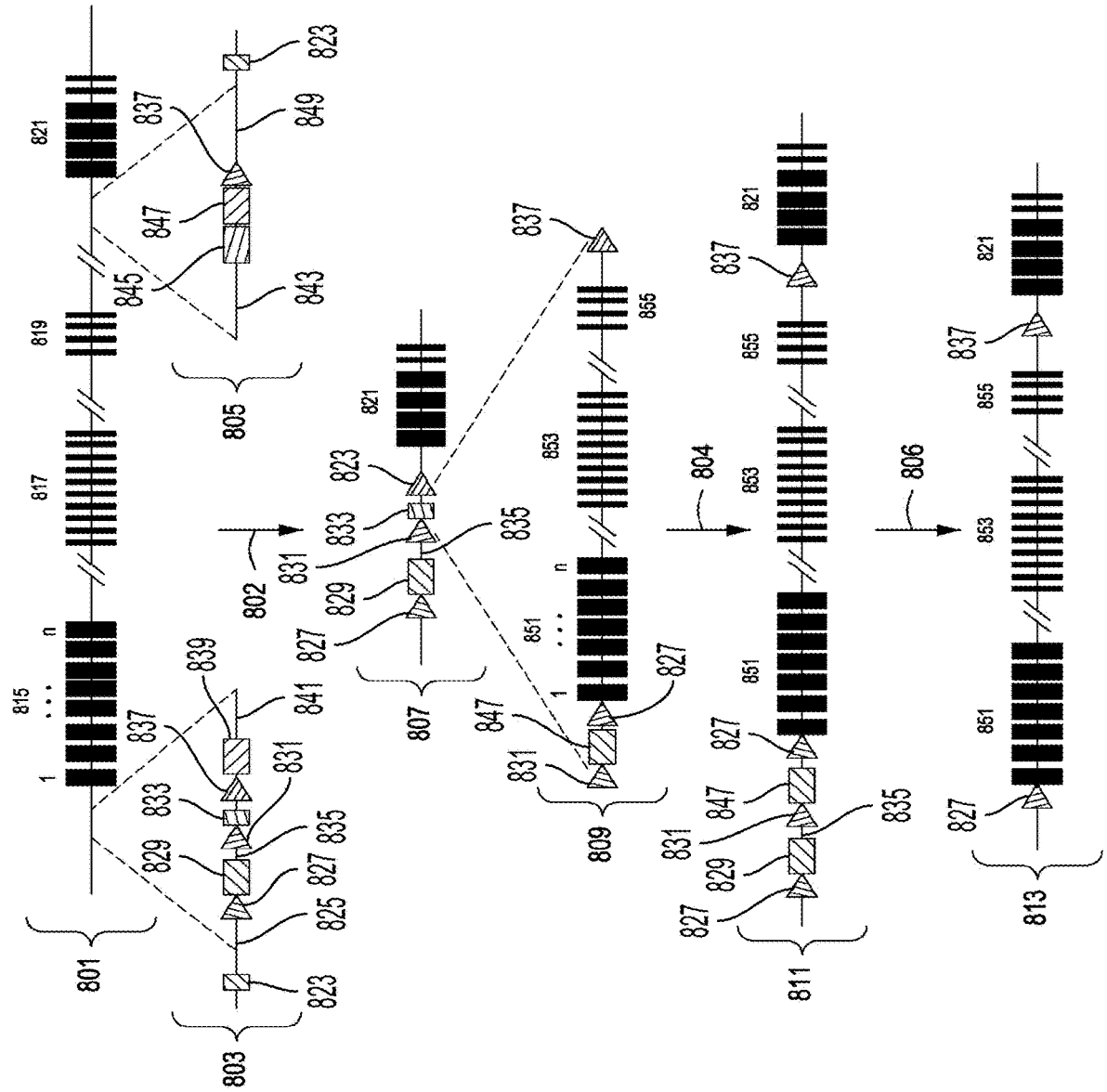
FIG. 8 is a schematic diagram illustrating the introduction of an engineered partly canine immunoglobulin H chain variable region gene locus into the endogenous immunoglobulin H chain locus of the mouse genome.

Introduction of an Engineered Partly Canine Immunoglobulin Locus into the Immunoglobulin Heavy Chain Gene Locus of a Mouse Genome A method for replacing a portion of a mouse genome with an engineered partly canine immunoglobulin locus is illustrated in FIG. 8. This method uses introduction of a first site-specific recombinase recognition sequence into the mouse genome followed by the introduction of a second site-specific recombinase recognition sequence into the mouse genome. The two sites flank the entire clusters of endogenous mouse $V_H$, $D_H$ and $J_H$ region gene segments. The flanked region is deleted using the relevant site-specific recombinase, as described herein.

The targeting vectors (803, 805) employed for introducing the site-specific recombinase sequences on either side of the $V_H$ (815), $D_H$ (817) and $J_H$ (819) gene segment clusters and upstream of the constant region genes (821) in the wild-type mouse immunoglobulin locus (801) include an additional site-specific recombination sequence that has been modified so that it is still recognized efficiently by the recombinase, but does not recombine with unmodified sites. This mutant modified site (e.g., lox5171) is positioned in the targeting vector such that after deletion of the endogenous $V_H$, $D_H$ and $J_H$ gene segments (802) it can be used for a second site-specific recombination event in which a non-native piece of DNA is moved into the modified Igh locus by RMCE. In this example, the non-native DNA is a synthetic nucleic acid comprising both canine and non-canine sequences (809).

Two gene targeting vectors are constructed to accomplish the process just outlined. One of the vectors (803) comprises mouse genomic DNA taken from the 5' end of the Igh locus, upstream of the most distal $V_H$ gene segment. The other vector (805) comprises mouse genomic DNA taken from within the locus downstream of the $J_H$ gene segments.

The key features of the 5' vector (803) in order from 5' to 3' are as follows: a gene encoding the diphtheria toxin A (DTA) subunit under transcriptional control of a modified herpes simplex virus type I thymidine kinase gene promoter coupled to two mutant transcriptional enhancers from the polyoma virus (823); 4.5 Kb of mouse genomic DNA mapping upstream of the most distal $V_H$ gene segment in the Igh locus (825); a FRT recognition sequence for the Flp recombinase (827); a piece of genomic DNA containing the mouse Polr2a gene promoter (829); a translation initiation sequence (methionine codon embedded in a "Kozak" consensus sequence, 835)); a mutated loxP recognition sequence (lox5171) for the Cre recombinase (831); a transcription termination/polyadenylation sequence (pA. 833); a loxP recognition sequence for the Cre recombinase (837); a gene encoding a fusion protein comprised of a protein conferring resistance to puromycin fused to a truncated form of the thymidine kinase (pu-TK) under transcriptional control of the promoter from the mouse phosphoglycerate kinase 1 gene (839); and 3 Kb of mouse genomic DNA (841) mapping close to the 4.5 Kb mouse genomic DNA sequence present near the 5' end of the vector and arranged in the native relative orientation.

The key features of the 3' vector (805) in order from 5' to 3' are as follows; 3.7 Kb of mouse genomic DNA mapping within the intron between the $J_H$ and $C_H$ gene loci (843); an HPRT gene under transcriptional control of the mouse Polr2a gene promoter (845); a neomycin resistance gene under the control of the mouse phosphoglycerate kinase 1 gene promoter (847); a loxP recognition sequence for the Cre recombinase (837); 2.1 Kb of mouse genomic DNA (849) that maps immediately downstream of the 3.7 Kb mouse genomic DNA fragment present near the 5' end of the vector and arranged in the native relative orientation; and a gene encoding the DTA subunit under transcriptional control of a modified herpes simplex virus type I thymidine kinase gene promoter coupled to two mutant transcriptional enhancers from the polyoma virus (823).

Mouse embryonic stem (ES) cells (derived from C57Bl/6NTac mice) are transfected by electroporation with the 3' vector (805) according to widely used procedures. Prior to electroporation, the vector DNA is linearized with a rare-cutting restriction enzyme that cuts only in the prokaryotic plasmid sequence or the polylinker associated with it. The transfected cells are plated and after ~24 hours they are placed under positive selection for cells that have integrated the 3' vector into their DNA by using the neomycin analogue drug G418. There is also negative selection for cells that have integrated the vector into their DNA but not by homologous recombination. Non-homologous recombination will result in retention of the DTA gene (823), which will kill the cells when the gene is expressed, whereas the DTA gene is deleted by homologous recombination since it lies outside of the region of vector homology with the mouse Igh locus. Colonies of drug-resistant ES cells are physically extracted from their plates after they became visible to the naked eye about a week later. These picked colonies are disaggregated, re-plated in micro-well plates, and cultured for several days. Thereafter, each of the clones of cells is divided such that some of the cells can be frozen as an archive, and the rest used for isolation of DNA for analytical purposes.

DNA from the ES cell clones is screened by PCR using a widely practiced gene-targeting assay design. For this assay, one of the PCR oligonucleotide primer sequences maps outside the region of identity shared between the 3' vector (805) and the genomic DNA, while the other maps within the novel DNA between the two arms of genomic identity in the vector, i.e., in the HPRT (845) or neomycin resistance (847) genes. According to the standard design, these assays detect pieces of DNA that would only be present in clones of ES cells derived from transfected cells that undergo fully legitimate homologous recombination between the 3' targeting vector and the endogenous mouse Igh locus. Two separate transfections are performed with the 3' vector (805). PCR-positive clones from the two transfections are selected for expansion followed by further analysis using Southern blot assays.

The Southern blot assays are performed according to widely used procedures using three probes and genomic DNA digested with multiple restriction enzymes chosen so that the combination of probes and digests allow the structure of the targeted locus in the clones to be identified as properly modified by homologous recombination. One of the probes maps to DNA sequence flanking the 5' side of the region of identity shared between the 3' targeting vector and the genomic DNA; a second probe maps outside the region of identity but on the 3' side; and the third probe maps within the novel DNA between the two arms of genomic identity in the vector, i.e., in the HPRT (845) or neomycin resistance (847) genes. The Southern blot identifies the presence of the expected restriction enzyme-generated fragment of DNA corresponding to the correctly mutated, i.e., by homologous recombination with the 3' Igh targeting vector, part of the Igh locus as detected by one of the external probes and by the neomycin or HPRT probe. The external probe detects the mutant fragment and also a wild-type fragment from the non-mutant copy of the immunoglobulin Igh locus on the homologous chromosome.

Karyotypes of PCR- and Southern blot-positive clones of ES cells are analyzed using an in situ fluorescence hybridization procedure designed to distinguish the most commonly arising chromosomal aberrations that arise in mouse ES cells. Clones with such aberrations are excluded from further use. ES cell clones that are judged to have the expected correct genomic structure based on the Southern blot data—and that also do not have detectable chromosomal aberrations based on the karyotype analysis—are selected for further use.

Acceptable clones are then modified with the 5' vector (803) using procedures and screening assays that are essentially identical in design to those used with the 3' vector (805) except that puromycin selection is used instead of G418/neomycin for selection. The PCR assays, probes and digests are also tailored to match the genomic region being modified by the 5' vector (805).

Clones of ES cells that have been mutated in the expected fashion by both the 3' and the 5' vectors, i.e., doubly targeted cells carrying both engineered mutations, are isolated following vector targeting and analysis. The clones must have undergone gene targeting on the same chromosome, as opposed to homologous chromosomes (i.e., the engineered mutations created by the targeting vectors must be in cis on the same DNA strand rather than in trans on separate homologous DNA strands). Clones with the cis arrangement are distinguished from those with the trans arrangement by analytical procedures such as fluorescence in situ hybridization of metaphase spreads using probes that hybridize to the novel DNA present in the two gene targeting vectors (803 and 805) between their arms of genomic identity. The two types of clones can also be distinguished from one another by transfecting them with a vector expressing the Cre recombinase, which deletes the pu-TK (839), HPRT (845) and neomycin resistance (847) genes if the targeting vectors have been integrated in cis, and then comparing the number of colonies that survive ganciclovir selection against the thymidine kinase gene introduced by the 5' vector (803) and by analyzing the drug resistance phenotype of the surviving clones by a "sibling selection" screening procedure in which some of the cells from the clone are tested for resistance to puromycin or G418/neomycin. Cells with the cis arrangement of mutations are expected to yield approximately $10^3$ more ganciclovir-resistant clones than cells with the trans arrangement. The majority of the resulting cis-derived ganciclovir-resistant clones are also sensitive to both puromycin and G418/neomycin, in contrast to the trans-derived ganciclovir-resistant clones, which should retain resistance to both drugs. Doubly targeted clones of cells with the cis-arrangement of engineered mutations in the heavy chain locus are selected for further use.

The doubly targeted clones of cells are transiently transfected with a vector expressing the Cre recombinase and the transfected cells subsequently are placed under ganciclovir selection, as in the analytical experiment summarized above. Ganciclovir-resistant clones of cells are isolated and analyzed by PCR and Southern blot for the presence of the expected deletion between the two engineered mutations created by the 5' (803) and the 3' (805) targeting vectors. In these clones, the Cre recombinase causes a recombination (802) to occur between the loxP sites (837) introduced into the heavy chain locus by the two vectors to create the genomic DNA configuration shown at 807. Because the loxP sites are arranged in the same relative orientations in the two vectors, recombination results in excision of a circle of DNA comprising the entire genomic interval between the two loxP sites. The circle does not contain an origin of replication and thus is not replicated during mitosis and therefore is lost from the cells as they undergo proliferation. The resulting clones carry a deletion of the DNA that was originally between the two loxP sites. Clones that have the expected deletion are selected for further use.

ES cell clones carrying the deletion of sequence in one of the two homologous copies of their immunoglobulin heavy chain locus are retransfected (804) with a Cre recombinase expression vector together with a piece of DNA (809) comprising a partly canine immunoglobulin heavy chain locus containing part-canine/part-mouse $V_H$, $D_H$ and $J_H$ region gene segments. The key features of this piece of synthetic DNA (809) are the following: a lox5171 site (831); a neomycin resistance gene open reading frame (847) lacking the initiator methionine codon, but in-frame and contiguous with an uninterrupted open reading frame in the lox5171 site a FRT site (827); an array of 47 functional canine $V_H$ heavy chain variable region genes (851), each comprised of canine coding sequences embedded in mouse noncoding sequences; optionally a 21.6 kb pre-D region from the mouse heavy chain locus (not shown); a 58 Kb piece of DNA containing the 6 canine $D_H$ gene segments (853) and 5 canine $J_H$ gene segments (855) where the canine coding sequences are embedded in mouse noncoding sequences; a loxP site (837) in opposite relative orientation to the lox5171 site (831).

The transfected clones are placed under G418 selection, which enriches for clones of cells that have undergone RMCE in which the engineered partly canine donor immunoglobulin locus (809) is integrated in its entirety into the deleted endogenous immunoglobulin heavy chain locus between the lox5171 (831) and loxP (837) sites to create the DNA region illustrated at 811. Only cells that have properly undergone RMCE have the capability to express the neomycin resistance gene (847) because the promoter (829) as well as the initiator methionine codon (835) required for its expression are not present in the vector (809) and are already pre-existing in the host cell Igh locus (807). The remaining elements from the 5' vector (803) are removed via Flp-mediated recombination (806) in vitro or in vivo, resulting in the final canine-based locus as shown at 813.

G418-resistant ES cell clones are analyzed by PCR and Southern blot to determine if they have undergone the expected RMCE process without unwanted rearrangements or deletions. Clones that have the expected genomic structure are selected for further use.

ES cell clones carrying the partly canine immunoglobulin heavy chain DNA (813) in the mouse heavy chain locus are microinjected into mouse blastocysts from strain DBA/2 to create partially ES cell-derived chimeric mice according to standard procedures. Male chimeric mice with the highest levels of ES cell-derived contribution to their coats are selected for mating to female mice. The female mice of choice here are of C57Bl/6NTac strain, and also carry a transgene encoding the Flp recombinase that is expressed in their germline. Offspring from these matings are analyzed for the presence of the partly canine immunoglobulin heavy chain locus, and for loss of the FRT-flanked neomycin resistance gene that was created in the RMCE step. Mice that carry the partly canine locus are used to establish a colony of mice.

Example 4

Figure 9:
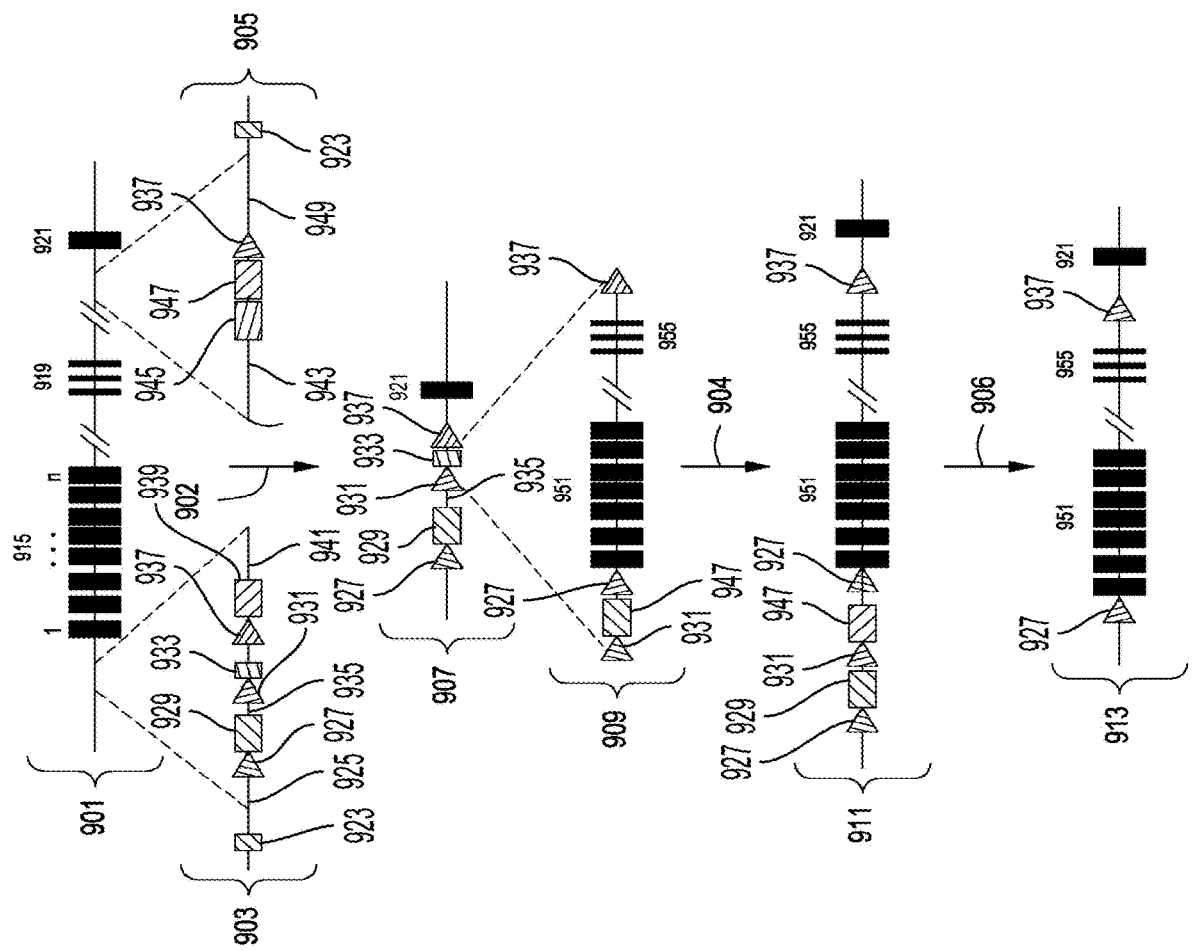
FIG. 9 is a schematic diagram illustrating the introduction of an engineered partly canine immunoglobulin κL chain variable region gene locus into the endogenous immunoglobulin κL chain locus of the mouse genome.

Introduction of an Engineered Partly Canine Immunoglobulin Locus into the Immunoglobulin Kappa Chain Gene Locus of a Mouse Genome Another method for replacing a portion of a mouse genome with partly canine immunoglobulin locus is illustrated in FIG. 9. This method provides introducing a first site-specific recombinase recognition sequence into the mouse genome, which may be introduced either 5' or 3' of the cluster of endogenous $V_K$ (915) and $J_K$ (919) region gene segments of the mouse genome, followed by the introduction of a second site-specific recombinase recognition sequence into the mouse genome, which in combination with the first sequence-specific recombination site flanks the entire locus comprising clusters of $V_K$ and $J_K$ gene segments upstream of the constant region genes (921). The flanked region is deleted and then replaced with a partly canine immunoglobulin locus using the relevant site-specific recombinase, as described herein.

The targeting vectors employed for introducing the site-specific recombination sequences on either side of the $V_K$ (915) and $J_K$ (919) gene segments also include an additional site-specific recombination sequence that has been modified so that it is still recognized efficiently by the recombinase, but does not recombine with unmodified sites. This site is positioned in the targeting vector such that after deletion of the $V_K$ and $J_K$ gene segment clusters it can be used for a second site specific recombination event in which a non-native piece of DNA is moved into the modified $V_K$ locus via RMCE. In this example, the non-native DNA is a synthetic nucleic acid comprising both canine and mouse Igκ variable region gene sequences.

Two gene targeting vectors are constructed to accomplish the process just outlined. One of the vectors (903) comprises mouse genomic DNA taken from the 5' end of the locus, upstream of the most distal $V_K$ gene segment. The other vector (905) comprises mouse genomic DNA taken from within the locus downstream (3') of the $J_K$ gene segments (919) and upstream of the constant region genes (921).

The key features of the 5' vector (903) are as follows: a gene encoding the diphtheria toxin A (DTA) subunit under transcriptional control of a modified herpes simplex virus type I thymidine kinase gene promoter coupled to two mutant transcriptional enhancers from the polyoma virus (923); 6 Kb of mouse genomic DNA (925) mapping upstream of the most distal variable region gene in the kappa chain locus; a FRT recognition sequence for the Flp recombinase (927); a piece of genomic DNA containing the mouse Polr2a gene promoter (929); a translation initiation sequence (935, methionine codon embedded in a "Kozak" consensus sequence); a mutated loxP recognition sequence (lox5171) for the Cre recombinase (931); a transcription termination/polyadenylation sequence (933); a loxP recognition sequence for the Cre recombinase (937); a gene encoding a fusion protein comprised of a protein conferring resistance to puromycin fused to a truncated form of the thymidine kinase (pu-TK) under transcriptional control of the promoter from the mouse phosphoglycerate kinase 1 gene (939); 2.5 Kb of mouse genomic DNA (941) mapping close to the 6 Kb sequence at the 5' end in the vector and arranged in the native relative orientation.

The key features of the 3' vector (905) are as follows: 6 Kb of mouse genomic DNA (943) mapping within the intron between the $J_K$ (919) and $C_K$ (921) gene loci; a gene encoding the human hypoxanthine-guanine phosphoribosyl transferase (HPRT) under transcriptional control of the mouse Polr2a gene promoter (945); a neomycin resistance gene under the control of the mouse phosphoglycerate kinase 1 gene promoter (947); a loxP recognition sequence for the Cre recombinase (937); 3.6 Kb of mouse genomic DNA (949) that maps immediately downstream in the genome of the 6 Kb DNA fragment included at the 5' end in the vector, with the two fragments oriented in the same relative way as in the mouse genome; a gene encoding the diphtheria toxin A (DTA) subunit under transcriptional control of a modified herpes simplex virus type I thymidine kinase gene promoter coupled to two mutant transcriptional enhancers from the polyoma virus (923).

Mouse embryonic stem (ES) cells derived from C57Bl/6NTac mice are transfected by electroporation with the 3' vector (905) according to widely used procedures. Prior to electroporation, the vector DNA is linearized with a rare-cutting restriction enzyme that cuts only in the prokaryotic plasmid sequence or the polylinker associated with it. The transfected cells are plated and after ~24 hours they are placed under positive selection for cells that have integrated the 3' vector into their DNA by using the neomycin analogue drug G418. There is also negative selection for cells that have integrated the vector into their DNA but not by homologous recombination. Non-homologous recombination will result in retention of the DTA gene, which will kill the cells when the gene is expressed, whereas the DTA gene is deleted by homologous recombination since it lies outside of the region of vector homology with the mouse Igκ locus. Colonies of drug-resistant ES cells are physically extracted from their plates after they became visible to the naked eye about a week later. These picked colonies are disaggregated, re-plated in micro-well plates, and cultured for several days. Thereafter, each of the clones of cells is divided such that some of the cells could be frozen as an archive, and the rest used for isolation of DNA for analytical purposes.

DNA from the ES cell clones is screened by PCR using a widely used gene-targeting assay design. For this assay, one of the PCR oligonucleotide primer sequences maps outside the region of identity shared between the 3' vector (905) and the genomic DNA (901), while the other maps within the novel DNA between the two arms of genomic identity in the vector, i.e., in the HPRT (945) or neomycin resistance (947) genes. According to the standard design, these assays detect pieces of DNA that are only present in clones of ES cells derived from transfected cells that had undergone fully legitimate homologous recombination between the 3' vector (905) and the endogenous mouse Igκ locus. Two separate transfections are performed with the 3' vector (905). PCR-positive clones from the two transfections are selected for expansion followed by further analysis using Southern blot assays.

The Southern blot assays are performed according to widely used procedures; they involve three probes and genomic DNA digested with multiple restriction enzymes chosen so that the combination of probes and digests allowed for conclusions to be drawn about the structure of the targeted locus in the clones and whether it is properly modified by homologous recombination. One of the probes maps to DNA sequence flanking the 5' side of the region of identity shared between the 3' kappa targeting vector (905) and the genomic DNA; a second probe also maps outside the region of identity but on the 3' side; the third probe maps within the novel DNA between the two arms of genomic identity in the vector, i.e., in the HPRT (945) or neomycin resistance (947) genes. The Southern blot identifies the presence of the expected restriction enzyme-generated fragment of DNA corresponding to the correctly mutated, i.e., by homologous recombination with the 3' kappa targeting vector (905) part of the kappa locus, as detected by one of the external probes and by the neomycin resistance or HPRT gene probe. The external probe detects the mutant fragment and also a wild-type fragment from the non-mutant copy of the immunoglobulin kappa locus on the homologous chromosome.

Karyotypes of PCR- and Southern blot-positive clones of ES cells are analyzed using an in situ fluorescence hybridization procedure designed to distinguish the most commonly arising chromosomal aberrations that arise in mouse ES cells. Clones with such aberrations are excluded from further use. Karyoptypically normal clones that are judged to have the expected correct genomic structure based on the Southern blot data are selected for further use.

Acceptable clones are then modified with the 5' vector (903) using procedures and screening assays that are essentially identical in design to those used with the 3' vector (905), except that puromycin selection is used instead of G418/neomycin selection, and the protocols are tailored to match the genomic region modified by the 5' vector (903). The goal of the 5' vector (903) transfection experiments is to isolate clones of ES cells that have been mutated in the expected fashion by both the 3' vector (905) and the 5' vector (903), i.e., doubly targeted cells carrying both engineered mutations. In these clones, the Cre recombinase causes a recombination (902) to occur between the loxP sites introduced into the kappa locus by the two vectors, resulting in the genomic DNA configuration shown at 907.

Further, the clones must have undergone gene targeting on the same chromosome, as opposed to homologous chromosomes; i.e., the engineered mutations created by the targeting vectors must be in cis on the same DNA strand rather than in trans on separate homologous DNA strands. Clones with the cis arrangement are distinguished from those with the trans arrangement by analytical procedures such as fluorescence in situ hybridization of metaphase spreads using probes that hybridize to the novel DNA present in the two gene targeting vectors (903 and 905) between their arms of genomic identity. The two types of clones can also be distinguished from one another by transfecting them with a vector expressing the Cre recombinase, which deletes the pu-Tk (939), HPRT (945) and neomycin resistance (947) genes if the targeting vectors have been integrated in cis, and comparing the number of colonies that survive ganciclovir selection against the thymidine kinase gene introduced by the 5' vector (903) and by analyzing the drug resistance phenotype of the surviving clones by a "sibling selection" screening procedure in which some of the cells from the clone are tested for resistance to puromycin or G418/neomycin. Cells with the cis arrangement of mutations are expected to yield approximately $10^3$ more ganciclovir-resistant clones than cells with the trans arrangement. The majority of the resulting cis-derived ganciclovir-resistant clones should also be sensitive to both puromycin and G418/neomycin, in contrast to the trans-derived ganciclovir-resistant clones, which should retain resistance to both drugs. Clones of cells with the cis-arrangement of engineered mutations in the kappa chain locus are selected for further use.

The doubly targeted clones of cells are transiently transfected with a vector expressing the Cre recombinase (902) and the transfected cells are subsequently placed under ganciclovir selection, as in the analytical experiment summarized above. Ganciclovir-resistant clones of cells are isolated and analyzed by PCR and Southern blot for the presence of the expected deletion (907) between the two engineered mutations created by the 5' vector (903) and the 3' vector (905). In these clones, the Cre recombinase has caused a recombination to occur between the loxP sites (937) introduced into the kappa chain locus by the two vectors. Because the loxP sites are arranged in the same relative orientations in the two vectors, recombination results in excision of a circle of DNA comprising the entire genomic interval between the two loxP sites. The circle does not contain an origin of replication and thus is not replicated during mitosis and is therefore lost from the clones of cells as they undergo clonal expansion. The resulting clones carry a deletion of the DNA that was originally between the two loxP sites. Clones that have the expected deletion are selected for further use.

The ES cell clones carrying the deletion of sequence in one of the two homologous copies of their immunoglobulin kappa chain locus are retransfected (904) with a Cre recombinase expression vector together with a piece of DNA (909) comprising a partly canine immunoglobulin kappa chain locus containing Vκ (951) and Jκ (955) gene segments. The key features of this piece of DNA (referred to as "K-K") are the following: a lox5171 site (931); a neomycin resistance gene open reading frame (947, lacking the initiator methionine codon, but in-frame and contiguous with an uninterrupted open reading frame in the lox5171 site (931)); a FRT site (927); an array of 19 functional canine Vκ gene segments (951), each comprised of canine coding sequences embedded in mouse noncoding sequences; optionally a 13.5 Kb piece of genomic DNA from immediately upstream of the cluster of J kappa region gene segments in the mouse kappa chain locus (not shown); a 2 Kb piece of DNA containing the 5 canine Jκ region gene segments (955) embedded in mouse noncoding DNA; a loxP site (937) in opposite relative orientation to the lox5171 site (931).

The sequences of the canine Vκ and Jκ gene coding regions are in Table 2.

In a second independent experiment, an alternative piece of partly canine DNA (909) is used in place of the K-K DNA. The key features of this DNA (referred to as "L-K") are the following: a lox5171 site (931); a neomycin resistance gene open reading frame (947) lacking the initiator methionine codon, but in-frame and contiguous with an uninterrupted open reading frame in the lox5171 site (931); a FRT site (927); an array of 7 functional canine V$_\lambda$ variable region gene segments (951), each comprised of canine coding sequences embedded in mouse noncoding regulatory or scaffold sequences; optionally, a 13.5 Kb piece of genomic DNA from immediately upstream of the cluster of the J region gene segments in the mouse kappa chain locus (not shown); a 2 Kb piece of DNA containing five canine Jλ region gene segments embedded in mouse noncoding DNA (955); a loxP site (937) in opposite relative orientation to the lox5171 site (931).

The transfected clones from the K-K and L-K transfection experiments are placed under G418 selection, which enriches for clones of cells that have undergone RMCE, in which the partly canine donor DNA (909) is integrated in its entirety into the deleted immunoglobulin kappa chain locus between the lox5171 (931) and loxP (937) sites that were placed there by 5' (903) and 3' (905) vectors, respectively. Only cells that have properly undergone RMCE have the capability to express the neomycin resistance gene (947) because the promoter (929) as well as the initiator methionine codon (935) required for its expression are not present in the vector (909) and are already pre-existing in the host cell Igh locus (907). The DNA region created using the K-K sequence is illustrated at 911. The remaining elements from the 5' vector (903) are removed via Flp-mediated recombination (906) in vitro or in vivo, resulting in the final canine-based light chain locus as shown at 913.

G418-resistant ES cell clones are analyzed by PCR and Southern blotting to determine if they have undergone the expected RMCE process without unwanted rearrangements or deletions. Both K-K and L-K clones that have the expected genomic structure are selected for further use.

The K-K ES cell clones and the L-K ES cell clones carrying the partly canine immunoglobulin DNA in the mouse kappa chain locus (913) are microinjected into mouse blastocysts from strain DBA/2 to create partly ES cell-derived chimeric mice according to standard procedures. Male chimeric mice with the highest levels of ES cell-derived contribution to their coats are selected for mating to female mice. The female mice of choice for use in the mating are of the C57Bl/6NTac strain, and also carry a transgene encoding the Flp recombinase that is expressed in their germline. Offspring from these matings are analyzed for the presence of the partly canine immunoglobulin kappa or lambda light chain locus, and for loss of the FRT-flanked neomycin resistance gene that was created in the RMCE step. Mice that carry the partly canine locus are used to establish colonies of K-K and L-K mice.

Mice carrying the partly canine heavy chain locus, produced as described in Example 3, can be bred with mice carrying a canine-based kappa chain locus. Their offspring are in turn bred together in a scheme that ultimately produces mice that are homozygous for both canine-based loci, i.e., canine-based for heavy chain and kappa. Such mice produce partly canine heavy chains comprised of canine variable domains and mouse constant domains. They also produce partly canine kappa proteins comprised of canine kappa variable domains and the mouse kappa constant domain from their kappa loci. Monoclonal antibodies recovered from these mice are comprised of canine heavy chain variable domains paired with canine kappa variable domains.

A variation on the breeding scheme involves generating mice that are homozygous for the canine-based heavy chain locus, but heterozygous at the kappa locus such that on one chromosome they have the K-K canine-based locus and on the other chromosome they have the L-K canine-based locus. Such mice produce partly canine heavy chains comprised of canine variable domains and mouse constant domains. They also produce partly canine kappa proteins comprised of canine kappa variable domains and the mouse kappa constant domain from one of their kappa loci. From the other kappa locus, they will produce partly canine lambda proteins comprised of canine lambda variable domains the mouse kappa constant domain. Monoclonal antibodies recovered from these mice are comprised of canine variable domains paired in some cases with canine kappa variable domains and in other cases with canine lambda variable domains.

Example 5

Figure 10:
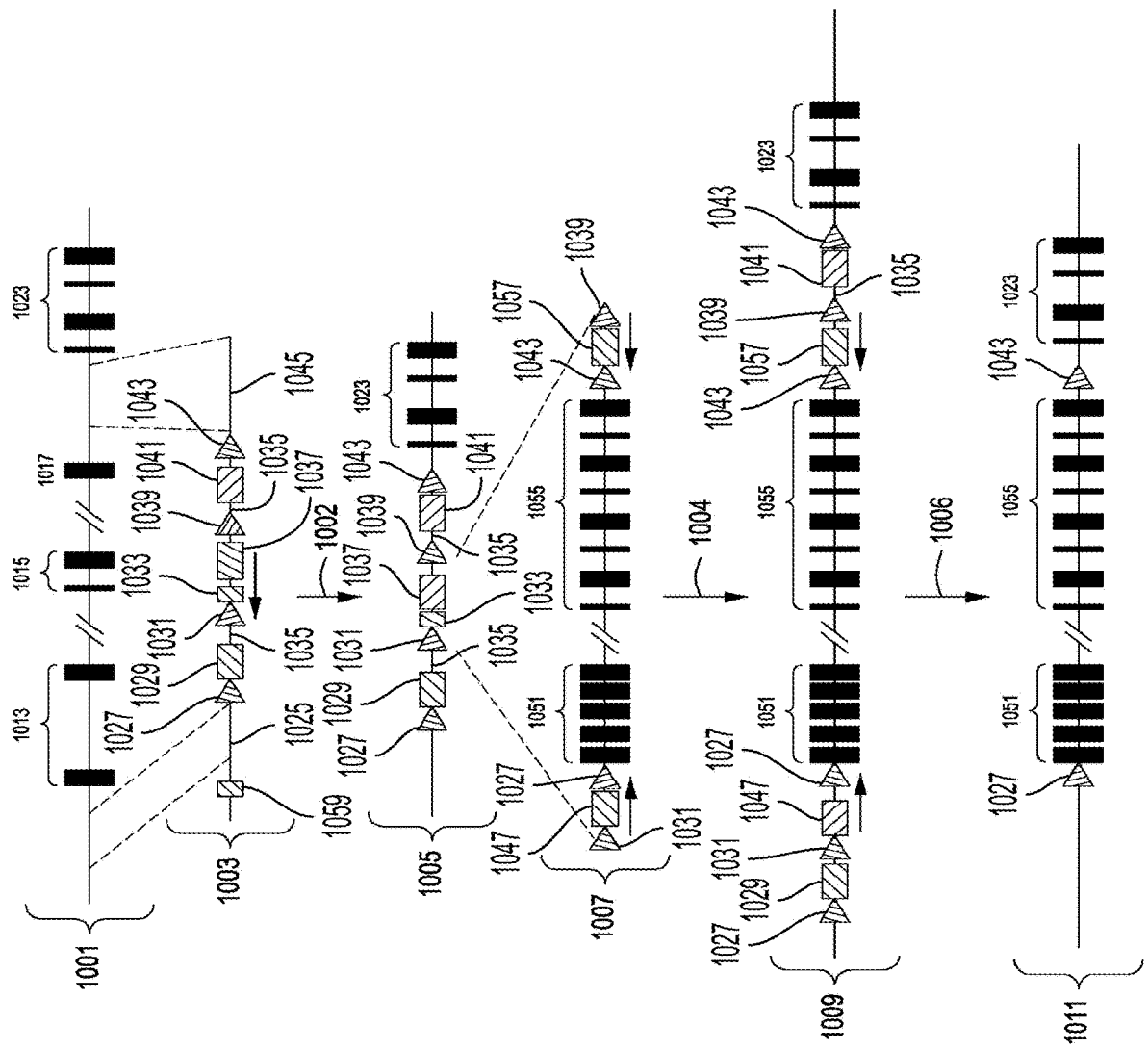
FIG. 10 is a schematic diagram illustrating the introduction of an engineered partly canine immunoglobulin λL chain variable region gene locus into the endogenous immunoglobulin λL chain locus of the mouse genome.

Introduction of an Engineered Partly Canine Immunoglobulin Locus into the Immunoglobulin Lambda Chain Gene Locus of a Mouse Genome Another method for replacing a portion of a mouse genome with an engineered partly canine immunoglobulin locus is illustrated in FIG. 10. This method comprises deleting approximately 194 Kb of DNA from the wild-type mouse immunoglobulin lambda locus (1001)—comprising Vλx/Vλ2 gene segments (1013), Jλ2/Cλ2 gene cluster (1015), and Vλ1 gene segment (1017)—by a homologous recombination process involving a targeting vector (1003) that shares identity with the locus both upstream of the Vλx/Vλ2 gene segments (1013) and downstream of the Vλ1 gene segment (1017) in the immediate vicinity of the J3, C3, J1 and C1 lambda gene cluster (1023). The vector replaces the 194 Kb of DNA with elements designed to permit a subsequent site-specific recombination in which a non-native piece of DNA is moved into the modified Vλ locus via RMCE (1004). In this example, the non-native DNA is a synthetic nucleic acid comprising both canine and mouse sequences.

The key features of the gene targeting vector (1003) for accomplishing the 194 Kb deletion are as follows: a negative selection gene such as a gene encoding the A subunit of the diphtheria toxin (DTA, 1059) or a herpes simplex virus thymidine kinase gene (not shown); 4 Kb of genomic DNA from 5' of the mouse Vλx/Vλ2 variable region gene segments in the lambda locus (1025); a FRT site (1027); a piece of genomic DNA containing the mouse Polr2a gene promoter (1029); a translation initiation sequence (methionine codon embedded in a "Kozak" consensus sequence) (1035); a mutated loxP recognition sequence (lox5171) for the Cre recombinase; a transcription termination/polyadenylation sequence (1033); an open reading frame encoding a protein that confers resistance to puromycin (1037), whereas this open reading frame is on the antisense strand relative to the Polr2a promoter and the translation initiation sequence next to it and is followed by its own transcription termination/polyadenylation sequence (1033); a loxP recognition sequence for the Cre recombinase (1039); a translation initiation sequence (a methionine codon embedded in a "Kozak" consensus sequence) (1035) on the same, antisense strand as the puromycin resistance gene open reading frame; a chicken beta actin promoter and cytomegalovirus early enhancer element (1041) oriented such that it directs transcription of the puromycin resistance open reading frame, with translation initiating at the initiation codon downstream of the loxP site and continuing back through the loxP site into the puromycin open reading frame all on the antisense strand relative to the Polr2a promoter and the translation initiation sequence next to it; a mutated recognition site for the Flp recombinase known as an "F3" site (1043); a piece of genomic DNA upstream of the J3, C3, J1 and C1 lambda gene segments (1045).

Mouse embryonic stem (ES) cells derived from C57Bl/6NTac mice are transfected (1002) by electroporation with the targeting vector (1003) according to widely used procedures. Homologous recombination replaces the native DNA with the sequences from the targeting vector (1003) in the 196 Kb region resulting in the genomic DNA configuration depicted at 1005.

Prior to electroporation, the vector DNA is linearized with a rare-cutting restriction enzyme that cuts only in the prokaryotic plasmid sequence or the polylinker associated with it. The transfected cells are plated and after ~24 hours placed under positive drug selection using puromycin. There is also negative selection for cells that have integrated the vector into their DNA but not by homologous recombination. Non-homologous recombination will result in retention of the DTA genes, which will kill the cells when the genes are expressed, whereas the DTA genes are deleted by homologous recombination since they lie outside of the region of vector homology with the mouse Igl locus. Colonies of drug-resistant ES cells are physically extracted from their plates after they became visible to the naked eye over a week later. These picked colonies are disaggregated, re-plated in micro-well plates, and cultured for several days. Thereafter, each of the clones of cells are divided such that some of the cells are frozen as an archive, and the rest used for isolation of DNA for analytical purposes.

DNA from the ES cell clones is screened by PCR using a widely used gene-targeting assay design. For these assays, one of the PCR oligonucleotide primer sequences maps outside the regions of identity shared between the targeting vector and the genomic DNA, while the other maps within the novel DNA between the two arms of genomic identity in the vector, e.g., in the puro gene (1037). According to the standard design, these assays detect pieces of DNA that would only be present in clones of cells derived from transfected cells that had undergone fully legitimate homologous recombination between the targeting vector (1003) and the native DNA (1001).

Six PCR-positive clones from the transfection (1002) are selected for expansion followed by further analysis using Southern blot assays. The Southern blots involve three probes and genomic DNA from the clones that has been digested with multiple restriction enzymes chosen so that the combination of probes and digests allow identification of whether the ES cell DNA has been properly modified by homologous recombination.

Karyotypes of the six PCR- and Southern blot-positive clones of ES cells are analyzed using an in situ fluorescence hybridization procedure designed to distinguish the most commonly arising chromosomal aberrations that arise in mouse ES cells. Clones that show evidence of aberrations are excluded from further use. Karyoptypically normal clones that are judged to have the expected correct genomic structure based on the Southern blot data are selected for further use.

The ES cell clones carrying the deletion in one of the two homologous copies of their immunoglobulin lambda chain locus are retransfected (1004) with a Cre recombinase expression vector together with a piece of DNA (1007) comprising a partly canine immunoglobulin lambda chain locus containing V, J and C region gene segments. The key features of this piece of DNA (1007) are as follows: a lox5171 site (1031); a neomycin resistance gene open reading frame lacking the initiator methionine codon, but in-frame and contiguous with an uninterrupted open reading frame in the lox5171 site (1047); a FRT site (1027); an array of 7 functional canine lambda variable region gene segments, each comprised of canine lambda coding sequences embedded in mouse lambda noncoding sequences (1051); an array of J-C units where each unit is comprised of a canine Jλ gene segment and a mouse lambda constant domain gene segment embedded within noncoding sequences from the mouse lambda locus (1055) (the canine Jλ gene segments are those encoding Jλ1, Jλ2, Jλ6 and Jλ7, while the mouse lambda constant domain gene segments are C1 and/or C2 and/or C3); a mutated recognition site for the Flp recombinase known as an "F3" site (1043); an open reading frame conferring hygromycin resistance (1057), which is located on the antisense strand relative to the immunoglobulin gene segment coding information in the construct; a loxP site (1039) in opposite relative orientation to the lox5171 site.

The sequences of the canine Vλ and Jλ gene coding regions are in Table 3.

The transfected clones are placed under G418 and/or hygromycin selection, which enriches for clones of cells that have undergone a RMCE process, in which the partly canine donor DNA is integrated in its entirety into the deleted immunoglobulin lambda chain locus between the lox5171 and loxP sites that were placed there by the gene targeting vector. The remaining elements from the targeting vector (1003) are removed via FLP-mediated recombination (1006) in vitro or in vivo resulting in the final caninized locus as shown at 1011.

G418/hygromycin-resistant ES cell clones are analyzed by PCR and Southern blotting to determine if they have undergone the expected recombinase-mediated cassette exchange process without unwanted rearrangements or deletions. Clones that have the expected genomic structure are selected for further use.

The ES cell clones carrying the partly canine immunoglobulin DNA (1011) in the mouse lambda chain locus are microinjected into mouse blastocysts from strain DBA/2 to create partially ES cell-derived chimeric mice according to standard procedures. Male chimeric mice with the highest levels of ES cell-derived contribution to their coats are selected for mating to female mice. The female mice of choice here are of the C57Bl/6NTac strain, which carry a transgene encoding the Flp recombinase expressed in their germline. Offspring from these matings are analyzed for the presence of the partly canine immunoglobulin lambda chain locus, and for loss of the FRT-flanked neomycin resistance gene and the F3-flanked hygromycin resistance gene that were created in the RMCE step. Mice that carry the partly canine locus are used to establish a colony of mice.

In some aspects, the mice comprising the canine-based heavy chain and kappa locus (as described in Examples 3 and 4) are bred to mice that carry the canine-based lambda locus. Mice generated from this type of breeding scheme are homozygous for the canine-based heavy chain locus, and can be homozygous for the K-K canine-based locus or the L-K canine-based locus. Alternatively, they can be heterozygous at the kappa locus carrying the K-K locus on one chromosome and the L-K locus on the other chromosome. Each of these mouse strains is homozygous for the canine-based lambda locus. Monoclonal antibodies recovered from these mice are comprised of canine heavy chain variable domains paired in some cases with canine kappa variable domains and in other cases with canine lambda variable domains. The lambda variable domains are derived from either the canine-based L-K locus or the canine-based lambda locus.

Example 6

Figure 11:
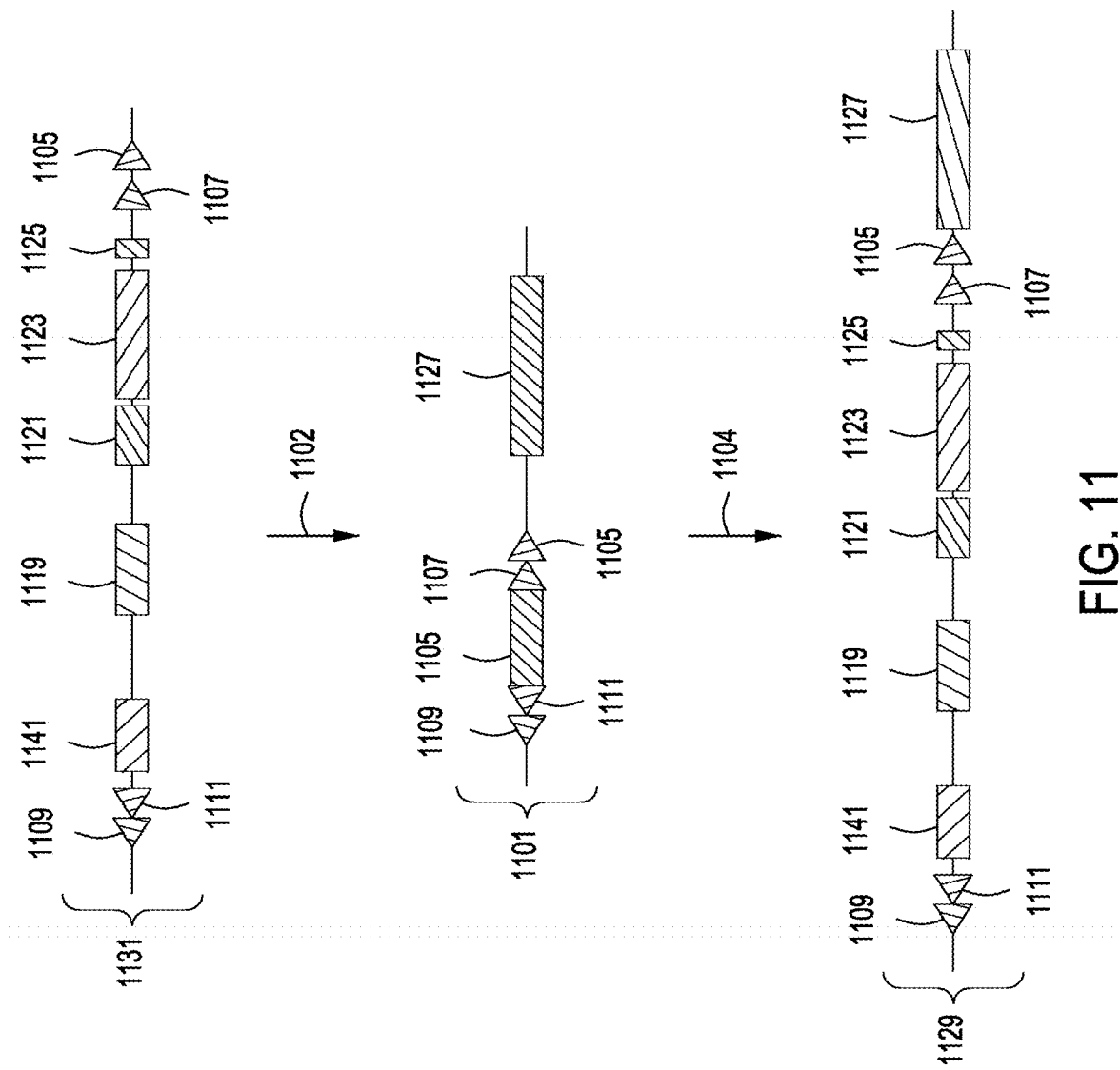
FIG. 11 is a schematic diagram illustrating the introduction of an engineered partly canine immunoglobulin locus comprising a canine $V_H$ minilocus via RMCE.

Introduction of an Engineered Partly Canine Immunoglobulin Minilocus into a Mouse Genome In certain other aspects, the partly canine immunoglobulin locus comprises a canine variable domain minilocus such as the one illustrated in FIG. 11. Here instead of a partly canine immunoglobulin locus comprising all or substantially all of the canine $V_H$ gene segment coding sequences, the mouse immunoglobulin locus is replaced with a minilocus (1119) comprising fewer chimeric canine $V_H$ gene segments, e.g. 1-79 canine $V_H$ gene segments determined to be functional; that is, not pseudogenes.

A site-specific targeting vector (1131) comprising the partly canine immunoglobulin locus to be integrated into the mammalian host genome is introduced (1102) into the genomic region (1101) with the deleted endogenous immunoglobulin locus comprising the puro-TK gene (1105) and the following flanking sequence-specific recombination sites: mutant FRT site (1109), mutant LoxP site (1111), wild-type FRT site (1107), and wild-type LoxP site (1105). The site-specific targeting vector comprises i) an array of optional PAIR elements (1141); ii) a $V_H$ locus (1119) comprising, e.g., 1-47 functional canine $V_H$ coding regions and intervening sequences based on the mouse genome endogenous sequences; iii) a 21.6 kb pre-D region (1121) comprising mouse sequence; iv) a $D_H$ locus (1123) and a $J_H$ locus (1125) comprising 6 $D_H$ and 5 $J_H$ canine coding sequences and intervening sequences based on the mouse genome endogenous sequences. The partly canine immunoglobulin locus is flanked by recombination sites—mutant FRT (1109), mutant LoxP (1111), wild-type FRT (1107), and wild-type LoxP (1105)—that allow recombination with the modified endogenous locus. Upon introduction of the appropriate recombinase, e.g., Cre) (1104), the partly canine immunoglobulin locus is integrated into the genome upstream of the constant gene region (1127) as shown at 1129.

As described in Example 1, the primary screening for introduction of the partly canine immunoglobulin variable region locus is carried out by primary PCR screens supported by secondary Southern blotting assays. The deletion of the puro-TK gene (1105) as part of the recombination event allows identification of the cells that did not undergo the recombination event using ganciclovir negative selection.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims. In the claims that follow, unless the term "means" is used, none of the features or elements recited therein should be construed as means-plus-function limitations pursuant to 35 U.S.C. § 112 ¶6. All references cited herein are incorporated by reference in their entirety for all purposes.

TABLE 1

Canine IgH locus

Germline $V_H$ sequences
(NB, the sequence and annotation of the dog genome is still incomplete. This table does not necessarily describe the complete canine $V_H$, $D_H$ and $J_H$ gene repertoire.)

```
SEQ ID NO. 1 vh1
ccttgcacag taatacactg ccgtgtcctc atctctcagg ctgttcatct gcagatacag    60
cgtgttcttg gcattgtctc tggagatggt gaatcggccc ttcacagcgt ctgcgtagct   120
tgtgctactt ccatcactgc taatttgtga gacccactga agcccttcc ctggagcctg   180
gcggatccag ctcatgtagt tgctactgaa ggtgaatcca gaggccacac aggagagtct   240
cagggacccc ccaggcttca ccaggtctcc cccagactcc accagctgca cctc          294
//

SEQ ID NO. 2 vh2
ctttgcacag taatacaccg ctgtgtcctc agctctcagg ctgttcatct gcagatacag    60
cgtattcttt gcgttgtctc tggagatggt gaatcggccc ttcacagcgt ctgcatagct   120
tgtgctactt ccatctttgt taatgtgtga gacccactga agcccttcc ctggagcctg   180
gcgggcccaa tacatgtagt aactactgaa ggtaaatcca gaggccacac aggagagtct   240
cagggacccc ccaggcttca ccatgtctcc cccagactcc accagctgca cctc          294
//

SEQ ID NO. 3 vh3
ggagtgaaca cagacaaacc accatgaagt tgttgctctg ctgggctttt cttcttgcaa    60
tttaaaaagt aattcatgga gaacaagaga ccttgaatat atgagttgag ttaagtgaga   120
gaaacagggg atgtgggaca gtttcctgac caggatgtct tgtgtctgca ggtgtccagg   180
gtgaggtgca gctggtggag tctggggag acctgatgaa gcctggggg gtccctgaga    240
ctctcctgtg tggcctctga attcatcttc agtggctact ggaagtactg gatccaccaa   300
gctccaggga aggggctgca gtgggtcaca tggattagca atgatggaag tagcaaaagc   360
tatgcagacg ctgtgaaggg ccaattcacc atctccaaag acaatgccaa atacacgctg   420
tatctgcaga tgaacagcct gagagccgag gacatggccg tgtattactg tatga        475
//

SEQ ID NO. 4 vh4 pseudo
aggtgcagct ggtggagtct gggggagacc tgatgaagcc tggggggtc cctgagactc    60
tcctgtgtgg cctctgaatt catcttcagt ggctactgga agtactggat ccaccaagct   120
ccagggaagg ggctgcagtg ggtcacatgg attagcaatg atggaagtag caaaagctat   180
gcagacgctg tgaagggcca attcaccatc tccaaagaca atgccaaata cacgctgtat   240
ctgcagatga acagcctgag agccgaggac atggccgtgt attactgtat ga           292
//

SEQ ID NO. 5 vh5 pseudo
aatctgaggt ccagctggtg cagtctgggg ctgaggtgag gaaaccagtt tcatctgtga    60
aggtctcctg gaaggcatct ggatacacct acatggatgc ttatatgcac tggttatgac   120
aagcttcagg aataaggttt gggtgtatgg gatggattgg tcccaaagat ggtgccacaa   180
gatattcaca gaagttccac agcagagtct ccctgatggc agacatgtcc aaagcacagc   240
ctacatgctg ctgagcagtc agaggcctga ggacacacct gcatattact gtgt          294
//

SEQ ID NO. 6 vh6
actcgcacag taatacacgg ccgtgtcctc ggctctcagg ctgttcatct gaagatacag    60
cgtgttcttg gcgttgtctc tggagatggt gaatcggccc ttcacagcgt ctgcatagct   120
tgtgctactt ccaccactgt taatgtatgc gacccactga agcccttcc ctggagcctg   180
gcggacccag ctcatgtggt agctactgaa ggtgaatcca gaggccacac aggaaagtct   240
cagggacccc ccaggcttca ccaggtctcc cccagactcc accagctgca cctc          294
//

SEQ ID NO. 7 vh7
gtctgcacag taatacacgg ccgtgtcctc ggctctgagg ctgttcatct gcagatagag    60
cgtgttcttg gcgttgtctc tggagatggt gaatcggccc ttcacagcgt ctgcgtagct   120
tgtgctactt ccatcattgc taatgtatgc gacccactga agcccttttc ctggagcctg   180
gcggatccag ctcatgtcgg agctactgaa ggtgaatcca gaggctacac aggagagtct   240
cagggacccc ccaggcttca ccaggtctcc cccagactcc accagctgca cctc          294
//
```

TABLE 1-continued

Canine IgH locus

```
SEQ ID NO. 8 vh8
cctcatgcag taatacacgg ctgtgtcctc ggctctcagg ctgttcatct gcagatacag    60
catgttcttg gtgttgtctc tggagatggt gaatctgtcc ctcaaagtgt ctgcgtagta   120
tgtactactt ccatcatagc taatatgtcc gacccactgc agccccttct tttgagcctg   180
gcggacccag ctcatgccat agctactgaa ggtgaatcca gaggcctgac aggagagacc   240
cagggaaccc ccaggattca ccatgtgtcc tccaaactcc accagttgct cctc          294
//

SEQ ID NO. 9 vh9
actcgcacag taatacacgg ccgtgtcctc ggctctcagg ctgttcatct gcagatacgc    60
catgttcttg gcgttgtctc tggagatggt gaatcggccc tttacagctt ctgcatagta   120
tgtggtactt ccactctcat aaatccttgc gacccactcc agccctttcc ctggagcctg   180
gcggacccag tacatttcgt agttactgaa ggtgaatcca gaggcacac aggagagtct    240
cagggacccc ccaggcttca ccaggtctcc cccagactcc accagctgca cctc          294
//

SEQ ID NO. 10 vh10
ccttgcacag taatacacgg ccgtgtcctc ggctctcagg ctgttcatct gcagatacag    60
cgtgttcttg gcgttgtctc tggagatggt gaatcggccc ttcacagcgt ctgcgtagta   120
tgtgctactt ccactactgc taatttctga gagccactgc agccccttcc ctggagcctg   180
gcggacccag tccatgtcat agctactgaa ggtgaatcca gaggcacac aggaaagtct    240
cagggacccc ccaggcttca ccaggtctcc tccagactcc accagctgca cctc          294
//

SEQ ID NO. 11 vh11
actcacacag taatacacgg ccatgtcctt gtctctcagg ctgttcatct gcagatagag    60
cgtgttcctg gcgttgtctc tggagatggt gaattggccc ttcacagcgt ctgcatacct   120
tgtgctactt ccaccattgc taatgtatgt gacccactgt aacccttcc ctggagcctg    180
gtagacccag tccatgtcgt agctactgaa ggtgaatcca gaggcacac aggaaagtct    240
cagggatccc ccaggcttca ccaggtctcc ctcagtctcc accagctgca cctc          294
//

SEQ ID NO. 12 vh12 pseudo
tttcacacaa taatacacag ccgtgtcctc ggctcccagg ctgttcatct gcagatacag    60
cgtgttcttg gcattgtctc tggagatggt gaatcggccc ttcacagcgt ctgcatagct   120
tgtgctactt ctatcattgg taatacctgc gacccactgc agccccttcc ctggagccta   180
gtggacccag cccatgtagt agctactgaa ggtgaatcta gaggcacac aggagaggga    240
cctccccagg cttcaccacg tctcccctag actccaccag ctgcacctca ccct          294
//

SEQ ID NO. 13 vh13 pseudo
cttcccacag taatacacag ctgtgtcctc ggctctcagg ctgttcatct gcagatacag    60
cgtgttcttg gcattgtctc tggagatggt gaatcggccc ttcacagcgt ctgcatagta   120
tgtgctactt ccaccactgt taatgtatcc gacccactgc agccccttcc ctggagcctg   180
gcggacccag ctcatgtagt agctactgaa ggtgaatcca gaggcacac aggagagtct    240
cagagacccc ccaggcttca ccaggtctcc ccagactcca ccagctgcac ctca          294
//

SEQ ID NO. 14 vh14
cctcatgcag taatacacgg ctgtgtcctc ggctctcagg ctgttcatct gcagatacag    60
catgttcttg gtgttgtctc tggagatggt gaatctgtcc ctcacagtgt ctgtgtagta   120
tgtgctactt ccatcatagc taatatgtcc gacccactgc agccccttct tttgagcctg   180
gcggacccag ctcatgccat agctactgaa ggtgaatcca gaggcctgac aggagagacc   240
cagggaaccc ccaggattca ccatgtgtcc tccaaactcc accagttgct cctc          294
//

SEQ ID NO. 15 vh15 pseudo
actcacacag taatacacgg ccgtgtccta ggctctcagg ctgttcatct gcagatacac    60
catgttcttg gcgttgtctc tggagatggt gaatcggccc tttacagctt ctgcgtagta   120
tgtggtactt ccactctcat aaatccttgc gacccactcc agccctttcc ctggagcctg   180
gtggacccag tacatttcgt agttactgaa ggtgaatcca gaggccacac aggagagtct   240
cagggatccc ccaggcttca ccaggtctcc cccagactcc accatctgca cctc          294
//

SEQ ID NO. 16 vh16
tctcgcacag taataaaggg ctgtgtcctc cactgtcagg ctgttcatct gcagatacag    60
tgtgttcttg gcgttgtctc tggagatggt gaatcggccc ttcacagcgt ctgggtagta   120
tgtgctactt ccatctttgt taatatatcc gacccactga ttgcccttcc ctggtgcctg   180
gcggatccaa acatgtgagt aactactaaa ggtgaatcca gaggccacac aggagagtct   240
cagggacccc ccaggcttca ccaggtctcc tccagactcc accagctgta cctc          294
//
```

TABLE 1-continued

Canine IgH locus

```
SEQ ID NO. 17 vh17
cttcgcacag taatacacgg ctgtgtcctc agttctcagg ctgttcatct gcagatacag      60
cgtgttcttg gcattgtctc tggagatggt gaatcggccc ttcacagcgt ctgtgtaact     120
tgtgctcctt ccatcactgc taatgtatgc gacccactgc agcccttcc ctggagcctg      180
gcggacccag ctcatgtcgt agctactgaa ggtgaagcca gagaccacac aggagagtct     240
cagggacccc tcaggtttca caaggtctcc cccagactcc accagctgca cctc           294
//

SEQ ID NO. 18 vh18
ctttgcacag taatacatgg ccgtgtcctc ggctctcagg ctgttcatct gcagatacac      60
tgtgttcttg gcgttgtctc tggagatggt gaatcggccc ttcacagcgt ctgtgtagta     120
tgtgctactt ccaccgctgt taatacctgc gaccaactgc agcccttcct caggagcctg     180
gcggacccag ctcatgctgt agctactgaa ggtgaatcca gaggccacac aggacagtct     240
cagggacccc gcaggcttca ccaggtctcc cccagactcc accagctgca cctc           294
//

SEQ ID NO. 19 vh19 pseudo
cacctgcaca gtaatacacc gctgtgtcct cactctcagg ctgttcatct gcagatacag      60
tgtgttcttg gcattgtctc tggaggtggt gaatcagccc ttcacagcgt ctgtgtacct     120
agtgctactt ccaccactgt tactgtatgc gactcactgc agcccttttc ctggagcctg     180
gcagacccat cacatgcagt agatactgaa ggtgaatcca gaggacacag aggagagtct     240
caggaccctc caggcttcac caggtatccc ccagactcca ccagctgcac ctca           294
//

SEQ ID NO. 20 vh20 pseudo
actctcacag taatacacgg ccgtgtcctc agctctcaag ctgttcatct gcaggtacag      60
cgtgttcttg gcattgtctc tggagatggt gaatcggccc ttcacagtgt ctgtgtagta     120
tgtgctcctt ccatcttagc taatagctgc gaccaactgt agcccttcc ccaaagcctg      180
gcagacccag ctcatgccat acttactgaa ggtgaatcca gagaccacac aggacagtct     240
gcagacccag ctcatgccat acttactgaa ggtgaatcca gagaccacac aggacagtct     294
//

SEQ ID NO. 21 vh21 pseudo
cctcaatgtg tcactcacat aataatacag ggctctcagg ctgttcatat gcagatacag      60
cgtgttcttg gcattgtctc tggagatggt gaatcacccc ttcacagcat ctgcatagct     120
ttttctgctt ccaccagtat taacccatat gacccactgc agcccttcc ctggagcctg      180
gctgacccag ctcatccagt agctcctgaa ggtgaatcca gaggtcacat aggagagtct     240
aattgatccc ccaggcttca ccaggtctcc cccagactcc actagcttca cctc           294
//

SEQ ID NO. 22 vh22 pseudo
gtctgcacag taatacatgg ccatgtcctc ggctctcagg ctgttcatct gcagatagag      60
cgtgttcttg gcgttgtctc tggagatggt gaatcagccc ttcagagcgt ctacgtagct     120
tgtgctactt ccatctgtgc taatacctgc gacccactgc agcccttcc ccggagtttg      180
gtggatccag tacatccagt agctactgaa ggtgaatcca gaggccacac aggaggtctc     240
agggatcctg caggcttcat cagttctccc ccagactcca tcatctgcac ctca           294
//

SEQ ID NO. 23 vh23
cttcgcacag gaatacacgg ctgtgtcctc ggctctcagg ctgttcatct gcagatacag      60
cgtgttcttg gcattgtctc tggagatggt gaatcggccc ttcacagcgt ctgcatacct     120
tgtgctactt ccatcatacc taatcaatga dacccctgc agcccttcc ctggagcctg       180
gcggacccag ctcatgccgt agctactgaa ggtgaatcca gaggccacac aggacagtct     240
cagggatccc ccaggcttct ccaggtctcc cccagactcc accagctgca cctc           294
//

SEQ ID NO. 24 vh24
ccttgcacaa taatatacgg ccatgtcctc ggctctcagg ctgttcatct gcagatacag      60
catgttcttg gcattgtctc tggagatggt gaatcggccc ttcacaatgt ctgcgtagct     120
tgtgctactt ccactactgc taatttctgc aacccactgt agcccttcc ttggagcctg      180
gcagaaccag ctcatgtaga agctactgaa ggtgaatcca gaggccacac aggagagtct     240
cagggacccc tcaggcttca caaggtctcc cccagactcc accagctgca cctc           294
//

SEQ ID NO. 25 vh25
cttcacacag taatacacgg ccgtgtcctc ggatctcagg ctgttcatct gcagatacag      60
cgtgttcttg acattgtctc tggagatggt gaattcaccc ttcacagcat ctgtgtagct     120
tgtgctactt ccaccgctgt taaaacctgc gacccactgc atcccttcc ctggaggctg      180
gtgagcccag cccatgttgt agctactgaa ggtgaatcca ggaccacac aggagagtct      240
cagggacgcc ccaggcttca ccagttctcc cccaggctcc accagctgca cctc           294
//
```

TABLE 1-continued

Canine IgH locus

SEQ ID NO. 26 vh26
```
ccttgcacag taatacatgg ccgtgtcctc ggctctcagg ctgttcatct gcagatacag   60
cgtgttcttg gcattgtctc tggagatgat gaatcggccc ttcacagcgt ctgcatagtt  120
tgtgctactt ccactaccgc taatttctgc aacccactgt agcccttcc ctggagcctg   180
gcggacccag ctcatccagt agctactgaa ggtgaatcca gagcccacac aggagagtct  240
cagggacccc ccaggcttca ccaggtctcc cccagactcc accagctaca cctc         294
//
```

SEQ ID NO. 27 vh27 pseudo
```
gcacagtaat acacggccgt gtcctccctc ggctctcagg ctgttcttct acagatacag   60
tgtgttttg gcattgtctc tggagatggt gaatcggccc ttcagagcgt ctgcgtagct  120
tgtgctactt ccatcatatc taatacctgc accccctgt agcccatcc gggagcctc     180
acgggcccac cacatgctgt agctactgaa ggtgaatcca gagcccacac aggagagtct  240
cagggacctc ctaggcttca ccacgtctcc cgcagactcc accagatgca cctt         294
//
```

SEQ ID NO. 28 vh28 pseudo
```
cctcacacag taatacacgg ccgtgtcctc ggctctcagg ctgttcatct gcagatacag   60
cgtgttcttg gcgttgtctc tagaaacagt gaatcggcct ttcacagctt ctgcgtagct  120
tgtgctactt ccatcatacc taatccatgc gacccatgga gcccttccc tggagcctgg   180
tggacccagt acatccagta gctactgaag gtgaatccag agcccacaca ggagactctc  240
agggaccccc ccagacttca ccaggtctcc cccagactcc actagctgca cctc         294
//
```

SEQ ID NO. 29 vh29 pseudo
```
cctcacacag taatacaggg ccgtgtcatc ggctcccagg ctgctcatct gtagatacag   60
cgtgttcttg gtgttgtctc tggagatggt aaatcggccc tttactgtgt ctgcgtgatt  120
tgtgctactt ccactattgc taatagttgt gatccactgc agcccttcc ttggagcctg   180
gcggacccag atcatgctgt agttactgaa ggtgaatccg gaagcacac aggagacagg    240
agagtctcag gaaacctcca gtcttcacca ggtctcccca ggactccacc agct         294
//
```

SEQ ID NO. 30 vh30
```
cttcgcacag taatacacgg ccgtgtcctc ggctctcagg ctgttcatct gcaaatacag   60
cgagttcttg acgttgtctc tggagatggt gaatcggccc ttcacagcgt cagtgtagta  120
tgtgctacct ccactgtcac taatatctgc gacccactgc agcccttcc caggagcctg   180
gcggatccag ctcatgtagt agctactgaa ggtgaatcca gaggcacac aggagagtct   240
cagggacccc ccaggcttca ccagttctcc cccagactcc accagctgca cctc         294
//
```

SEQ ID NO. 31 vh31
```
acccgcacag taatacacgg cggtgtcctc ggctctcagg ctgttcatct gcagatatag   60
cgtgttcttg acgttgtctc tggagatgat gaatcgaccc ttcacagcat ctgcggagct  120
tgtgctactt ccaccactgt taatgtatgc gacccactgc acccccttcc ctggagcctg  180
acagacccat tgcatgctgt agctactgaa ggtgaatcca taggcacac aggagagtgt   240
cagggacccc ccaggcttca ccaggtctcc cccagactcc accagctgca cccc         294
//
```

SEQ ID NO. 32 vh32
```
tcccacacag taatatacgg ccgtgtcctc ggctctcagg cagttcatct gcagatacag   60
cgtgttcttg gcattgtctc tggagatggt gaatcggccc ttcacagcgt ctgcatagta  120
tgtgctactt ccaccactgt taatgtatgc aacccactgc aacccttcc ctggagcctg   180
gccgacccag ctcatccaat agctactgaa ggtaaatcca gaggccacac agaagagtct  240
cagggacccc ccaagcttca ccaggtctcc cccagcctcc accagctgca tctc         294
//
```

SEQ ID NO. 33 vh33
```
acccgcacag taatacacgg ccgtgtcctc ggctctcagg ctgttcatct gaagatacag   60
cgtgttcttg gcgttgtctc tggagatggt gaaccggccc ttcacagcat ctgcatagta  120
tgtgctactt ccaccactgc taatgtatgc gacccactgc agcccttcc ctggagcctg   180
gcggacccag ttcatgtcat agctactgaa ggtgaatcca gaggcacac aggagagtct   240
cagggatccc acaggcttca ccaggtctcc cccagactcc accagctgca cctc         294
//
```

SEQ ID NO. 34 vh34
```
attcacacag taatacatgg ccatgtcctc agctctcagg ctgttcatct gcagatacag   60
catgttcttg gcattgtctc tggagatggt gaatcggccc ttcacagcgt ctgcatagct  120
catgttactt ccactagaat aaattcatgc gactcacggc agcccttcc caggagcctt   180
gtggacccag ctcatggtat aggaaatgaa ggtgaatcca gaggccacac gggcgagtct  240
cagggacctc tcaggcttca ccaggtctcc cccagactcc gccagctgcc cctc         294
//
```

TABLE 1-continued

Canine IgH locus

SEQ ID NO. 35 vh35 pseudo
```
attcacacag taatacatgg ccatgtcctc agctctcagg ctgttcatct gcagatacag      60
catgttcttg gcattgtctc tggagatggt gaatcggccc ttcacagcgt ctgcatagct     120
catgttactt ccactagaat aaattcatgc gactcacggc agcccttcc caggagcctt     180
gtggacccag ctcatggtat aggaaatgaa ggtgaatcca gaggccacac gggcgagtct     240
cagggacctc tcaggcttca ccaggtctcc cccagactcc gccagctgcc cctc           294
//
```

SEQ ID NO. 36 vh36
```
gtctgcacag taatatatgg ccgtgtcctc ggctctcagg ctgttcatct gcagatacag      60
cgtgttcttg acattgtctc tggagatggt gaatcggccc ttcacagtgt ctgcatacct     120
tgagatactt ccatcatacc taatccatga acccactgc agcccctgcc ctggagcctg     180
gtggacccag ctcatttcac tgctactgaa ggtgaatcca gaggccacac aggagagtct     240
cagggaccct ccaggcttca ccaaatcttc cccagactcc accagctgta cctc           294
//
```

SEQ ID NO. 37 vh37
```
cttcgcacag taatacacgg ccgtgtcctc ggctctcagg ctgttcatct gcagatacag      60
cgtgttcttg gcgttgtctc tggagatggt gaatcggccc ttcacagcgt ctgcgtagta    120
tgtgctactt ccatcattcc aaataactgc gacccactgc agcccttcc ctggagactg     180
acggacccag ctcatgtcat agctactaaa ggtgaatcca gaggccacac aggacagtct    240
caaggtcccc ccaggcttca ccaggtctcc cccagactcc accagctgca cctc           294
//
```

SEQ ID NO. 38 vh38
```
cttcgcacag taatacacgg ctgtgtcctc ggctctcagg ctgttcatct gaagatacag      60
cttgttcttg gcgttctctc tggagatggt gaaccggccc ttcacagcgt ctgcgtagcc    120
tgtgctacct ccactatcac taatatctgc gacccactgc agcccttcc caggagcctg     180
gcggatccag ctcatgtagt agctactgaa ggtgaatccc gaggccacac aggagagtct    240
cagggaaccc ccaggcttca cgaggtctcc cccagattcc accagctgta cctc           294
//
```

SEQ ID NO. 39 vh39
```
cttcgcacag taatacacag ccgtgtcctc ggctctcagg ctgttcatct gcagatacac      60
tgtgttcctg gcgttgtctc tggagatggt gaatcggccc ttcacagcgt cagtgtagta    120
tgtgctactt ccatcatagc taatagctgc gacccactgc agcccttcc caggagcctg     180
gcggacccag ctcatgtcgt agttactgaa ggtgaatcca gaggctacac aggagagtct    240
cagggacccc ccaggcttca ccaggtctcc cccagactcc accagctgca cctc           294
//
```

SEQ ID NO. 40 vh40
```
cttcccacag taatacacag caatatcctc agctctcagg ctgttcatct gcagatacac      60
catgttcttg gcgttgtcta tggagatggt gaatcggccc ttcacagcat ctacgtagta    120
tgtgctactt ccactactgc taatagctgc aacccactgc aggcccttcc ctggagcctg    180
gccgacccag ctcatggcat acctactgaa ggtgaatcca gaggtcacac aggagagtct    240
cagggacccc cctggcttca ccaggtcttc ccccagactc caccagctgc actt          294
//
```

SEQ ID NO. 41 vh41 pseudo
```
actcgcacag taatacacgg ccgtgtcctc agctctcaag ctgttcatct gcaggtacag      60
cgtgttcttg ccattgtctc tggagatggt gaatcggccc ttcacagtgt ctgtgtagta    120
tgtgctcctt ccatcatagc taatagctgc gacccactgc agcccttcc ctgaagcctg     180
gcagacccag ctcatgccat agctcctgaa ggtgaatcca gaggccacac aggacagtct    240
cagggaaccc ccaggcttca tcaggtctcc cccagactcc accagctaca cctt          294
//
```

SEQ ID NO. 42 vh42
```
cctcgcacag taatacacgg ccgtgtcttc ggctctcagg ttgttcatct gcagatacag      60
cgtgttcttg gcgttgtctc tggagatggt gaatcgaccc ttcacagcgt ctgtgtacca    120
tgtgctactt ccaccactgt taatgtacgc gacccactgc agtccttcc ctggagcctg     180
gcggacacag ctcatccaat agctactgaa ggtgaatcca gaagtcacac atgagagtct    240
cagggaaccc ccaggcttca ccaggtctcc cccagactcc accagctgca cctc          294
//
```

SEQ ID NO. 43 vh43
```
atctgcacag taatacaggg ctatgtcctg agctctcagg ctgttcatct gtagataaag      60
catgttcttg gctttgtctc tggagatggt gaatcgaccc ttcacagcgt ctgcatagta    120
tgtgctgctt ccattactgc taatgtatgt gacccactgt agcccatcc caggagactg     180
acggagacaa tgcatgctgt agctactgaa ggtgaacctt gaggcacac aggagagtct     240
ctgggacccc ccaggtttca ctcggtctcc cccagactcc agcagctgta cttc          294
//
```

TABLE 1-continued

Canine IgH locus

SEQ ID NO. 44 vh44
```
gtctgcacag taatatatgg ccgtgtcctc ggctctcagg ctgttcatct gcagatacag    60
cgtgttcttg gcattgtctc tggagatggt gaatcggccc ttcacagtgt ctgcatacct   120
tgagctactt ccatcatacc taatccatga dacccactgc agccctgcc ctggagcctg   180
gtggacccag ctcatttcac tgctactgaa ggtgaatcca gaggccacac aggagagtct   240
cagggaccct ccaggcttca ccaaatcttc cccagactcc accagctgta cctc          294
//
```

SEQ ID NO. 45 vh45
```
gtccacacag taatacacag ctgtgtcctc ggctctcagg ctgttcatct gcagatacac    60
tgtgttcctg gcgttgtctc tggagatggt gaatcggccc ttcacagcgt cagtgtagta   120
tgtgctactt ccatcatagc taatagctgt gacccactgc agcccttcc caggagcctg   180
gcggacccag ctcatgctgt agctactgaa ggttaatcca gaggccacac aggagagtct   240
cagggacccc ccaggcttcg ccaggtctcc cccagactcc accagctgca cctc          294
//
```

SEQ ID NO. 46 vh46 pseudo
```
gtgtgcacag taatacacag ccgtgtcctc agctctcagg ctgttcatct gcagatacag    60
cgtgttcttg gcattgtctc tggagatggt gaatcggccc ttcacagcat ctgcgtggta   120
tgtggtactt ccatctttgt taattactga gactcagtgc agcccttcc ctggagcctg   180
gcggacccag cttatccagt aactactgaa agtgaatgca gagctacaa aggagagtct   240
cagggacccc ccaggcttca ccagctctcc cccagattcc accagtggca cctc          294
//
```

SEQ ID NO. 47 vh47 pseudo
```
cctcgcacag caatgcacgg ctgtgtcctc agctctcagg ctgttcatct gcagatacag    60
catgttcctg gtgctgtctc tggagatggt gaatcagccc tttacagcgt ctgcatagta   120
catgctactt ccattactgc tattggatat gacccactgt agccactacc gggagactgg   180
tggagccaat gtatgctgtt gctatgaaag gtgaatgtag aggactcaca gaagagtctc   240
agggaccgc caggcttcac caggtctccc ctagatttca ccaactgctc ctca           294
//
```

SEQ ID NO. 48 vh48 pseudo
```
tccctcgcac agtaatacat ggccttgtcc tcagctctca ggctgttcat ctgcagaaac    60
actgtgttct tggcgttctc tggagatggt gaatcggccc ttcacagcat ctgtgtagct   120
tgtgctattt ccactagctt aaatccatgc gacccactga atccccttcc cgggagcctg   180
gcggacccag ctcatgctgt agctactgaa ggtgaatcca gcggcacac aggagagtct   240
cagggacccc ccaggcttca tgaggtctcc cccagactcc accagctgca cctc          294
//
```

SEQ ID NO. 49 vh49
```
cttcgcacag taatacacgg ctgtgtcctc agctctcagg ctgttcatct gcagatacag    60
cgtgttcttg gcgttgtctc tggagatggt gaatcggccc ttcacagcat ctgcgtagcc   120
tgtgctcctt ccatcattgc taatccgtgt gagccactgc agcccttcc ctggagcctg   180
gcggacccag tccatgtcgt tgctactgaa ggtgaaacca gaggcacac aggagagtct   240
caaggacccc ccaggcttca ccaggtctcc cccagactcc accagctgca cctc          294
//
```

SEQ ID NO. 50 vh50 pseudo
```
cttcgcacag taatacatgg ccgtgtcctc agctctcagg ctgttcatct gtagatacag    60
catgttcttg gcgttgtctc tggagatggt gaatcggccc ttcacagcgt ctgcgtagtt   120
tgtgctactt ccatccctgc taataactgc gacccactgc agcccttcc ctggagcctg   180
gcggacccag tgcatggcat agctactgaa agtgaatccg gaggtcacac aggacagtct   240
tagggaaccc caggcttcac caggtctccc ccagactcct ccagctgcac ctca          294
//
```

SEQ ID NO. 51 vh51 pseudo
```
catcgcacag taatataggg ccgtgtcctc ggctctcagg ctggtcatct gcagatacag    60
agtgttcttg gaattgtctc tggagatggt gaatcggccc ttcacagcat cagtgtagta   120
tgtgctactt ccatcactcc taattcatgc gaaccactgc agcccttcc ctggagcctg   180
gtggacccag tgcatgtagt agatactgaa ggtgaatccg gaggccacac aggacagtct   240
cagggacccc ccaggcttca ccagctctcc cccatactcc accagctgca cttc          294
//
```

SEQ ID NO. 52 vh52 pseudo
```
actcacacag taatacacgg ccgtgtcttc ggctctcagg ctgttcacct gcaggtacag    60
cgtgttcttg gcattgtctc tggagatggt gaatgggccc ctcacagcgt ctgcatagtt   120
tgtgctactt ccagtactgc taatttctgc aagccactgc agcccatcc ctggagcctg   180
gtggacccag tacatccagt agctactgaa ggtgaatcca gggtccacac aggagagtct   240
cagggacccc ccaggcttca ccaggcctcc ctagactcca ccagctgcat ctca          294
//
```

TABLE 1-continued

Canine IgH locus

SEQ ID NO. 53 vh53
```
cttcacacac taatacacgg ccgtgtcctc ggctctcagg ctgttcatct gcagatacag    60
cgtgttcttg gcattgtctc tggagatggt gaatcggccc ttcacagcgt ctgcatagct   120
tgtgctactt ccatcactgc taatgtatcc gacccactgc agcccttcc ctggagcctg    180
gcggacccag ttcatgtagt tgctactgat agtgaatccg gaggccacac aggagagtct   240
cagggacccc ccaggcttca tcaggtctcc cccagactcc accagctgca cctc          294
//
```

SEQ ID NO. 54 vh54 pseudo
```
actcacacag taatacgcgg tcatgtcctg ggctctcagg ctgttcatct gcagatacag    60
catgttcttg gcattgtctc tgaagatggt gaattggccc ttcactgtgt ctgcatagta   120
tgtgctacct ccaccactgt taataattgc aacccacccc aacccttcc ctggagcctg    180
gcagacccaa tgcatccagt agctactgaa ggtgaatcca gaggccacac aagagagtct   240
cagagactcc ccaggcttca ccaggtttcc ccagactcca ccagctgcac ctca          294
//
```

SEQ ID NO. 55 vh55 pseudo
```
gggaggtttg tgtctgggct cacacttagg tcacctcact gtgtccttcg cacagtaata    60
cacggccgtc ttggcattgt ctctggagat ggtgaatcgc cccttcacag cgtctgtgta   120
gtatgtgcta cttccgtcac tgctaatccg tgcgacccac ttcagcccct ccctggagcc   180
tggcagaccc attccatata gtagctactg aaggtgaatc cagaggccac acaggagagt   240
ctcagggatc cccaggctt caccaggtct cccccagatt ccaccagctg cacctc         296
//
```

SEQ ID NO. 56 vh56 pseudo
```
ccttgcacag taatataggg ccgtatcatc agctctcagg ctgttcatct gcagatacag    60
agtgttcttg gaattgtctc tggagatggt gaatctgccc ttcacagcgt ctgggtagct   120
tgtgctactt ccatcactcc taattcttgc aacccactgc agcccttcc ctggagcctg    180
cagacccagt gcatgtagta gctactgaag gtgaatccag aggccacaca ggacagtctc   240
agggaacccc caggcttcac cagctctccc ccagactcca caagctgcac ttca          294
//
```

SEQ ID NO. 57 vh57
```
cttcgcacag taatacacgg ctgtgtcctc agctctcagg ctgttcatct gcagatacag    60
cgtgttcttg gcattgtctc tggagatggt gaatcggccc ttcacagtgt ctgcggagcc   120
tgtgctactt ccactactgc taataactgc tacccacttc agcccttcc ctggagcctg    180
gcggacccag ctcttggcat ggctactgaa ggtgaatccg gaggccacac aagagagtct   240
cagggatccc ccaggcttca ccaggtctcc cccagactcc accagctgca cctc          294
//
```

SEQ ID NO. 58 vh58
```
ccgcaatgtg tcactcacac aataatacag ggctatcagg ctgttcatat gcagatacag    60
cgtgttcttg gcattgtctc tggagatggt gaattgcccc ttcacagcat ctgcatagct   120
tttgctgctt ccaccagtat taacccatgt gacccactgc agcccttcc ctggagcctg    180
gctgacccag ctcatccagt agctcctgaa ggtgaatcca gaggtcacat aggagagttt   240
aattgatccc caggcttca acaggtctcc cccagactcc accagcttca cctc           294
//
```

SEQ ID NO. 59 vh59
```
cctcgcacag taatacacgg gcatgtcctc agctctcagg ctgttcatct gcagatacag    60
cgtgttcttg gcattgtctc tggagatggt gaatcggccc ttcacagcgt cagtgtagta   120
tgtgctactt ccatcagtgg taatagctgc gacccactgc agcccttcc caggagcctc    180
gtggacccag taaatggcat agctatagaa ggttaatcca gaggccacac aggacagtct   240
cagggaaccc ccaggcttca ccaggtttcc accagactcc accagctgca cctc          294
//
```

SEQ ID NO. 60 vh60 pseudo
```
gtctgcacag taatacagag ccgtgtcctc agctctcagg ctgttcatct gaagatacag    60
catgttcttg gcgttgtctc tggagatggt gaatcggccc ttcacagcgt ctttgtaacc   120
tgtgctactt ccatcatagc taatgtatgc aacacactgc agcccttcc tggagcctaa    180
tggacccagc tcatgtcaca gttactgaag gtgaatcaag gggccacaca ggagagtctc   240
agggacccc cagacttcac cagatctccc cgagactcca ccagctgctc ctca           294
//
```

SEQ ID NO. 61 vh61 pseudo
```
cctcgcacag caatgcacgg ctgtgtcctc agctctcagg ttattcatct gcagatacag    60
catgttcctg gtgttgtctc tggagatggt gtatcagccc tttacagcgt ctgcatagta   120
catgctactt ccattactgc tattggatat gacccactgt agccactacc gggagactgg   180
tggagccaat gcatgctgta gctatgaaag gtgaacgtag aggactcaca gaagagtctc   240
agggacccgc caggcttcac caggtctccc ctagatttca ccaactgctc ctca          294
//
```

TABLE 1-continued

Canine IgH locus

SEQ ID NO. 62 vh62 pseudo
```
gtgtccctg cacaggaata catggccgtg tcctcagctc tcaggcatct gcagaaacag      60
tgtgttcttg gcgttgtctc tggagatggt gaatcggccc ttcacagcgt ctgcgtagct     120
tgtgctactt ccgctagcat atatccatgc gacccactga ggtgaatcca gcggccacac     180
gcggacccag ctcatgctgt agctactgaa ggtgaatcca gcggccacac aggagagtct     240
cagggacccc ccaggcttca cggggtctcc cgcagactcc accagctgca cctc           294
//
```

SEQ ID NO. 63 vh63 pseudo
```
gtctgcacag taatacaagg ccgtgtcctc ggctctcagg ctgttcatct gcagatagag      60
cgtgttcttg gcattgtctc tggagatggt gaatcggccc ttcacagcat ctgtgtagta     120
tgtgctactt ccactattgc taattttgc gacccactgc agcccttcc aggagcctgg      180
cggacacagc tcatgctgta gctactgaag tgaatccaga ggccatacag gacagtctca     240
gggaccgccc aggcttcacc aggtctccgc cagactccac cagctgcacc tcac           294
//
```

SEQ ID NO. 64 vh64
```
ctttgcacag taatacatag ccgtgtcctc ggctctcagg ctgttcatct gcagatacag      60
cgtgttcttg gcattgtctc tggagatggt gaatcggccc ttcacagcct ctgcgtagta     120
tgtgctactt ccatcactgc taatccgtgc gacccactga agcccttcc ctggagcctg     180
gcggacccag tacatgtagt agctactgaa ggtgaatcca gaggccacac aggacagtct     240
cagggacccc ccaggcttca ccaggtctcc cccagactcc accagctgca cctc           294
//
```

SEQ ID NO. 65 vh65 pseudo
```
ttgcacaggg atatagggcc gtgtccttgg ctctcaggct gttcatctgc agatacagaa      60
tgttcttgga attgtctttg gagatggtgt atcggtcctt cacagcatca gtgtatatgt     120
gctacttcca tcactcctaa ttcatgtgac ccacagcagc catttccctg gagcctggcg     180
gacccagtac atgtagtagc tactgaaggt gaatccagag ccacacagg agagtctcag      240
ggaccccca ggcttcacca gctctccccc agactccacc agctgcactt c                291
//
```

SEQ ID NO. 66 vh66
```
cttcggacag taatacacgg ctgtgtcctc ggatctcagg ctgttcatct gcagatacag      60
tgtgttcctg gcattgtctc tggagatggt gaaccggccc ttcacagcat ctgcgtagta     120
tgtgctactt ccaccactgt taatgtatgc gacccactgc agcccttcc ctggagcctg     180
gcggacccag ctcatggcat agctactgaa ggtgaatcca gaggccacac aggacagtct     240
cagggatccc ccaggcttca ccaggtctcc cccagactcc accagctgta cctc           294
//
```

SEQ ID NO. 67 vh67
```
ccttgcacag taatatacag ccgtgtcctc ggctctcagg ctgtgcatcc gtagatacag      60
cgtgttcttg gcgttgtctc tggagatggt gaatcggccc ttcacagcgt ctgcgtagct     120
tgtgctattt ccactactgc taatttctgc aacacactgt agcccttcc ctggagcctg     180
gcagaaccag ctcatgtaga agctactgaa ggtgaatcca gaggcacac aggagagtct     240
cagggaccgc tcaggcttca caaggtctcc tccagactcc accagctgca cctc           294
//
```

SEQ ID NO. 68 vh68
```
ccttgcacag ttatacaggg ccgtatcctc agctctcagg ctgttcatct gcagatacag      60
cgtgttcttg gcattgtctc tggaaatggt gaatcggccc ttcacagcgt ctgcgtatta     120
tgtgctactt ccatcactgc taatgtatcc gacccactgc agcccttcc taggagcctg     180
gcggacccag ctcatggcat agctactgaa ggtgaatcca gaggccacac aggacagtct     240
cagggaatcc ccaggcttca ccaggtctcc gccagactcc accagctgca cctc           294
//
```

SEQ ID NO. 69 vh69 pseudo
```
gtctgcacag taatacaggg ccgtgtgctc agctctcagg ctgttcatct gaagatacag      60
cgtgttcttg gcgttgtctc tggagatggt gaatcggccc tgcacagcgt cifigtaacc     120
tgtgctactt ccatcatagc taatatatgc aatacactgc agcccttcc tggagtctaa     180
tggaccgagc tcatgtcata gttactgaag gtgaatccag ggccacaca ggagagtctc     240
agggaccccc caggcttcac caggtctccc ccagactcca tcagctgcac ctca           294
//
```

SEQ ID NO. 70 vh70 pseudo
```
ccctcgcaca gtaatacaca gcggtgtcct cggctctcag gctgttcaac tgcagataca      60
gcatgttctt ggcgttgtct ctggagaggt gaatcggccc ttcacagcat ctgtgtacct     120
tgtgctactt ccaccactgt taatgtatgc gaccccactgc agccacttcc ctggagcctg    180
gcggacccag ctcatgatgt agctactgaa ggtgaatcca gaagcacac aggagagtct     240
caggagccca caaggcttca ccaagtctcc cccagactcc accagctgca cctc           294
//
```

TABLE 1-continued

Canine IgH locus

SEQ ID NO. 71 vh71
```
gtctgcacag taatacacgg ccgtgtcctc ggctctcagg ctgttcatct gcagatacac    60
tgtgttcttg gcgttgtctc tggagatggt gaatcggccc ttcacagcgt ctacatggta   120
tgtgctactt ccactactgc taatagctgc aacccactgc agcccttcc ctggagcctg    180
gcagacccaa ctcatggcat agctactgaa ggtgaatcca gaggccacac aggagagtct   240
cagggacccc cctggcttca ccagatctcc cccaagctcc accagctgca attc         294
//
```

SEQ ID NO. 72 vh72
```
gtgtgcacag taatacacag tcgtgccctc agctctcagg ctgttcatct gcagatacag    60
cgtgttcttg gcattgtctc tggagatggt gaatcggccc ttcacagcat ctgcgtggta   120
tgtggtactt ccatctttgt taattactga acccagtgc agcccttcc ctggagcttg     180
gcggaccag cttatccagt aactactgaa agtgaatcca gaggctacac aggagaatct    240
cagggacccc tcaggcttca ccagctctcc cccagattcc accagtggca cctc          294
//
```

SEQ ID NO. 73 vh73pseudo
```
ccttgcacag gaatacatgg ccgtgttctc agctctcagg ctgttcatct gcagaaacac    60
tgtgttcttg gcgttgtctc tggagatggt gaatcggccc ttcacagcat ctgtgtagct   120
tgtgctactt ccactagcat aaatctatgt gacccactgc accccttcc cgggagcctg    180
gcggacccag ctcatgctgt agctactaaa ggtgaatcca gcggccacac aggagagtct   240
cagggacccc tccggcttca caaggtctcc cccagactcc accagctgca cctc          294
//
```

SEQ ID NO. 74 vh74
```
ctttgcacag taatacacgg ccgtgtcctc ggctcccagg ctgttcatct gcagatacag    60
cgtgttcttg gcattgtctc tggagatggt gaattgaccc ttcacagcgt ctgggtagta   120
tgtgctactt ccatcactgc taatctgtgc gacccactgc agcccttcc ctggagcctg    180
gcggacccat tccatgtagt agctactgaa ggtgaatcca gaggccacac aagagagtct   240
cagggatccc ccaggcttca ccagatctcc cccagactcc accagctgca cctc          294
//
```

SEQ ID NO. 75 vh75
```
catcgcacag taatacacag cagagtcctc ggctctcagg ctgttcatct gcagatagag    60
cgtgttcttg gcgttgtctc tggagatggt gaatcggccc ttcacagcct gtgggtagta   120
tgtgctactt ccatcactgc taatccctgc gacccactgc agcctcttcc ctggagcctg    180
gcggacccag tccatgtagt agctactgaa ggtgaatcca gaggccacac aagagagtct   240
cagggacccc ccaggcttca ccaggtttcc tccagactcc accagctgca cctc          294
//
```

SEQ ID NO. 76 vh76
```
ccttgcacag taatataggg ccatgtcctc ggctctctgg ctgttcatct gcagatacag    60
cgtattcttg gaattgtctc tggagatggt aaattggccc ttcatggcgt ctgcgtacct   120
tgtgctactt ccatcattgc taatccttgt gacccactgc agcccttcc ctgtagcctg     180
gcggaccag tgcatgtagt agctactgaa ggtgaatcca gaggccacac aagagagtct   240
cagggacccc ccagacttca ccaggtctcc tccagactcc accagctgca cctc          294
//
```

SEQ ID NO. 77 vh77
```
cttcgcacag taatgcatgg ccctgtcctc agctctcagg ctgttcatct gcagatagag    60
cgtgttcttg gcgttttctc tggagatggt gaatcggccc ttcactgtgt ctgcgtagta   120
tatgctacct ccaccactgt taataattgc gacccactcc agcccttcc ctggagcctg     180
gaggaccag tgcatccagt agctactgaa ggtgaatcca gaggacacac aagaaagtct   240
cagagacccc ccaggcttca ccaggtctcc cccagactct accagctgca actc          294
//
```

Dh sequences

Dh1 gtactactgt actgatgatt actgtttcaa c (SEQ ID NO. 78)
Dh2 ctactacggt agctactac (SEQ ID NO. 79)
Dh3 tatatatata tggatac (SEQ ID NO. 80)
Dh4 gtatagtagc agctggtac (SEQ ID NO. 81)
Dh5 agttctagta gttggggct (SEQ ID NO. 82)
Dh6 ctaactgggg c (SEQ ID NO. 83)

$J_H$ sequences

Jh1 tgaggagacg gtgaccaggg tgccctggcc ccagaggt ctaagta (SEQ ID NO. 84)
Jh2 tgaggagaca gtgaccaggg tgccctggcc ccagtaac caaa (SEQ ID NO. 85)
Jh3 tgaggagacg gtgaccaggg ttccctggcc ccagtagt caaa (SEQ ID NO. 86)
Jh4 tgaggacaca gtgaccaggg tcccttggcc ccagtagt (SEQ ID NO. 87)
Jh5 tgaggacacg aagagtgagg tgccatggcc ccagtagt ccatacc atagtaat
(SEQ ID NO. 88)

TABLE 2

| Canine Igκ Sequence Information |
|---|
| Vκ genes |

SEQ ID NO. 89: vk1
```
  1 GACATCACGA TGACTCAGTG TCCAGGCTCC CTGGCTGTGT CTCCAGGTCA
 51 GCAGGTCACC ACGAACTGCA GGGCCAGTCA AAGCGTTAGT GGCTACTTAG
101 CCTGGTACCT GCAGAAACCA GGACAGCGTC CTAAGCTGCT CATCTACTTA
151 GCCTCCAGCT GGGCATCTGG GGTCCCTGCC CGATTCAGCA GCAGTGGATC
201 TGGGACAGAT TTCACCCTCA CCGTCAACAA CCTCGAGGCT GAAGATGTGA
251 GGGATTATTA CTGTCAGCAG CATTATAGTT CT
```

SEQ ID NO. 90: vk2
```
  1 GATATTGTCA TGACACAGGC CCCACCGTCC CTGTCCGTCA GCCCTGGAGA
 51 GCCGGCCTCC ATCTCCTGCA AGGCCAGTCA GAGCCTCCTG CACAGTAATG
101 GGAACACCTA TTTGTATTGG TTCCGACAGA AGCCAGGCCA GTCTCCAGAG
151 GGCCTGATCT ATAAGGTGTC CAACCGCTTC ACTGGCGTGT CAGACAGGTT
201 CAGTGGCAGC GGGTCAGGGA CAGATTTCAC CCTGAGAATC AGCAGAGTGG
251 AGGCTGACGA TGCTGGAGTT TATTACTGCG GGCAAAATTT ACAGTTT
```

SEQ ID NO. 91: vk3
```
  1 ATTGTCATGA CACAGACGCC ACCGTCCCTG TCTGTCAGCC CTAGAGAGAC
 51 GGCCTCCATC TCCTGCAAGG CCAGTCAGAG CCTCCTGCAC AGTGATGGAA
101 ACACCTATTT GGATTGGTAC CTGCAAAAGC CAGGCCAGTC TCCACAGCTT
151 CTGATCTACT TGGTTTCCAA CCGCTTCACT GGCGTGTCAG ACAGGTTCAG
201 TGGCAGCGGG TCAGGGACAG ATTTCACCCT GAGAATCAGC AGAGTGGAGG
251 CTAACGATAC TGGAGTTTAT TACTGCGGGC AAGGTACACA GCTT
```

SEQ ID NO. 92: vk4
```
  1 GATATTGTCA TGACACAGAC CCCACTGTCC CTGTCCGTCA GCCCTGGAGA
 51 GCCGGCCTCC ATCTCCTGCA AGGCCAGTCA GAGCCTCCTG CACAGTAATG
101 GGAACACCTA TTTGTATTGG TTCCGACAGA AGCCAGGCCA GTCTCCACAG
151 CGTTTGATCT ATAAGGTCTC AACAGAGAC CCTGGGGTCC CAGACAGGTT
201 CAGTGGCAGC GGGTCAGGGA CAGATTTCAC CCTGAGAATC AGCAGAGTGG
251 AGGCTGATGA TGCTGGAGTT TATTACTGCG GGCAAGGTAT ACA
```

SEQ ID NO. 93: vk5
```
  1 GATATTGTCA TGACACAGAC CCCACTGTCC CTGTCTGTCA GCCCTGGAGA
 51 GACTGCCTCC ATCTCCTGCA AGGCCAGTCA GAGCCTCCTG CACAGTGATG
101 GAAACACGTA TTTGAACTGG TTCCGACAGA AGCCAGGCCA GTCTCCACAG
151 CGTTTAATCT ATAAGGTCTC CAACAGAGAC CCTGGGGTCC CAGACAGGTT
201 CAGTGGCAGC GGGTCAGGGA CAGATTTCAC CCTGAGAATC AGCAGAGTGG
251 AGGCTGACGA TACTGGAGTT TATTACTGCG GGCAAGGTAT ACA
```

SEQ ID NO. 94: vk6
```
  1 GATATTGTCA TGACACAGAA CCCACTGTCC CTGTCCGTCA GCCCTGGAGA
 51 GACGGCCTCC ATCTCCTGCA AGGCCAGTCA GAGCCTCCTG CACAGTAACG
101 GGAACACCTA TTTGAATTGG TTCCGACAGA AGCCAGGCCA GTCTCCACAG
151 GGCCTGATCT ATAAGGTCTC CAACAGAGAC CCTGGGGTCC CAGACAGGTT
201 CAGTGGCAGC GGGTCAGGGA CAGATTTCAC CCTGAGAATC AGCAGAGTGG
251 AGGCTGACGA TGCTGGAGTT TATTACTGCA TGCAAGGTAT ACA
```

SEQ ID NO. 95: vk7
```
  1 ATTGTCATGA CACAGACCCC ACCGTCCCTG TCCGTCAGCC CTGGAGAGCC
 51 GGCCTCCATC TCCTGCAAGG CCAGTCAGAG CCTCCTGCAC AGTAACGGGA
101 ACACCTATTT GAATTGGTTC CGACAGAAGC CAGGCCAGTC TCCACAGGGC
151 CTGATCTATA GGGTGTCCAA CCGCTCCACT GGCGTGTCAG ACAGGTTCAG
201 TGGCAGCGGG TCAGGGACAG ATTTCACCCT GAGAATCAGC AGAGTGGAGG
251 CTGACGATGC TGGAGTTTAT TACTGCGGGC AAGGTATACA
```

SEQ ID NO. 96: vk8
```
  1 GATATTGTCA TGACACAGAC CCCACTGTCC CTGTCTGTCA GCCCTGGAGA
 51 GACTGCCTCC ATCTCTTGCA AGGCCAGTCA GAGCCTCCTG CACAGTGATG
101 GAAACACGTA TTTGAATTGG TTCCGACAGA AGCCAGGCCA GTCTCCACAG
151 CGTTTGATCT ATAAGGTCTC CAACAGAGAC CCTGGGGTCC CAGACAGGTT
201 CAGTGGCAGC GGGTCAGGGA CAGATTTCAC CCTGAGAATC AGCAGAGTGG
251 AGGCTGACGA TACTGGAGTT TATTACTGCG GGCAAGTTAT ACA
```

SEQ ID NO. 97: vk9
```
  1 ATTGTCATGA CACAGACCCC ACTGTCCCTG TCCGTCAGCC CTGGAGAGAC
 51 TGCCTCCATC TCCTGCAAGG CCAGTCAGAG CCTCCTGCAC AGTGATGGAA
101 ACACGTATTT GAATTGGTTC CGACAGAAGC CAGGCCAGTC TCCACAGCGT
151 TTGATCTATA AGGTCTCCAA CAGAGACCCT GGGGTCCCAG ACAGGTTCAG
201 TGGCAGCGGG TCAGGGACAG ATTTCACCCT GAGAATCAGC AGAGTGGAGG
251 CTGACGATAC TGGAGTTTAT TACTGCATGC AAGGTACACA GTTT
```

TABLE 2-continued

Canine Igκ Sequence Information

SEQ ID NO. 98: vk10
  1 TCGTCATGAC ACAGACCCCA CTGTCCCTGT CCGTCAGCCC TGGAGAGACT
 51 GCCTCCATCT CCTGCAAGGC CAGTCAGAGC CTCCTGCACA GTAACGGGAA
101 CACCTATTTG TTTTGGTTCC GACAGAAGCC AGGCCAGTCT CCACAGCGCC
151 TGATCAACTT GGTTTCCAAC AGAGACCCTG GGGTCCCACA CAGGTTCAGT
201 GGCAGCGGGT CAGGGACAGA TTTCACCCTG AGAATCAGCA GAGTGGAGGC
251 TGACGATGCT GGAGTTTATT ACTGCGGGCA AGGTATACA

SEQ ID NO. 99: vk11
  1 GATATTGTCA TGACACAGGC CCCACCGTCT CTGTCCGTCA GCCCTAGAGA
 51 GCCGGCCTCC ATCTCCTGCA AGGCCAGTCA GAGCCTCCTG CACAGTAATG
101 GGAACACCTA TTTGTATTGG TTCCGACAGA AGCCAGGCCA GTCTCCAGAG
151 GGCCTGATCT ATAAGGTGTC AACCGCTTC ACTGGCGTGT CAGACAGGTT
201 CAGTGGCAGC GGGTCAGGGA CAGATTTCAC CCTGAGAATC AGCAGAGTGG
251 AGGCTGACGA TGCTGGAGTT TATTACTGCG GGCAAGGTAT ACAGTTT

SEQ ID NO. 100: vk12
  1 GATATCGTCA TGACACAGAC CCCACTGTCC CTGTCCGTCA GCCCTGGAGA
 51 GCCGGCCTCC ATCTCCTGCA AGGCCAGTCA GAGCCTCCTG CACAGTAACG
101 GGAACACCTA TTTGTTTTGG TTTCGACAGA AGCCAGGCCA GTCTCCACAG
151 CGTTTGATCT ATAAGGTCTC AACAGAGAC ACTGGGGTCC CAGACAGGTT
201 CAGTGGCAGC GGGTCAGGGA CAGATTTCAC CCTGAGAATC AGCACAGTGG
251 AGGCTGACGA TACTGGAGTT TATTACTGCG GGCAAGGTAC ACAGTTT

SEQ ID NO. 101: vk13
  1 GATATTGTCA TGACACAGAC CCCACTGTCC CTGTCTGTCA GCCCTGGAGA
 51 GACTGCCTCC ATCTCCTGCA AGGCCAGTCA GAGCCTCCTG CACAGTGATG
101 GAAACACGTA TTTGAATTGG TTCCGACAGA AGCCAGGCCA GTCTCCACAG
151 CGTTTGATCT ATAAGGTCTC AACAGAGAC ACTGGGGTCC CAGACAGGTT
201 CAGTGGCAGC GGGTCAGGGA CAGATTTCAC CCTGAGAATC AGCAGAGTGG
251 AGGCTGACGA TACTGGAGTT TATTACTGTG GGCAAGTTAT ACA

SEQ ID NO. 102 vk14
  1 GATATTGTCA TGACACAGAC CCCACTGTCC CTGTCCGTCA GCCCTGGAGA
 51 GACTGCCTCC ATCTCCTGCA AGGCCAGTCA GAGCCTCCTG CACAGTGATG
101 GAAACACGTA TTTGAATTGG TTCCGACAGA AGCCAGGCCA GTCTCCACAG
151 CGTTTGATCT ATAAGGTCTC AACAGAGAC ACTGGGGTCC CAGACAGGTT
201 CAGTGGCAGC GGGTCAGGGA CAGATTTCAC CCTGAGAATC AGCAGAGTGG
251 AGGCTGACGA TACTGGAGTT TATTACTGCG GGCAAGGTAC ACAGTTT

SEQ ID NO. 103: vk15
  1 GATATTGTCA TGACACAGAA CCCACTGTCC CTGTCTGTCA GCCCTGGAGA
 51 GACGGCCTCC ATCTCCTGCA AGGCCAGTCA GAGCCTCCTG CACAGTGATG
101 GAAACACGTA TTTGAACTGG TTCCGACAGA AGCCAGGCCA GTCTCCACAG
151 CGTTTAATCT ATAAGGTCTC AACAGAGAC CCTGGGGTCC CAGACAGGTT
201 CAGTGGCAGC GGGTCAGGGA CAGATTTCAC CCTGAGAATC AGCAGAGTGG
251 AGGCTGACGA TACTGGAGTT TATTACTGCG GGCAAGGTAT ACA

SEQ ID NO. 104: vk16
  1 GATATTGTCA TGACACAGAC CCCACTGTCC CTGTCCGTCA GCCCTGGAGA
 51 GCCGGCCTCC ATCTCCTGCA AGGCCAGTCA GAGCCTCCTG CACAGTAATG
101 GGAACACCTA TTTGTATTGG TTCCAACAGA AGCCAGGCCA GTCTCCACAG
151 CGTTTGATCT ATAAGGTCTC AACAGAGAC CCTGGGGTCC CAGACAGGTT
201 CAGTGGCAGC GGGTCAGGGA CAGATTTCAC CCTGAGAATC AGCAGAGTGG
251 AGGCTGATGA TGCTGGAGTT TATTACTGCG GGCAAGGTAT ACA

SEQ ID NO. 105: vk17
  1 GATATTGTCA TGACACAGAC CCCACTGTCC CTGTCCGTCA GCCCTGGAGA
 51 GACGGCCTCC ATCTCCTGCA AGGCCAGTCA GAGCCTCCTG CACAGTAACG
101 GGAACACCTA TTTGAATTGG TTCCGACAGA AGCCAGGCCA GTCTCCACAG
151 GGCCTGATCT ATAAGGTCTC AACAGAGAC CCTGGGGTCC CAGACAGGTT
201 CAGTGGCAGC GGGTCAGGGA CAGATTTCAC CCTGAGAATC AGCAGAGTGG
251 AGGCTGACGA TGCTGGAGTT TATTACTGCA TGCAAGGTAT ACA

SEQ ID NO. 106: vk18
  1 GATATCGTCA TGACACAGAC CCCACTGTCC CTGTCCGTCA GCCCTGGAGA
 51 GCCGGCCTCC ATCTCCTGCA AGGCCAGTCA GAGCCTCCTG CACAGTAATG
101 GGAACACCTA TTTGTATTGG TTCCGACAGA AGCCAGGCCA GTCTCCAGAG
151 GGCCTGATCT ATAAGGTGTC AACCGCTTC ACTGGCGTGT CAGACAGGTT
201 CAGTGGCAGC GGGTCAGGGA CAGATTTCAC CCTGAGAATC AGCAGAGTGG
251 AGGCTGACGA TGCTGGAGTT TATTACTGCG GGCAAGGTAT ACA

TABLE 2-continued

Canine Igκ Sequence Information

SEQ ID NO. 107: vk19 Pseudogene
```
  1 TCTTGACCTA GTCTCCAGCC TCCCTGGCTA TTTCCCAAGG GGACAGAGTC
 51 AACCATCACC TATGGGACCA GCACCAGTAA AAGCTCCAGC AACTTAACCT
101 GGTACCAACA GAACTCTGGA GCTTCTTCTA AGCTCCTTGT TTACAGCACA
151 GCAAGCCTGG CTTCTGGGAT CCCAGCTGGC TTCATTGGCA GTGGATGTGG
201 GAACTCTTCC TCTCTCACAA TCAATGGCAT GGAGGCTGAA GGTGCTGCCT
251 ACTATTACTA CCAGCAGTAG GGTAG
```

Jκ genes

Jκ1 gtggacgttc ggagcaggaa ccaaggtgga gctcaaac (SEQ ID NO. 108)
Jκ2 ttatactttc agccagggaa ccaagctgga gataaaac (SEQ ID NO. 109)
Jκ3 gttcactttt ggccaaggga ccaaactgga gatcaaac (SEQ ID NO. 110)
Jκ4 gcttacgttc ggccaaggga ccaaggtgga gatcaaac (SEQ ID NO. 111)
Jκ5 gatcacctttt ggcaaaggga cacatctgga gattaaac (SEQ ID NO. 112)

TABLE 3

Canine Igλ sequences

Vλ germline genes

VL1    (SEQ ID NO. 113)
       tcctcttgtc taaagaaaag aacatcactc tctctgtgtc tctcccctt tcagggtcct
       gggaccagtc tgtgctgact cagccgccct cagtgtcggg atctgtgggc cagagaatca
       ccatctcctg ctctggaagc acaaacagct accaacagct ctcaggaaag gcctctaaac
       tcctcgtaga tggtactggg aaccgaccct caggggtccc cgaccgattt tctggctcca
       aatctggcaa ctcaggcact ctgaccatca ctgggcttgg gacgaggctg aggacgaggc
       tgaggacgag gctgattatt attgttagtc cactgatctc acgcttggtg ctcccacagt
       gctctgggcc tacggggaag tgagacacaa acctgctgtc cctagaacaa tggcactgcc
       tgtgcaaccc tggccttagg VL2 pseudo  (SEQ ID NO. 114)
       cagtctgtac tgactcagcc ggcctcagtg tctgggtccc tgggccagag ggtcaccatc
       tcctgcactg gaagcagctc aacatcggt ggatattatg tgagctggct ctagcagctc
       ccgggaacag gccccagaac catcatctat agtagtagta accgaccttc aggggtccct
       gatcgattct ctggctccag gtcaggcagc acagccaccc tgaccatctc tgggctccag
       gctgaggatg aggctgatta ttactgttca acatacgaca gcagtctcaa agctcccaca
       gtgctccagg cctgtgggga agtgagacaa aaacccatttt acctatctgc aatgtgagtg
       agcgcccag gagcttcctg cgtaggctcc cctgggtttc tgctgattct tcagttgatg
       ccctgagccc aggtg VL3 pseudo  (SEQ ID NO. 115)
       atcccaggct gtggtgaccc agcttccttc tctgcatccc tgggaacaac agccagactc
       acatgcaccc tgagctgtgg cttcagtatt gatagatatg ctataaactg gttccagcag
       aaggcagaga gccttccctg gtacctactg tgctattact ggtactcaag tacacagttg
       ggcttcagcg tccccagctg catctctgga tccaagacaa ggccacattc acaaacgagt
       agaccatct ctggttgggt ctagagctcc agccccacct gagactgatg cacaattg VL4    (SEQ ID NO. 116)
       ggcccaggct gtgctgactc agctgccctc agtgtctgca gccctgggac agagggtcac
       catctgcact ggaagcagca ccaacatcgg cagtggttat tatacactat ggtaccagca
       gctgcaggaa agtcccctaa aactatcatc tatggtaata gcaatcgacc cttgagggtc
       ccggatcgat tctctggctc caagtatggc aattcagcca cgctgaccat cactgggctc
       caggctgagg acgaggatga ttattactgc cagtcctctg atgacaacct VL5    (SEQ ID NO. 117)
       cagtctgtgc tgactcagcc ggcctcggtg tctgggtccc tgggccagag ggtcaccatc
       tcctgcactg gaagcagctc caatgttggt tatggcaatt atgtgggctg gtaccagcag
       cttccaggaa caggccccag aaccattatc tgtttatacca atactcgacc ctctgggtt
       cctgatcgat actctggctc caagtcaggc agcacagcca ccctgaccat ctctgggctc
       caggctgaag acgagactga ttattactgt actacgtgtg acagcagtct caatgctagc
       acagtgctcc aggcctttgg agag VL6 pseudo  (SEQ ID NO. 118)
       gtgatggtga gggcgacttt gttcccagag atggatccag agaagcgatc agggaccca
       gaagggtgtc tgcttgtgct gtagataagc atgcaaggag cctggccttg ggtctgctgg
       taccagctgg ggtagtttct tgtagagact tacccagagc tgaggccaca tgtgaatgtg
       actgtccctc ctggagacac tgagagtgac ggatcctggg tgaccacagt ctg TABLE 3-continued

| Canine Igλ sequences |

VL7         (SEQ ID NO. 119)
            cagactgtgg taacccagga gccatcactc tcagtgtctc caggagggac agtcacactc
            acatgtggcc tcagctctgg gtcagtctct acaagtaatt accctggctg gtaccagcag
            acccaaggcc gggctcctcg cacgattatc tacaacacaa gcagccgccc ctctggggtc
            cctaatcgct tctctggatc catctctgga aacaaagccg ccctcaccat cacaggagcc
            cagcccgagg atgaggctga ctattactgt tccttgtata cgggtagtta c VL8         (SEQ ID NO. 120)
            cagtctgtgc tgactcagcc tccctcagtg tccgggttcc tgggccagag ggtcaccatc
            tcctgcactg gaagcagctc caacatcggt agaggttatg tgcactggta ccaacagctc
            ccaggaacag gccccagaac cctcatctat ggtattagta accgaccctc aggggtcccc
            gatcgattct ctggctccag gtcaggcagc acagccactc tgacaatctc tgggctccag
            gctgaggatg aggctgatta ttactgctca tcctgggaca gcagtctc VL9 pseudo  (SEQ ID NO. 121)
            cagcctgtga tgacccagct gtcctccctc tctgcatccc tggaaacaac aaccagacac
            acctgcaccc tgagcagtgg cttcagaaat aacagctgtg taataagttg attccagcag
            aagtcaggga gccctccctg gtgtctcctg tactattact cagactcaag tatacatttg
            ggctctgagg ttcccagctg cttctctgga tccaagacaa ggccacaccc acactgagta
            gacccatccc tgggtgggtc tagagctcca gccccactgg aggctgatgc acaattgca VL10        (SEQ ID NO. 122)
            ctgactcaaa cggcctccat gtctgggtct ctgggccaga gggtcaccgt ctcctgcact
            ggaagcagtt ccaacgttgg ttatagaagt tatgtgggct ggtaccagca gctcccagga
            acaggcccca gaaccatcat ctataatacc aatactcgac cctctggggt tcctgatcga
            ttctctggct ccatatcagg cagcacagcc accctgacta ttgctggact ccaggctgag
            gacgaggctg attattactg ctcatcctat gacagcagtc tc VL11 pseudo (SEQ ID NO. 123)
            cagtctgtgc tgaatcagct gccttcagtg ttaggatccc tgggccagag aatcaccatc
            tcctgctctg gaagcacgaa tgacatcggt atgcttggtg tgaactggta ccaagagccg
            ccaggaaagg ccccctaaact cctcgtagat ggtactggga atcgaccctc agggtccctg
            ccgattttct ggctccaaat ctggcaactc aggcactctg accatcactg ggctccaggc
            tgaggacgag gctgattatt attgtcagtc c VL12        (SEQ ID NO. 124)
            ctgctgtccc aggatgagca gtaataatca gcctcatcct cagcctggaa cccagagatt
            gtcagagtgt ctgtgctgcc tgacctggag ccagagaatt gattggggac ccctgagggt
            tggttactac taccatatat gagggttctt gggcgtgttc ccaggagctg ttggtaccag
            atcacataac ctctaccgac gttggagctg cttccagtgc aggatatagt gaccctctgg
            cccagggacc tgaacactga gggaggctga gtcagcacag actg VL13 pseudo (SEQ ID NO. 125)
            cagtctgtgc tgactcaacc agtctcagtg tctggggccc tgtgccagag ggtcaccatc
            tcctgcactg gaaacagctc caacattggt tatagcagtt gtgtgagctg atatcagcag
            ctcccaggaa caggccccag aaccatcatc tatagtatga atactcaacc ctctggggtt
            cctgatcgat tctctggctc caggtcaggc aactcagcca ccctaaccat ctctgggctc
            caggctgagg acaaggctga ctattactgc tcaacatatg acagcagtct cagtgctcac
            acggtgctcc aggcctgtgg ggaattgaga caaaaaccta cttatctgtc tgcagtgagc
            ggag

| Jλ germline genes |

JL1 agtgtgttcg gcggaggcac ccatctgacc gtcctcg (SEQ ID NO. 126)
J12 tacgtgttcg gctcaggaac ccaactgacc gtccttg (SEQ ID NO. 127)
JL3 tattgtgttc ggcggaggca cccatctgac cgtcctcg (SEQ ID NO. 128)
JL4 tggtgtgttc ggcggaggca cccacctgac cgtcctcg (SEQ ID NO. 129)
JL5 tgctgtgttc ggcggaggca cccacctgac cgtcctcg (SEQ ID NO. 130)

TABLE 4

Miscellaneous sequence data.

A. Pre-DJ

This is a 21609 bp fragment upstream of the Ighd-5 DH gene. The pre-DJ sequence can be found in *Mus musculus* strain C57BL/6J chromosome 12, Assembly: GRCm38.p4, Annotation release 106, Sequence ID: NC_000078.6
The entire sequence lies between the two 100 bp sequences shown below:
Upstream of the Ighd-5 DH gene segment, corresponding to positions 113526905-113527004 in NC_000078.6:
ATTTCTGTACCTGATCTATGTCAATATCTGTACCATGGCTCTAGCAGA
GATGAAATATGAGACAGTCTGATGTCATGTGGCCATGCCTGGTCCAGA
CTTG (SEQ ID NO. 131)

2 kb upstream of the Adam6a gene corresponding to positions 113548415-113548514 in NC_000078.6:
GTCAATCAGCAGAAATCCATCATACATGAGACAAAGTTATAATCAAGA
AATGTTGCCCATAGGAAACAGAGGATATCTCTAGCACTCAGAGACTGA
GCAC (SEQ ID NO. 132)

B. Adam6a

Adam6a (a disintegrin and metallopeptidase domain 6A) is a gene involved in male fertility. The Adam6a sequence can be found in *Mus musculus* strain C57BL/6J chromosome 12, Assembly: GRCCm38.p4, Annotation release 106, Sequence ID: NC_000078.6 at position 113543908-113546414.
Adam6a sequence ID: OTTMUSG00000051592 (VEGA)

TABLE 5

Chimeric canine/mouse Ig gene sequences.

Igk Version A

Sequence upstream of mouse Igkv 1-133
GCATTGAATAAACCAGTATAAACAAGCAAGCAAAGATAGATAGATAGATAG
ATAGATAGATAGATAGATAGATAGATAGATAGATAGATAGATAGATGATAG
ATAGATAGATAGATAGATAGATTTTTACGTATAATACAATAAAAACATTCA
TTGTCCCTCTATTGGTGACTACTCAAGGAAAAAAATGTTCATATGCAAGAA
AAAATGTTATCATTACCAGATGATCCAGCAATCTAGCAATATATATATTGT
TTATTCACAAAACATGAATGAACCTTTTAAGAAGCTGTTACAGTGTAAAAA
TTAAGTTAAATCACTGAAGAACATATACTGTGTGATTTCATTCAAATGAAA
TTTGAGAAGTAAATATATATGTATATATATATATATGTAAAAAATATAAGT
CTGAACTACAAAAATTCAATTTGTTTGATATGTAAGAATAAGAAAAATTGA
CCCCCAAAATTTGTTAATAATTAGGTATGTGTATTTTTATGAATATATAAG
TATAATAATGCTTATAGTATACACTATTCTGAATCACATTTATTCCCTAAG
TGTGTTCCCTTGATTATAATTAAAAGTATATTTTTAAATACAGAGTCAGA
GTACAGTCAATAAGGCGAAAATATAGTTGAATGATTTGCTTCAGCTTTTGT
AATGTACTAGAGATTGTGAGTACAAAGTCTCAGAGCTCATTTTATCCCTGA
CAATAACCAGCTCTGTGCTTCAAGTACATTTCCATCTTTCTCTGAAATTTA
GTCTTATATAGATAGACAAAATTTAAGTAAATTTCAAACTACACAGAACAA
CTAAGTTGTTGTTTCATATTGATAATGGATTTGAACTGCATTAACAGAACT
TTAACATCCTGCTTATTCTCCCTTCAGCCATCATATTTTGCTTTATTATTT
TCACTTTTTGAGTTATTTTTCACATTCAGAAAGCTCACATAATTGTCACTT
CTTTGTATACTGGTATACAGACCAGAACATTTGCATATTGTTCCCTGGGGA
GGTCTTTGCCCTGTTGGCCTGAGATAAAACCTCAAGTGTCCTCTTGCCTCC
ACTGATCACTCTCCTATGTTTATTTCCTCAAA(SEQ ID NO. 133)

Canine exon 1 (leader) from LOC475754 (SEQ ID NO. 134):
atgaggttcccttctcagctcctggggctgctgatgctctggatcc Canine intron 1 from LOC475754 (SEQ ID NO. 135)
Caggtaaggacagggcggagatgaggaaagacatgggggcgtggatggtga
gctccctggtgctgtttctctccctgtgtattctgtgcatgggacagatt
gccctccaacagggggaatttaattttttagactgtgagaattaagaagaat
ataaaatatttgatgaacagtactttagtgagatgctaaagaagaaagaag
tcactctgtcttgctatcttgggttttccatgataattgaatagatttaaa
atataaatcaaaatcaaaatatgatttagcctaaaatatacaaaacccaaa
atgattgaaatgtcttatactgtttctaacacaacttgtacttatctctca
ttattttaggatccagtggg

Chimeric canine/mouse Ig gene sequences.

Canine 5' part of exon 2 (leader) from LOC475754 (SEQ ID NO. 136)
aggatccagtggg

Canine Vκ from LOC475754 (SEQ ID NO. 137)
Gatattgtcatgacacagaccccactgtccctgtctgtcagccctggagag
actgcctccatctcctgcaaggccagtcagagcctcctgcacagtgatgga
aacacgtatttgaactggttccgacagaagccaggccagtctccacagcgt
ttaatctataaggtctccaacagagaccctggggtcccagacaggttcagt
ggcagcgggtcagggacagatttcaccctgagaatcagcagagtggaggct
gacgatactggagtttattactgcgggcaaggtatacaagat Mouse RSS heptamer
CACAGTG Mouse sequence downstream of RSS heptamer (SEQ ID NO. 138)
ATACAGACTCTATCAAAAACTTCCTTGCCTGGGGCAGCCCAGCTGACAATG
TGCAATCTGAAGAGGAGCAGAGAGCATCTTGTGTCTGTGTGAGAAGGAGGG
GCTGGGATACATGAGTAATTCTTTGCAGCTGTGAGCTCTG

Igk version B

Sequence upstream of mouse Igkv 1-133 (SEQ ID NO. 133)
GCATTGAATAAACCAGTATAAACAAGCAAGCAAAGATAGATAGATAGATAG
ATAGATAGATAGATAGATACATAGATAGATAGATAGATAGATGATAG
ATAGATAGATAGATAGATTTTTACGTATAATACAATAAAAACATTCA
TTGTCCCTCTATTGGTGACTACTCAAGGAAAAAAATGTTCATATGCAAGAA
AAAATGTTATCATTACCAGATGATCCAGCAATCTAGCAATATATATATTGT
TTATTCACAAAACATGAATGAACCTTTTAAGAAGCTGTTACAGTGTAAAAA
TTAAGTTAAATCACTGAAGAACATATACTGTGTGATTTCATTCAAATGAAA
TTTGAGAAGTAAATATATATGTATATATATATATATGTAAAAAATATAAGT
CTGAACTACAAAAATTCAATTTGTTTGATATGTAAGAATAAGAAAAATTGA
CCCCCAAAATTTGTTAATAATTAGGTATGTGTATTTTTATGAATATATAAG
TATAATAATGCTTATAGTATACACTATTCTGAATCACATTTATTCCCTAAG
TGTGTTCCCTTGATTATAATTAAAAGTATATTTTTAAATACAGAGTCAGA
GTACAGTCAATAAGGCGAAAATATAGTTGAATGATTTGCTTCAGCTTTTGT
AATGTACTAGAGATTGTGAGTACAAAGTCTCAGAGCTCATTTTATCCCTGA
CAATAACCAGCTCTGTGCTTCAAGTACATTTCCATCTTTCTCTGAAATTTA
GTCTTATATAGATAGACAAAATTTAAGTAAATTTCAAACTACACAGAACAA
CTAAGTTGTTGTTTCATATTGATAATGGATTTGAACTGCATTAACAGAACT
TTAACATCCTGCTTATTCTCCCTTCAGCCATCATATTTTGCTTTATTATTT
TCACTTTTTGAGTTATTTTTCACATTCAGAAAGCTCACATAATTGTCACTT
CTTTGTATACTGGTATACAGACCAGAACATTTGCATATTGTTCCCTGGGGA
GGTCTTTGCCCTGTTGGCCTGAGATAAAACCTCAAGTGTCCTCTTGCCTCC
ACTGATCACTCTCCTATGTTTATTTCCTCAAA Mouse Igkv 1-133 exon 1 (leader) (SEQ ID NO. 139)
ATGATGAGTCCTGCCCAGTTCCTGTTTCTGTTAGTGCTCTGGATTCAGG Mouse Igkv 1-133 intron 1 (SEQ ID NO. 140)
GTAAGGAGTTTTGGAATGTGAGGGATGAGAATGGGGATGGAGGGTGATCTC
TGGATGCCTATGTGTGCTGTTTATTTGTGGTGGGGCAGGTCATATCTTCCA
GAATGTGAGGTTTTGTTACATCCTAATGAGATATTCCACATGGAACAGTAT
CTGTACTAAGATCAGTATTCTGACATAGATTGGATGGAGTGGTATAGACTC
CATCTATAATGGATGATGTTTAGAAACTTCAACACTTGTTTTATGACAAAG
CATTTGATATATAATATTTTTAAATCTGAAAAACTGCTAGGATCTTACTTG
AAAGGAATAGCATAAAAGATTTCACAAAGGTTGCTCAGGATCTTTGCACAT
GATTTTCCACTATTGTATTGTAATTTCAG TABLE 5-continued Chimeric canine/mouse Ig gene sequences.

Mouse Igkv 1-133 5' part of exon 2 (leader)
(SEQ ID NO. 141)
AAACCAACGGT

Canine Vκ from LOC475754 (SEQ ID NO. 142)
Gatattgtcatgacacagaccccactgtccctgtctgtcagccctggagag
actgcctccatctcctgcaaggccagtcagagcctcctgcacagtgatgga
aacacgtatttgaactggttccgacagaagccaggccagtctccacagcgd
taatctataaggtctccaacagagaccctggggtcccagacaggdcagtgg
cagcgggtcagggacagatttcaccctgagaatcagcagagtggaggctga
cgatactggagtttattactgcgggcaaggtatacaagat TABLE 5-continued Chimeric canine/mouse Ig gene sequences.

Mouse RSS heptamer
CACAGTG

Mouse sequence downstream of RSS heptamer
(SEQ ID NO. 138)
ATACAGACTCTATCAAAAACTTCCTTGCCTGGGGCAGCCCAGCTGACAATG
TGCAATCTGAAGAGGAGCAGAGAGCATCTTGTGTCTGTGTGAGAAGGAGGG
GCTGGGATACATGAGTAATTCTTTGCAGCTGTGAGCTCTG

What is claimed is:

1. A method of producing antibodies comprising fully canine heavy and/or light chain variable domains and mouse constant domains, the method comprising:

(i) providing a transgenic mouse with a genome in which an entire endogenous immunoglobulin variable gene locus has been deleted and replaced with an engineered partly canine immunoglobulin locus comprising canine immunoglobulin variable gene VH, D and JH and/or canine VL and JL coding sequences and mouse immunoglobulin variable gene locus non-coding regulatory sequences, wherein the engineered partly canine immunoglobulin locus of the transgenic mouse is functional and expresses immunoglobulin chains comprised of canine variable domains and mouse constant domains; and (ii) isolating the antibodies comprising canine variable regions and mouse constant regions expressed by the transgenic mouse.

2. The method of claim 1, wherein the non-coding regulatory sequences comprise promoters preceding individual V gene segments, splice sites, and recombination signal sequences for V(D)J recombination.

3. The method of claim 1, wherein the engineered partly canine immunoglobulin locus further comprises an ADAM6 gene.

4. The method of claim 1, wherein the engineered partly canine immunoglobulin locus further comprises Pax-5-Activated Intergenic Repeat (PAIR) elements.

5. The method of claim 1, wherein the engineered partly canine immunoglobulin locus further comprises CTCF binding sites from a heavy chain intergenic control region 1.

* * * * *

SEQUENCE LISTING

<160> NUMBER OF SEQ ID NOS: 132

<210> SEQ ID NO 1
<211> LENGTH: 294
<212> TYPE: DNA
<213> ORGANISM: Canis familiaris

<400> SEQUENCE: 1
ccttgcacag taatacactg ccgtgtcctc atctctcagg ctgttcatct gcagatacag      60
cgtgttcttg gcattgtctc tggagatggt gaatcggccc ttcacagcgt ctgcgtagct     120
tgtgctactt ccatcactgc taatttgtga dacccactga gccccttcc ctggagcctg     180 gcggatccag ctcatgtagt tgctactgaa ggtgaatcca gaggccacac aggagagtct     240
cagggacccc ccaggcttca ccaggtctcc cccagactcc accagctgca cctc           294

<210> SEQ ID NO 2
<211> LENGTH: 294
<212> TYPE: DNA
<213> ORGANISM: Canis familiaris

<400> SEQUENCE: 2
ctttgcacag taatacaccg ctgtgtcctc agctctcagg ctgttcatct gcagatacag      60 cgtattctt gcgttgtctc tggagatggt gaatcggccc ttcacagcgt ctgcatagct     120
tgtgctactt ccatctttgt taatgtgtga dacccactga agccccttcc ctggagcctg     180
gcgggcccaa tacatgtagt aactactgaa ggtaaatcca gaggccacac aggagagtct     240
cagggacccc ccaggcttca ccatgtctcc cccagactcc accagctgca cctc           294

<210> SEQ ID NO 3
<211> LENGTH: 475
<212> TYPE: DNA
<213> ORGANISM: Canis familiaris

<400> SEQUENCE: 3
ggagtgaaca cagacaaacc accatgaagt tgttgctctg ctgggctttt cttcttgcaa      60
tttaaaaagt aattcatgga gaacaagaga ccttgaatat atgagttgag ttaagtgaga     120
gaaacagggg atgtgggaca gtttcctgac caggatgtct tgtgtctgca ggtgtccagg     180
gtgaggtgca gctggtggag tctggggag acctgatgaa gctgggggg gtccctgaga     240 ctctcctgtg tggcctctga attcatcttc agtggctact ggaagtactg gatccaccaa     300
gctccaggga aggggctgca gtgggtcaca tggattagca atgatggaag tagcaaaagc     360
tatgcagacg ctgtgaaggg ccaattcacc atctccaaag acaatgccaa atacacgctg     420
tatctgcaga tgaacagcct gagagccgag gacatggccg tgtattactg tatga         475

<210> SEQ ID NO 4
<211> LENGTH: 292
<212> TYPE: DNA
<213> ORGANISM: Canis familiaris

<400> SEQUENCE: 4
aggtgcagct ggtggagtct gggggagacc tgatgaagcc tgggggggtc cctgagactc    60
tcctgtgtgg cctctgaatt catcttcagt ggctactgga agtactggat ccaccaagct   120
ccagggaagg ggctgcagtg ggtcacatgg attagcaatg atggaagtag caaaagctat   180
gcagacgctg tgaagggcca attccaccatc tccaaagaca atgccaaata cacgctgtat   240
ctgcagatga acagcctgag agccgaggac atggccgtgt attactgtat ga           292

<210> SEQ ID NO 5
<211> LENGTH: 294
<212> TYPE: DNA
<213> ORGANISM: Canis familiaris

<400> SEQUENCE: 5
aatctgaggt ccagctggtg cagtctgggg ctgaggtgag gaaaccagtt tcatctgtga    60
aggtctcctg gaaggcatct ggatacacct acatggatgc ttatatgcac tggttatgac   120
aagcttcagg aataaggttt gggtgtatgg gatggattgg tcccaaagat ggtgccacaa   180
gatattcaca gaagttccac agcagagtct ccctgatggc agacatgtcc aaagcacagc   240
ctacatgctg ctgagcagtc agaggcctga ggacacacct gcatattact gtgt         294

<210> SEQ ID NO 6
<211> LENGTH: 294
<212> TYPE: DNA
<213> ORGANISM: Canis familiaris

<400> SEQUENCE: 6
actcgcacag taatacacgg ccgtgtcctc ggctctcagg ctgttcatct gaagatacag    60
cgtgttcttg gcgttgtctc tggagatggt gaatcggccc ttcacagcgt ctgcatagct   120
tgtgctactt ccaccactgt taatgtatgc gacccactga agcccttcc ctggagcctg    180 gcggacccag ctcatgtggt agctactgaa ggtgaatcca gaggccacac aggaaagtct   240
cagggacccc ccaggcttca ccaggtctcc cccagactcc accagctgca cctc         294

<210> SEQ ID NO 7
<211> LENGTH: 294
<212> TYPE: DNA
<213> ORGANISM: Canis familiaris

<400> SEQUENCE: 7
gtctgcacag taatacacgg ccgtgtcctc ggctctgagg ctgttcatct gcagatagag    60
cgtgttcttg gcgttgtctc tggagatggt gaatcggccc ttcacagcgt ctgcgtagct   120
tgtgctactt ccatcattgc taatgtatgc gacccactga agccccttc ctggagcctg   180 gcggatccag ctcatgtcgg agctactgaa ggtgaatcca gaggctacac aggagagtct   240
cagggacccc ccaggcttca ccaggtctcc cccagactcc accagctgca cctc         294

<210> SEQ ID NO 8
<211> LENGTH: 294
<212> TYPE: DNA
<213> ORGANISM: Canis familiaris

<400> SEQUENCE: 8

```
cctcatgcag taatacacgg ctgtgtcctc ggctctcagg ctgttcatct gcagatacag    60
catgttcttg gtgttgtctc tggagatggt gaatctgtcc ctcaaagtgt ctgcgtagta   120
tgtactactt ccatcatagc taatatgtcc gacccactgc agccccttct tttgagcctg   180
gcggacccag ctcatgccat agctactgaa ggtgaatcca gaggcctgac aggagagacc   240
cagggaaccc ccaggattca ccatgtgtcc tccaaactcc accagttgct cctc          294
```

<210> SEQ ID NO 9
<211> LENGTH: 294
<212> TYPE: DNA
<213> ORGANISM: Canis familiaris

<400> SEQUENCE: 9

```
actcgcacag taatacacgg ccgtgtcctc ggctctcagg ctgttcatct gcagatacgc    60
catgttcttg gcgttgtctc tggagatggt gaatcggccc tttacagctt ctgcatagta   120
tgtggtactt ccactctcat aaatccttgc gacccactcc agccctttcc ctggagcctg   180
gcggacccag tacatttcgt agttactgaa ggtgaatcca gaggccacac aggagagtct   240
cagggacccc ccaggcttca ccaggtctcc cccagactcc accagctgca cctc          294
```

<210> SEQ ID NO 10
<211> LENGTH: 294
<212> TYPE: DNA
<213> ORGANISM: Canis familiaris

<400> SEQUENCE: 10

```
ccttgcacag taatacacgg ccgtgtcctc ggctctcagg ctgttcatct gcagatacag    60
cgtgttcttg gcgttgtctc tggagatggt gaatcggccc ttcacagcgt ctgcgtagta   120
tgtgctactt ccactactgc taatttctga gagccactgc agccccttcc ctggagcctg   180
gcggacccag tccatgtcat agctactgaa ggtgaatcca gaggccacac aggaaagtct   240
cagggacccc ccaggcttca ccaggtctcc tccagactcc accagctgca cctc          294
```

<210> SEQ ID NO 11
<211> LENGTH: 294
<212> TYPE: DNA
<213> ORGANISM: Canis familiaris

<400> SEQUENCE: 11

```
actcacacag taatacacgg ccatgtcctt gtctctcagg ctgttcatct gcagatagag    60
cgtgttcctg gcgttgtctc tggagatggt gaattggccc ttcacagcgt ctgcatacct   120
tgtgctactt ccaccattgc taatgtatgt gacccactgt aacccttttcc ctggagcctg   180
gtagacccag tccatgtcgt agctactgaa ggtgaatcca gaggccacac aggaaagtct   240
cagggatccc ccaggcttca ccaggtctcc ctcagtctcc accagctgca cctc          294
```

<210> SEQ ID NO 12
<211> LENGTH: 294
<212> TYPE: DNA
<213> ORGANISM: Canis familiaris

<400> SEQUENCE: 12

```
tttcacacaa taatacacag ccgtgtcctc ggctcccagg ctgttcatct gcagatacag    60
cgtgttcttg gcattgtctc tggagatggt gaatcggccc ttcacagcgt ctgcatagct   120
tgtgctactt ctatcattgg taatacctgc gacccactgc agccccttcc ctggagccta   180
```

```
gtggacccag cccatgtagt agctactgaa ggtgaatcta gaggccacac aggagaggga    240
cctccccagg cttcaccacg tctcccctag actccaccag ctgcacctca ccct          294
```

<210> SEQ ID NO 13
<211> LENGTH: 294
<212> TYPE: DNA
<213> ORGANISM: Canis familiaris

<400> SEQUENCE: 13

```
cttcccacag taatacacag ctgtgtcctc ggctctcagg ctgttcatct gcagatacag    60
cgtgttcttg gcattgtctc tggagatggt gaatcggccc ttcacagcgt ctgcatagta    120
tgtgctactt ccaccactgt taatgtatcc gacccactgc agccccttcc ctggagcctg    180
gcggacccag ctcatgtagt agctactgaa ggtgaatcca gaggccacac aggagagtct    240
cagagacccc ccaggcttca ccaggtctcc ccagactcca ccagctgcac ctca          294
```

<210> SEQ ID NO 14
<211> LENGTH: 294
<212> TYPE: DNA
<213> ORGANISM: Canis familiaris

<400> SEQUENCE: 14

```
cctcatgcag taatacacgg ctgtgtcctc ggctctcagg ctgttcatct gcagatacag    60
catgttcttg gtgttgtctc tggagatggt gaatctgtcc ctcacagtgt ctgtgtagta    120
tgtgctactt ccatcatagc taatatgtcc gacccactgc agccccttct tttgagcctg    180
gcggacccag ctcatgccat agctactgaa ggtgaatcca gaggcctgac aggagagacc    240
cagggaaccc ccaggattca ccatgtgtcc tccaaactcc accagttgct cctc          294
```

<210> SEQ ID NO 15
<211> LENGTH: 294
<212> TYPE: DNA
<213> ORGANISM: Canis familiaris

<400> SEQUENCE: 15

```
actcacacag taatacacgg ccgtgtccta ggctctcagg ctgttcatct gcagatacac    60
catgttcttg gcgttgtctc tggagatggt gaatcggccc tttacagctt ctgcgtagta    120
tgtggtactt ccactctcat aaatccttgc gacccactcc agccctttcc ctggagcctg    180
gtggacccag tacattttgt agttactgaa ggtgaatcca gaggccacac aggagagtct    240
cagggatccc ccaggcttca ccaggtctcc cccagactcc accatctgca cctc          294
```

<210> SEQ ID NO 16
<211> LENGTH: 294
<212> TYPE: DNA
<213> ORGANISM: Canis familiaris

<400> SEQUENCE: 16

```
tctcgcacag taataaaggg ctgtgtcctc cactgtcagg ctgttcatct gcagatacag    60
tgtgttcttg gcgttgtctc tggagatggt gaatcggccc ttcacagcgt ctgggtagta    120
tgtgctactt ccatctttgt taatatatcc gacccactga ttgcccttcc ctggtgcctg    180
gcggatccaa acatgtagt aactactaaa ggtgaatcca gaggccacac aggagagtct    240
cagggacccc ccaggcttca ccaggtctcc tccagactcc accagctgta cctc          294
```

<210> SEQ ID NO 17

```
<211> LENGTH: 294
<212> TYPE: DNA
<213> ORGANISM: Canis familiaris

<400> SEQUENCE: 17
cttcgcacag taatacacgg ctgtgtcctc agttctcagg ctgttcatct gcagatacag      60
cgtgttcttg gcattgtctc tggagatggt gaatcggccc ttcacagcgt ctgtgtaact     120
tgtgctcctt ccatcactgc taatgtatgc gacccactgc agccccttcc ctggagcctg     180
gcggacccag ctcatgtcgt agctactgaa ggtgaagcca gagaccacac aggagagtct     240
cagggacccc tcaggtttca caaggtctcc cccagactcc accagctgca cctc           294

<210> SEQ ID NO 18
<211> LENGTH: 294
<212> TYPE: DNA
<213> ORGANISM: Canis familiaris

<400> SEQUENCE: 18
ctttgcacag taatacatgg ccgtgtcctc ggctctcagg ctgttcatct gcagatacac      60
tgtgttcttg gcgttgtctc tggagatggt gaatcggccc ttcacagcgt ctgtgtagta     120
tgtgctactt ccaccgctgt taataccctgc gaccaactgc agccccttct caggagcctg    180
gcggacccag ctcatgctgt agctactgaa ggtgaatcca gaggccacac aggacagtct     240
cagggacccc gcaggcttca ccaggtctcc cccagactcc accagctgca cctc           294

<210> SEQ ID NO 19
<211> LENGTH: 294
<212> TYPE: DNA
<213> ORGANISM: Canis familiaris

<400> SEQUENCE: 19
cacctgcaca gtaatacacc gctgtgtcct cactctcagg ctgttcatct gcagatacag      60
tgtgttcttg gcattgtctc tggaggtggt gaatcagccc ttcacagcgt ctgtgtacct     120
agtgctactt ccaccactgt tactgtatgc gactcactgc agccccttc ctggagcctg      180
gcagacccat cacatgcagt agatactgaa ggtgaatcca gaggacacag aggagagtct     240
caggaccctc caggcttcac caggtatccc ccagactcca ccagctgcac ctca           294

<210> SEQ ID NO 20
<211> LENGTH: 300
<212> TYPE: DNA
<213> ORGANISM: Canis familiaris

<400> SEQUENCE: 20
actctcacag taatacacgg ccgtgtcctc agctctcaag ctgttcatct gcaggtacag      60
cgtgttcttg gcattgtctc tggagatggt gaatcggccc ttcacagtgt ctgtgtagta    120
tgtgctcctt ccatcttagc taatagctgc gaccaactgt agccccttcc ccaaagcctg    180
gcagacccag ctcatgccat acttactgaa ggtgaatcca gagaccacac aggacagtct    240
gcagacccag ctcatgccat acttactgaa ggtgaatcca gagaccacac aggacagtct    300

<210> SEQ ID NO 21
<211> LENGTH: 294
<212> TYPE: DNA
<213> ORGANISM: Canis familiaris

<400> SEQUENCE: 21
cctcaatgtg tcactcacat aataatacag ggctctcagg ctgttcatat gcagatacag      60
```

```
cgtgttccttg gcattgtctc tggagatggt gaatcacccc ttcacagcat ctgcatagct      120 tttctgctt ccaccagtat taacccatat gacccactgc agccccttcc ctggagcctg       180
gctgacccag ctcatccagt agctcctgaa ggtgaatcca gaggtcacat aggagagtct      240
aattgatccc ccaggcttca ccaggtctcc cccagactcc actagcttca cctc            294
```

<210> SEQ ID NO 22
<211> LENGTH: 294
<212> TYPE: DNA
<213> ORGANISM: Canis familiaris

<400> SEQUENCE: 22

```
gtctgcacag taatacatgg ccatgtcctc ggctctcagg ctgttcatct gcagatagag      60
cgtgttcttg gcgttgtctc tggagatggt gaatcagccc ttcagagcgt ctacgtagct      120
tgtgctactt ccatctgtgc taataccgtc gacccactgc agccccttcc ccggagtttg     180
gtggatccag tacatccagt agctactgaa ggtgaatcca gaggccacac aggaggtctc      240
agggatcctg caggcttcat cagttctccc ccagactcca tcatctgcac ctca            294
```

<210> SEQ ID NO 23
<211> LENGTH: 294
<212> TYPE: DNA
<213> ORGANISM: Canis familiaris

<400> SEQUENCE: 23

```
cttcgcacag gaatacacgg ctgtgtcctc ggctctcagg ctgttcatct gcagatacag      60
cgtgttcttg gcattgtctc tggagatggt gaatcggccc ttcacagcgt ctgcatacct      120
tgtgctactt ccatcatacc taatcaatga gaccccctgc agccccttcc ctggagcctg     180
gcggacccag ctcatgccgt agctactgaa ggtgaatcca gaggccacac aggacagtct      240
cagggatccc ccaggcttct ccaggtctcc cccagactcc accagctgca cctc            294
```

<210> SEQ ID NO 24
<211> LENGTH: 294
<212> TYPE: DNA
<213> ORGANISM: Canis familiaris

<400> SEQUENCE: 24

```
ccttgcacaa taatatacgg ccatgtcctc ggctctcagg ctgttcatct gcagatacag      60
catgttcttg gcattgtctc tggagatggt gaatcggccc ttcacaatgt ctgcgtagct      120
tgtgctactt ccactactgc taatttctgc aacccactgt agccccttcc ttggagcctg     180
gcagaaccag ctcatgtaga agctactgaa ggtgaatcca gaggccacac aggagagtct      240
cagggacccc tcaggcttca caaggtctcc cccagactcc accagctgca cctc            294
```

<210> SEQ ID NO 25
<211> LENGTH: 294
<212> TYPE: DNA
<213> ORGANISM: Canis familiaris

<400> SEQUENCE: 25

```
cttcacacag taatacacgg ccgtgtcctc ggatctcagg ctgttcatct gcagatacag      60
cgtgttcttg acattgtctc tggagatggt gaattcaccc ttcacagcat ctgtgtagct      120
tgtgctactt ccaccgctgt taaaaccgtc gacccactgc atccccttcc ctggaggctg     180
gtgagcccag cccatgttgt agctactgaa ggtgaatcca gggaccacac aggagagtct      240
```

-continued caggacgcc ccaggcttca ccagttctcc cccaggctcc accagctgca cctc       294

<210> SEQ ID NO 26
<211> LENGTH: 294
<212> TYPE: DNA
<213> ORGANISM: Canis familiaris

<400> SEQUENCE: 26
ccttgcacag taatacatgg ccgtgtcctc ggctctcagg ctgttcatct gcagatacag      60
cgtgttcttg gcattgtctc tggagatgat gaatcggccc ttcacagcgt ctgcatagtt     120
tgtgctactt ccactaccgc taatttctgc aacccactgt agcccctttcc ctggagcctg    180
gcggacccag ctcatccagt agctactgaa ggtgaatcca gagcccacac aggagagtct    240
cagggacccc ccaggcttca ccaggtctcc cccagactcc accagctaca cctc           294

<210> SEQ ID NO 27
<211> LENGTH: 294
<212> TYPE: DNA
<213> ORGANISM: Canis familiaris

<400> SEQUENCE: 27
gcacagtaat acacggccgt gtcctccctc ggctctcagg ctgttcttct acagatacag      60
tgtgtttttg gcattgtctc tggagatggt gaatcggccc ttcagagcgt ctgcgtagct     120
tgtgctactt ccatcatatc taatacctgc accccctgt agcccatcc cgggagcctc      180
acgggcccac cacatgctgt agctactgaa ggtgaatcca gagcccacac aggagagtct    240
cagggacctc ctaggcttca ccacgtctcc cgcagactcc accagatgca cctt           294

<210> SEQ ID NO 28
<211> LENGTH: 294
<212> TYPE: DNA
<213> ORGANISM: Canis familiaris

<400> SEQUENCE: 28
cctcacacag taatacacgg ccgtgtcctc ggctctcagg ctgttcatct gcagatacag      60
cgtgttcttg gcgttgtctc tagaaacagt gaatcggcct ttcacagctt ctgcgtagct     120
tgtgctactt ccatcatacc taatccatgc gacccatgga gccccttccc tggagcctgg    180
tggacccagt acatccagta gctactgaag gtgaatccag agcccacaca ggagactctc    240
agggaccccc ccagacttca ccaggtctcc cccagactcc actagctgca cctc           294

<210> SEQ ID NO 29
<211> LENGTH: 294
<212> TYPE: DNA
<213> ORGANISM: Canis familiaris

<400> SEQUENCE: 29
cctcacacag taatacaggg ccgtgtcatc ggctcccagg ctgctcatct gtagatacag      60
cgtgttcttg gtgttgtctc tggagatggt aaatcggccc tttactgtgt ctgcgtgatt     120
tgtgctactt ccactattgc taatagttgt gatccactgc agccccttcc ttggagcctg    180
gcggacccag atcatgctgt agttactgaa ggtgaatccg gaagccacac aggagacagg    240
agagtctcag gaaacctcca gtcttcacca ggtctcccca ggactccacc agct           294

<210> SEQ ID NO 30
<211> LENGTH: 294
<212> TYPE: DNA
<213> ORGANISM: Canis familiaris

<400> SEQUENCE: 30

```
cttcgcacag taatacacgg ccgtgtcctc ggctctcagg ctgttcatct gcaaatacag        60
cgagttcttg acgttgtctc tggagatggt gaatcggccc ttcacagcgt cagtgtagta       120
tgtgctacct ccactgtcac taatatctgc gaccccactgc agccccttcc caggagcctg      180
gcggatccag ctcatgtagt agctactgaa ggtgaatcca gaggccacac aggagagtct       240
cagggacccc ccaggcttca ccagttctcc cccagactcc accagctgca cctc             294
```

<210> SEQ ID NO 31
<211> LENGTH: 294
<212> TYPE: DNA
<213> ORGANISM: Canis familiaris

<400> SEQUENCE: 31

```
acccgcacag taatacacgg cggtgtcctc ggctctcagg ctgttcatct gcagatatag        60
cgtgttcttg acgttgtctc tggagatgat gaatcgaccc ttcacagcat ctgcggagct       120
tgtgctactt ccaccactgt taatgtatgc gacccactgc acccccttcc ctggagcctg       180
acagacccat tgcatgctgt agctactgaa ggtgaatcca taggccacac aggagagtgt       240
cagggacccc ccaggcttca ccaggtctcc cccagactcc accagctgca cccc             294
```

<210> SEQ ID NO 32
<211> LENGTH: 294
<212> TYPE: DNA
<213> ORGANISM: Canis familiaris

<400> SEQUENCE: 32

```
tcccacacag taatatacgg ccgtgtcctc ggctctcagg cagttcatct gcagatacag        60
cgtgttcttg gcattgtctc tggagatggt gaatcggccc ttcacagcgt ctgcatagta       120
tgtgctactt ccaccactgt taatgtatgc aacccactgc aaccctttcc ctggagcctg       180
gccgacccag ctcatccaat agctactgaa ggtaaatcca gaggccacac agaagagtct       240
cagggacccc ccaagcttca ccaggtctcc cccagcctcc accagctgca tctc             294
```

<210> SEQ ID NO 33
<211> LENGTH: 294
<212> TYPE: DNA
<213> ORGANISM: Canis familiaris

<400> SEQUENCE: 33

```
acccgcacag taatacatgg ccgtgtcctc ggctctcagg ctgttcatct gaagatacag        60
cgtgttcttg gcgttgtctc tggagatggt gaaccggccc ttcacagcat ctgcatagta       120
tgtgctactt ccaccactgc taatgtatgc gacccactgc agccccttcc ctggagcctg       180
gcggacccag ttcatgtcat agctactgaa ggtgaatcca gaggccacac aggagagtct       240
cagggatccc acaggcttca ccaggtctcc cccagactcc accagctgca cctc             294
```

<210> SEQ ID NO 34
<211> LENGTH: 293
<212> TYPE: DNA
<213> ORGANISM: Canis familiaris

<400> SEQUENCE: 34

```
attcacacag taatacatgg ccatgtcctc agctctcagg ctgttcatct gcagatacag        60
catgttcttg gcattgtctc tggagatggt gaatcggccc ttcacagcgt ctgcatagct       120
```

```
catgttactt ccactagaat aaattcatgc gactcacggc agccccttcc caggagcctt    180
gtggacccag ctcatggtat aggaaatgaa ggtgaatcca gaggccacac gggcgagtcc    240
agggacctct caggcttcac caggtctccc ccagactccg ccagctgccc ctc           293
```

<210> SEQ ID NO 35
<211> LENGTH: 294
<212> TYPE: DNA
<213> ORGANISM: Canis familiaris

<400> SEQUENCE: 35

```
attcacacag taatacatgg ccatgtcctc agctctcagg ctgttcatct gcagatacag     60
catgttcttg gcattgtctc tggagatggt gaatcggccc ttcacagcgt ctgcatagct    120
catgttactt ccactagaat aaattcatgc gactcacggc agccccttcc caggagcctt    180
gtggacccag ctcatggtat aggaaatgaa ggtgaatcca gaggccacac gggcgagtct    240
cagggacctc tcaggcttca ccaggtctcc cccagactcc gccagctgcc cctc          294
```

<210> SEQ ID NO 36
<211> LENGTH: 294
<212> TYPE: DNA
<213> ORGANISM: Canis familiaris

<400> SEQUENCE: 36

```
gtctgcacag taatatatgg ccgtgtcctc ggctctcagg ctgttcatct gcagatacag     60
cgtgttcttg acattgtctc tggagatggt gaatcggccc ttcacagtgt ctgcatacct    120
tgagatactt ccatcatacc taatccatga gacccactgc agccctgcc ctggagcctg    180 gtggacccag ctcatttcac tgctactgaa ggtgaatcca gaggccacac aggagagtct    240
cagggaccct ccaggcttca ccaaatcttc cccagactcc accagctgta cctc          294
```

<210> SEQ ID NO 37
<211> LENGTH: 294
<212> TYPE: DNA
<213> ORGANISM: Canis familiaris

<400> SEQUENCE: 37

```
cttcgcacag taatacacgg ccgtgtcctc ggctctcagg ctgttcatct gcagatacag     60
cgtgttcttg gcgttgtctc tggagatggt gaatcggccc ttcacagcgt ctgcgtagta    120
tgtgctactt ccatcattcc aaataactgc gacccactgc agcccttcc ctggagactg    180 acggacccag ctcatgtcat agctactaaa ggtgaatcca gaggccacac aggacagtct    240
caaggtcccc ccaggcttca ccaggtctcc cccagactcc accagctgca cctc          294
```

<210> SEQ ID NO 38
<211> LENGTH: 294
<212> TYPE: DNA
<213> ORGANISM: Canis familiaris

<400> SEQUENCE: 38

```
cttcgcacag taatacacgg ctgtgtcctc ggctctcagg ctgttcatct gaagatacag     60
cttgttcttg gcgttctctc tggagatggt gaaccggccc ttcacagcgt ctgcgtagcc    120
tgtgctacct ccactatcac taatatctgc gacccactgc agccccttcc caggagcctg    180
gcggatccag ctcatgtagt agctactgaa ggtgaatccc gaggccacac aggagagtct    240
cagggaaccc ccaggcttca cgaggtctcc cccagattcc accagctgta cctc          294
```

<210> SEQ ID NO 39
<211> LENGTH: 294
<212> TYPE: DNA
<213> ORGANISM: Canis familiaris

<400> SEQUENCE: 39

```
cttcgcacag taatacacag ccgtgtcctc ggctctcagg ctgttcatct gcagatacac    60
tgtgttcctg gcgttgtctc tggagatggt gaatcggccc ttcacagcgt cagtgtagta   120
tgtgctactt ccatcatagc taatagctgc gacccactgc agccccttcc caggagcctg   180
gcggacccag ctcatgtcgt agttactgaa ggtgaatcca gaggctacac aggagagtct   240
cagggacccc ccaggcttca ccaggtctcc cccagactcc accagctgca cctc          294
```

<210> SEQ ID NO 40
<211> LENGTH: 294
<212> TYPE: DNA
<213> ORGANISM: Canis familiaris

<400> SEQUENCE: 40

```
cttcccacag taatacacag caatatcctc agctctcagg ctgttcatct gcagatacac    60
catgttcttg gcgttgtcta tggagatggt gaatcggccc ttcacagcat ctacgtagta   120
tgtgctactt ccactactgc taatagctgc aacccactgc aggcccttcc ctggagcctg   180
gccgacccag ctcatggcat acctactgaa ggtgaatcca gaggtcacac aggagagtct   240
cagggacccc cctggcttca ccaggtcttc cccagactc caccagctgc actt           294
```

<210> SEQ ID NO 41
<211> LENGTH: 294
<212> TYPE: DNA
<213> ORGANISM: Canis familiaris

<400> SEQUENCE: 41

```
actcgcacag taatacacgg ccgtgtcctc agctctcaag ctgttcatct gcaggtacag    60
cgtgttcttg ccattgtctc tggagatggt gaatcggccc ttcacagtgt ctgtgtagta   120
tgtgctcctt ccatcatagc taatagctgc gacccactgc agccccttcc ctgaagcctg   180
gcagacccag ctcatgccat agctcctgaa ggtgaatcca gaggcacac aggacagtct    240
cagggaaccc ccaggcttca tcaggtctcc cccagactcc accagctaca cctt          294
```

<210> SEQ ID NO 42
<211> LENGTH: 294
<212> TYPE: DNA
<213> ORGANISM: Canis familiaris

<400> SEQUENCE: 42

```
cctcgcacag taatacacgg ccgtgtcttc ggctctcagg ttgttcatct gcagatacag    60
cgtgttcttg gcgttgtctc tggagatggt gaatcgaccc ttcacagcgt ctgtgtacca   120
tgtgctactt ccaccactgt taatgtacgc gacccactgc agctccttcc ctggagcctg   180
gcggacacag ctcatccaat agctactgaa ggtgaatcca gaagtcacac atgagagtct   240
cagggaaccc ccaggcttca ccaggtctcc cccagactcc accagctgca cctc          294
```

<210> SEQ ID NO 43
<211> LENGTH: 294
<212> TYPE: DNA
<213> ORGANISM: Canis familiaris

<400> SEQUENCE: 43
atctgcacag taatacaggg ctatgtcctg agctctcagg ctgttcatct gtagataaag    60
catgttcttg gctttgtctc tggagatggt gaatcgaccc ttcacagcgt ctgcatagta   120
tgtgctgctt ccattactgc taatgtatgt gacccactgt agccccatcc caggagactg   180
acggagacaa tgcatgctgt agctactgaa ggtgaacctt gaggcacac aggagagtct    240 ctgggacccc ccaggtttca ctcggtctcc cccagactcc agcagctgta cttc          294

<210> SEQ ID NO 44
<211> LENGTH: 294
<212> TYPE: DNA
<213> ORGANISM: Canis familiaris

<400> SEQUENCE: 44
gtctgcacag taatatatgg ccgtgtcctc ggctctcagg ctgttcatct gcagatacag    60
cgtgttcttg gcattgtctc tggagatggt gaatcggccc ttcacagtgt ctgcatacct   120
tgagctactt ccatcatacc taatccatga gacccactgc agccctgcc ctggagcctg    180 gtggacccag ctcatttcac tgctactgaa ggtgaatcca gaggcacac aggagagtct    240 cagggaccct ccaggcttca ccaaatcttc cccagactcc accagctgta cctc           294

<210> SEQ ID NO 45
<211> LENGTH: 294
<212> TYPE: DNA
<213> ORGANISM: Canis familiaris

<400> SEQUENCE: 45
gtccacacag taatacacag ctgtgtcctc ggctctcagg ctgttcatct gcagatacac    60
tgtgttcctg gcgttgtctc tggagatggt gaatcggccc ttcacagcgt cagtgtagta   120
tgtgctactt ccatcatagc taatagctgt gacccactgc agccccttcc caggagcctg   180
gcggacccag ctcatgctgt agctactgaa ggttaatcca gaggccacac aggagagtct   240
cagggacccc ccaggcttcg ccaggtctcc cccagactcc accagctgca cctc            294

<210> SEQ ID NO 46
<211> LENGTH: 294
<212> TYPE: DNA
<213> ORGANISM: Canis familiaris

<400> SEQUENCE: 46
gtgtgcacag taatacacag ccgtgtcctc agctctcagg ctgttcatct gcagatacag    60
cgtgttcttg gcattgtctc tggagatggt gaatcggccc ttcacagcat ctgcgtggta   120
tgtggtactt ccatctttgt taattactga gactcagtgc agcccttccc ctggagcttg   180
gcggacccag cttatccagt aactactgaa agtgaatgca gagctacaa aggagagtct    240 cagggacccc ccaggcttca ccagctctcc cccagattcc accagtggca cctc            294

<210> SEQ ID NO 47
<211> LENGTH: 293
<212> TYPE: DNA
<213> ORGANISM: Canis familiaris

<400> SEQUENCE: 47
cctcgcacag caatgcacgg ctgtgtcctc agctctcagg ctgttcatct gcagatacag    60
catgttcctg gtgctgtctc tggagatggt gaatcagccc tttacagcgt ctgcatagta   120
catgctactt ccattactgc tattggatat gacccactgt agccactacc gggagactgg   180
tggagccaat gtatgctgtt gctatgaaag gtgaatgtag aggactcaca gaagagtcta   240

```
gggacccgcc aggcttcacc aggtctcccc tagatttcac caactgctcc tca        293
```

<210> SEQ ID NO 48
<211> LENGTH: 294
<212> TYPE: DNA
<213> ORGANISM: Canis familiaris

<400> SEQUENCE: 48

```
tccctcgcac agtaatacat ggccttgtcc tcagctctca ggctgttcat ctgcagaaac    60
actgtgttct ggcgttctc tggagatggt gaatcggccc ttcacagcat ctgtgtagct   120
tgtgctattt ccactagctt aaatccatgc gacccactga atccccttcc cgggagcctg   180
gcggacccag ctcatgctgt agctactgaa ggtgaatcca gcggccacac aggagagtct   240
cagggacccc ccaggcttca tgaggtctcc cccagactcc accagctgca cctc         294
```

<210> SEQ ID NO 49
<211> LENGTH: 294
<212> TYPE: DNA
<213> ORGANISM: Canis familiaris

<400> SEQUENCE: 49

```
cttcgcacag taatacacgg ctgtgtcctc agctctcagg ctgttcatct gcagatacag    60
cgtgttcttg gcgttgtctc tggagatggt gaatcggccc ttcacagcat ctgcgtagcc   120
tgtgctcctt ccatcattgc taatccgtgt gagccactgc agccccttcc ctggagcctg   180
gcggacccag tccatgtcgt tgctactgaa ggtgaaacca gaggccacac aggagagtct   240
caaggacccc ccaggcttca ccaggtctcc cccagactcc accagctgca cctc         294
```

<210> SEQ ID NO 50
<211> LENGTH: 294
<212> TYPE: DNA
<213> ORGANISM: Canis familiaris

<400> SEQUENCE: 50

```
cttcgcacag taatacatgg ccgtgtcctc agctctcagg ctgttcatct gtagatacag    60
catgttcttg gcgttgtctc tggagatggt gaatcggccc ttcacagcgt ctgcgtagtt   120
tgtgctactt ccatccctgc taataactgc gacccactgc agccccttcc ctggagcctg   180
gcggacccag tgcatggcat agctactgaa agtgaatccg gaggtcacac aggacagtct   240
tagggaaccc caggcttcac caggtctccc ccagactcct ccagctgcac ctca         294
```

<210> SEQ ID NO 51
<211> LENGTH: 294
<212> TYPE: DNA
<213> ORGANISM: Canis familiaris

<400> SEQUENCE: 51

```
catcgcacag taatataggg ccgtgtcctc ggctctcagg ctggtcatct gcagatacag    60
agtgttcttg gaattgtctc tggagatggt gaatcggccc ttcacagcat cagtgtagta   120
tgtgctactt ccatcactcc taattcatgc gaaccactgc agccccttcc ctggagcctg   180
gtggacccag tgcatgtagt agatactgaa ggtgaatccg gaggccacac aggacagtct   240
cagggacccc ccaggcttca ccagctctcc cccatactcc accagctgca cttc         294
```

<210> SEQ ID NO 52
<211> LENGTH: 294
<212> TYPE: DNA

<213> ORGANISM: Canis familiaris

<400> SEQUENCE: 52

```
actcacacag taatacacgg ccgtgtcttc ggctctcagg ctgttcacct gcaggtacag    60
cgtgttcttg gcattgtctc tggagatggt gaatgggccc ctcacagcgt ctgcatagtt   120
tgtgctactt ccagtactgc taatttctgc aagccactgc agcccatcc ctggagcctg    180
gtggacccag tacatccagt agctactgaa ggtgaatcca ggtccacac aggagagtct    240
cagggacccc ccaggcttca ccaggcctcc ctagactcca ccagctgcat ctca         294
```

<210> SEQ ID NO 53
<211> LENGTH: 294
<212> TYPE: DNA
<213> ORGANISM: Canis familiaris

<400> SEQUENCE: 53

```
cttcacacag taatacacgg ccgtgtcctc ggctctcagg ctgttcatct gcagatacag    60
cgtgttcttg gcattgtctc tggagatggt gaatcggccc ttcacagcgt ctgcatagct   120
tgtgctactt ccatcactgc taatgtatcc gacccactgc agccccttcc ctggagcctg   180
gcggacccag ttcatgtagt tgctactgat agtgaatccg gaggccacac aggagagtct   240
cagggacccc ccaggcttca tcaggtctcc cccagactcc accagctgca cctc         294
```

<210> SEQ ID NO 54
<211> LENGTH: 294
<212> TYPE: DNA
<213> ORGANISM: Canis familiaris

<400> SEQUENCE: 54

```
actcacacag taatacgcgg tcatgtcctg ggctctcagg ctgttcatct gcagatacag    60
catgttcttg gcattgtctc tgaagatggt gaattggccc ttcactgtgt ctgcatagta   120
tgtgctacct ccaccactgt taataattgc aacccacccc aacccttcc ctggagcctg    180
gcagacccaa tgcatccagt agctactgaa ggtgaatcca gaggccacac aagagagtct   240
cagagactcc ccaggcttca ccaggtttcc ccagactcca ccagctgcac ctca         294
```

<210> SEQ ID NO 55
<211> LENGTH: 296
<212> TYPE: DNA
<213> ORGANISM: Canis familiaris

<400> SEQUENCE: 55

```
gggaggtttg tgtctgggct cacacttagg tcacctcact gtgtccttcg cacagtaata    60
cacggccgtc ttggcattgt ctctggagat ggtgaatcgg cccttcacag cgtctgtgta   120
gtatgtgcta cttccgtcac tgctaatccg tgcgacccac ttcagcccct ccctggagcc   180
tggcagaccc attccatata gtagctactg aaggtgaatc cagaggccac acaggagagt   240
ctcagggatc cccaggctt caccaggtct cccccagatt ccaccagctg cacctc        296
```

<210> SEQ ID NO 56
<211> LENGTH: 294
<212> TYPE: DNA
<213> ORGANISM: Canis familiaris

<400> SEQUENCE: 56

```
ccttgcacag taatataggg ccgtatcatc agctctcagg ctgttcatct gcagatacag    60
agtgttcttg gaattgtctc tggagatggt gaatctgccc ttcacagcgt ctgggtagct   120
```

```
tgtgctactt ccatcactcc taattcttgc aacccactgc agccccttcc ctggagcctg      180
cagacccagt gcatgtagta gctactgaag gtgaatccag aggccacaca ggacagtctc      240
agggaacccc caggcttcac cagctctccc ccagactcca caagctgcac ttca            294
```

<210> SEQ ID NO 57
<211> LENGTH: 294
<212> TYPE: DNA
<213> ORGANISM: Canis familiaris

<400> SEQUENCE: 57

```
cttcgcacag taatacacgg ctgtgtcctc agctctcagg ctgttcatct gcagatacag       60
cgtgttcttg gcattgtctc tggagatggt gaatcggccc ttcacagtgt ctgcggagcc      120
tgtgctactt ccactactgc taataactgc tacccacttc agccccttcc ctggagcctg      180
gcggacccag ctcttggcat ggctactgaa ggtgaatccg gaggccacac aagagagtct      240
cagggatccc ccaggcttca ccaggtctcc cccagactcc accagctgca cctc            294
```

<210> SEQ ID NO 58
<211> LENGTH: 293
<212> TYPE: DNA
<213> ORGANISM: Canis familiaris

<400> SEQUENCE: 58

```
ccgcaatgtg tcactcacac aataatacag ggctatcagg ctgttcatat gcagatacag       60
cgtgttcttg gcattgtctc tggagatggt gaattgcccc ttcacagcat ctgcatagct      120
tttgctgctt ccaccagtat taacccatgt gacccactgc agccccttcc ctggagcctg      180
gctgacccag ctcatccagt agctcctgaa ggtgaatcca gaggtcacat aggagagtta      240
attgatcccc caggcttcaa caggtctccc ccagactcca ccagcttcac ctc             293
```

<210> SEQ ID NO 59
<211> LENGTH: 294
<212> TYPE: DNA
<213> ORGANISM: Canis familiaris

<400> SEQUENCE: 59

```
cctcgcacag taatacacgg gcatgtcctc agctctcagg ctgttcatct gcagatacag       60
cgtgttcttg gcattgtctc tggagatggt gaatcggccc ttcacagcgt cagtgtagta      120
tgtgctactt ccatcagtgg taatagctgc gacccactgc agccccttcc caggagcctc      180
gtggacccag taaatggcat agctatagaa ggttaatcca gaggccacac aggacagtct      240
cagggaaccc ccaggcttca ccaggtttcc accagactcc accagctgca cctc            294
```

<210> SEQ ID NO 60
<211> LENGTH: 294
<212> TYPE: DNA
<213> ORGANISM: Canis familiaris

<400> SEQUENCE: 60

```
gtctgcacag taatacagag ccgtgtcctc agctctcagg ctgttcatct gaagatacag       60
catgttcttg gcgttgtctc tggagatggt gaatcggccc ttcacagcgt ctttgtaacc      120
tgtgctactt ccatcatagc taatgtatgc aacacactgc agccctttcc tggagcctaa      180
tggacccagc tcatgtcaca gttactgaag gtgaatcaag gggccacaca ggagagtctc      240
agggaccccc cagacttcac cagatctccc cgagactcca ccagctgctc ctca            294
```

<210> SEQ ID NO 61
<211> LENGTH: 294
<212> TYPE: DNA
<213> ORGANISM: Canis familiaris

<400> SEQUENCE: 61

```
cctcgcacag caatgcacgg ctgtgtcctc agctctcagg ttattcatct gcagatacag      60
catgttcctg gtgttgtctc tggagatggt gtatcagccc tttacagcgt ctgcatagta     120
catgctactt ccattactgc tattggatat gacccactgt agccactacc gggagactgg     180
tggagccaat gcatgctgta gctatgaaag gtgaacgtag aggactcaca gaagagtctc     240
agggacccgc caggcttcac caggtctccc ctagatttca ccaactgctc ctca           294
```

<210> SEQ ID NO 62
<211> LENGTH: 294
<212> TYPE: DNA
<213> ORGANISM: Canis familiaris

<400> SEQUENCE: 62

```
gtgtcccctg cacaggaata catggccgtg tcctcagctc tcaggcatct gcagaaacag      60
tgtgttcttg gcgttgtctc tggagatggt gaatcggccc ttcacagcgt ctgcgtagct     120
tgtgctactt ccgctagcat atatccatgc gacccactgc atcccttcc cgggagcctg      180
gcggacccag ctcatgctgt agctactgaa ggtgaatcca gcggcacac aggagagtct      240
cagggacccc ccaggcttca cggggtctcc cgcagactcc accagctgca cctc           294
```

<210> SEQ ID NO 63
<211> LENGTH: 294
<212> TYPE: DNA
<213> ORGANISM: Canis familiaris

<400> SEQUENCE: 63

```
gtctgcacag taatacaagg ccgtgtcctc ggctctcagg ctgttcatct gcagatagag      60
cgtgttcttg gcattgtctc tggagatggt gaatcggccc ttcacagcat ctgtgtagta     120
tgtgctactt ccactattgc taattttgc gacccactgc agcccttccc aggagcctgg     180
cggacacagc tcatgctgta gctactgaag tgaatccaga ggccatacag gacagtctca     240
gggaccgccc aggcttcacc aggtctccgc cagactccac cagctgcacc tcac           294
```

<210> SEQ ID NO 64
<211> LENGTH: 294
<212> TYPE: DNA
<213> ORGANISM: Canis familiaris

<400> SEQUENCE: 64

```
ctttgcacag taatacatag ccgtgtcctc ggctctcagg ctgttcatct gcagatacag      60
cgtgttcttg gcattgtctc tggagatggt gaatcggccc ttcacagcgt ctgcgtagta     120
tgtgctactt ccatcactgc taatccgtgc gacccactga agcccttccc ctggagcctg     180
gcggacccag tacatgtagt agctactgaa ggtgaatcca gaggccacac aggacagtct     240
cagggacccc ccaggcttca ccaggtctcc cccagactcc accagctgca cctc           294
```

<210> SEQ ID NO 65
<211> LENGTH: 291
<212> TYPE: DNA
<213> ORGANISM: Canis familiaris

<400> SEQUENCE: 65

```
ttgcacaggg atatagggcc gtgtccttgg ctctcaggct gttcatctgc agatacagaa    60
tgttcttgga attgtctttg gagatggtgt atcggtcctt cacagcatca gtgtatatgt   120
gctacttcca tcactcctaa ttcatgtgac ccacagcagc catttccctg gagcctggcg   180
gacccagtac atgtagtagc tactgaaggt gaatccagag ccacacagg agagtctcag    240 ggacccccca ggcttcacca gctctccccc agactccacc agctgcactt c            291
```

<210> SEQ ID NO 66
<211> LENGTH: 294
<212> TYPE: DNA
<213> ORGANISM: Canis familiaris

<400> SEQUENCE: 66

```
cttcggacag taatacacgg ctgtgtcctc ggatctcagg ctgttcatct gcagatacag    60
tgtgttcctg gcattgtctc tggagatggt gaaccggccc ttcacagcat ctgcgtagta   120
tgtgctactt ccaccactgt taatgtatgc gacccactgc agccccttcc ctggagcctg   180
gcggacccag ctcatggcat agctactgaa ggtgaatcca gaggccacac aggacagtct   240
cagggatccc ccaggcttca ccaggtctcc cccagactcc accagctgta cctc          294
```

<210> SEQ ID NO 67
<211> LENGTH: 294
<212> TYPE: DNA
<213> ORGANISM: Canis familiaris

<400> SEQUENCE: 67

```
ccttgcacag taatatacag ccgtgtcctc ggctctcagg ctgtgcatcc gtagatacag    60
cgtgttcttg gcgttgtctc tggagatggt gaatcggccc ttcacagcgt ctgcgtagct   120
tgtgctattt ccactactgc taatttctgc aacacactgt agccccttcc ctggagcctg   180
gcagaaccag ctcatgtaga agctactgaa ggtgaatcca gaggccacac aggagagtct   240
cagggaccgc tcaggcttca caaggtctcc tccagactcc accagctgca cctc          294
```

<210> SEQ ID NO 68
<211> LENGTH: 294
<212> TYPE: DNA
<213> ORGANISM: Canis familiaris

<400> SEQUENCE: 68

```
ccttgcacag ttatacaggg ccgtatcctc agctctcagg ctgttcatct gcagatacag    60
cgtgttcttg gcattgtctc tggaaatggt gaatcggccc ttcacagcgt ctgcgtatta   120
tgtgctactt ccatcactgc taatgtatcc gacccactgc agccccttcc taggagcctg   180
gcggacccag ctcatggcat agctactgaa ggtgaatcca gaggccacac aggacagtct   240
cagggaatcc ccaggcttca ccaggtctcc gccagactcc accagctgca cctc          294
```

<210> SEQ ID NO 69
<211> LENGTH: 294
<212> TYPE: DNA
<213> ORGANISM: Canis familiaris

<400> SEQUENCE: 69

```
gtctgcacag taatacaggg ccgtgtgctc agctctcagg ctgttcatct gaagatacag    60
cgtgttcttg gcgttgtctc tggagatggt gaatcggccc tgcacagcgt ctttgtaacc   120
tgtgctactt ccatcatagc taatatatgc aatacactgc agccctttcc tggagtctaa   180
```

```
tggaccgagc tcatgtcata gttactgaag gtgaatccag gggccacaca ggagagtctc      240 agggacccccc caggcttcac caggtctccc ccagactcca tcagctgcac ctca           294

<210> SEQ ID NO 70
<211> LENGTH: 294
<212> TYPE: DNA
<213> ORGANISM: Canis familiaris

<400> SEQUENCE: 70
ccctcgcaca gtaatacaca gcggtgtcct cggctctcag gctgttcaac tgcagataca      60
gcatgttctt ggcgttgtct ctggagaggt gaatcggccc ttcacagcat ctgtgtacct      120
tgtgctactt ccaccactgt taatgtatgc gacccactgc agccacttcc ctggagcctg     180
gcggacccag ctcatgatgt agctactgaa ggtgaatcca gaagccacac aggagagtct     240
caggagccca caaggcttca ccaagtctcc cccagactcc accagctgca cctc            294

<210> SEQ ID NO 71
<211> LENGTH: 294
<212> TYPE: DNA
<213> ORGANISM: Canis familiaris

<400> SEQUENCE: 71
gtctgcacag taatacacgg ccgtgtcctc ggctctcagg ctgttcatct gcagatacac      60
tgtgttcttg gcgttgtctc tggagatggt gaatcggccc ttcacagcgt ctacatggta     120
tgtgctactt ccactactgc taatagctgc aacccactgc agccccttcc ctggagcctg     180
gcagacccaa ctcatggcat agctactgaa ggtgaatcca gaggcacac aggagagtct      240 cagggacccc cctggcttca ccagatctcc cccaagctcc accagctgca attc            294

<210> SEQ ID NO 72
<211> LENGTH: 294
<212> TYPE: DNA
<213> ORGANISM: Canis familiaris

<400> SEQUENCE: 72
gtgtgcacag taatacacag tcgtgcccctc agctctcagg ctgttcatct gcagatacag     60
cgtgttcttg gcattgtctc tggagatggt gaatcggccc ttcacagcat ctgcgtggta     120
tgtggtactt ccatctttgt taattactga gacccagtgc agcccttttcc ctggagcttg    180 gcggacccag cttatccagt aactactgaa agtgaatcca gaggctacac aggagaatct    240
cagggacccc tcaggcttca ccagctctcc cccagattcc accagtggca cctc           294

<210> SEQ ID NO 73
<211> LENGTH: 294
<212> TYPE: DNA
<213> ORGANISM: Canis familiaris

<400> SEQUENCE: 73
ccttgcacag gaatacatgg ccgtgttctc agctctcagg ctgttcatct gcagaaacac      60
tgtgttcttg gcgttgtctc tggagatggt gaatcggccc ttcacagcat ctgtgtagct     120
tgtgctactt ccactagcat aaatctatgt gacccactgc accccttcc cgggagcctg     180 gcggacccag ctcatgctgt agctactaaa ggtgaatcca gcggccacac aggagagtct   240
cagggacccc tccggcttca caaggtctcc cccagactcc accagctgca cctc            294

<210> SEQ ID NO 74
<211> LENGTH: 294
```

```
<212> TYPE: DNA
<213> ORGANISM: Canis familiaris

<400> SEQUENCE: 74
ctttgcacag taatacacgg ccgtgtcctc ggctcccagg ctgttcatct gcagatacag    60
cgtgttcttg gcattgtctc tggagatggt gaattgaccc ttcacagcgt ctgggtagta   120
tgtgctactt ccatcactgc taatctgtgc gacccactgc agccccttcc ctggagcctg   180
gcggacccat tccatgtagt agctactgaa ggtgaatcca gaggccacac aagagagtct   240
cagggatccc ccaggcttca ccagatctcc cccagactcc accagctgca cctc          294

<210> SEQ ID NO 75
<211> LENGTH: 294
<212> TYPE: DNA
<213> ORGANISM: Canis familiaris

<400> SEQUENCE: 75
catcgcacag taatacacag cagagtcctc ggctctcagg ctgttcatct gcagatagag    60
cgtgttcttg gcgttgtctc tggagatggt gaatcggccc ttcacagcct gtgggtagta   120
tgtgctactt ccatcactgc taatccctgc gacccactgc agcctcttcc ctggagcctg   180
gcggacccag tccatgtagt agctactgaa ggtgaatcca gaggccacac aagagagtct   240
cagggacccc ccaggcttca ccaggtttcc tccagactcc accagctgca cctc          294

<210> SEQ ID NO 76
<211> LENGTH: 294
<212> TYPE: DNA
<213> ORGANISM: Canis familiaris

<400> SEQUENCE: 76
ccttgcacag taatataggg ccatgtcctc ggctctctgg ctgttcatct gcagatacag    60
cgtattcttg gaattgtctc tggagatggt aaattggccc ttcatggcgt ctgcgtacct   120
tgtgctactt ccatcattgc taatccttgt gacccactgc agccccttcc ctgtagcctg   180
gcggacccag tgcatgtagt agctactgaa ggtgaatcca gaggccacac aagagagtct   240
cagggacccc ccagacttca ccaggtctcc tccagactcc accagctgca cctc          294

<210> SEQ ID NO 77
<211> LENGTH: 294
<212> TYPE: DNA
<213> ORGANISM: Canis familiaris

<400> SEQUENCE: 77
cttcgcacag taatgcatgg ccctgtcctc agctctcagg ctgttcatct gcagatagag    60
cgtgttcttg gcgttttctc tggagatggt gaatcggccc ttcactgtgt ctgcgtagta   120
tatgctacct ccaccactgt taataattgc gacccactcc agccctttcc ctggagcctg   180
gaggacccag tgcatccagt agctactgaa ggtgaatcca gaggacacac aagaaagtct   240
cagagacccc ccaggcttca ccaggtctcc cccagactct accagctgca actc          294

<210> SEQ ID NO 78
<211> LENGTH: 31
<212> TYPE: DNA
<213> ORGANISM: Canis familiaris

<400> SEQUENCE: 78
gtactactgt actgatgatt actgtttcaa c                                    31
```

```
<210> SEQ ID NO 79
<211> LENGTH: 19
<212> TYPE: DNA
<213> ORGANISM: Canis familiaris

<400> SEQUENCE: 79
ctactacggt agctactac                                                    19

<210> SEQ ID NO 80
<211> LENGTH: 17
<212> TYPE: DNA
<213> ORGANISM: Canis familiaris

<400> SEQUENCE: 80
tatatatata tggatac                                                      17

<210> SEQ ID NO 81
<211> LENGTH: 19
<212> TYPE: DNA
<213> ORGANISM: Canis familiaris

<400> SEQUENCE: 81
gtatagtagc agctggtac                                                    19

<210> SEQ ID NO 82
<211> LENGTH: 19
<212> TYPE: DNA
<213> ORGANISM: Canis familiaris

<400> SEQUENCE: 82
agttctagta gttggggct                                                    19

<210> SEQ ID NO 83
<211> LENGTH: 11
<212> TYPE: DNA
<213> ORGANISM: Canis familiaris

<400> SEQUENCE: 83
ctaactgggg c                                                            11

<210> SEQ ID NO 84
<211> LENGTH: 45
<212> TYPE: DNA
<213> ORGANISM: Canis familiaris

<400> SEQUENCE: 84
tgaggagacg gtgaccaggg tgccctggcc ccagaggtct aagta                       45

<210> SEQ ID NO 85
<211> LENGTH: 42
<212> TYPE: DNA
<213> ORGANISM: Canis familiaris

<400> SEQUENCE: 85
tgaggagaca gtgaccaggg tgccctggcc ccagtaacca aa                          42

<210> SEQ ID NO 86
<211> LENGTH: 42
<212> TYPE: DNA
<213> ORGANISM: Canis familiaris

<400> SEQUENCE: 86
tgaggagacg gtgaccaggg ttccctggcc ccagtagtca aa                          42
```

<210> SEQ ID NO 87
<211> LENGTH: 38
<212> TYPE: DNA
<213> ORGANISM: Canis familiaris

<400> SEQUENCE: 87
tgaggacaca gtgaccaggg tcccttggcc ccagtagt                        38

<210> SEQ ID NO 88
<211> LENGTH: 53
<212> TYPE: DNA
<213> ORGANISM: Canis familiaris

<400> SEQUENCE: 88
tgaggacacg aagagtgagg tgccatggcc ccagtagtcc ataccatagt aat       53

<210> SEQ ID NO 89
<211> LENGTH: 282
<212> TYPE: DNA
<213> ORGANISM: Canis familiaris

<400> SEQUENCE: 89
gacatcacga tgactcagtg tccaggctcc ctggctgtgt ctccaggtca gcaggtcacc    60
acgaactgca gggccagtca aagcgttagt ggctacttag cctggtacct gcagaaacca   120
ggacagcgtc ctaagctgct catctactta gcctccagct gggcatctgg ggtccctgcc   180
cgattcagca gcagtggatc tgggacagat ttcaccctca ccgtcaacaa cctcgaggct   240
gaagatgtga gggattatta ctgtcagcag cattatagtt ct                     282

<210> SEQ ID NO 90
<211> LENGTH: 297
<212> TYPE: DNA
<213> ORGANISM: Canis familiaris

<400> SEQUENCE: 90
gatattgtca tgacacaggc cccaccgtcc ctgtccgtca gccctggaga gccggcctcc    60
atctcctgca aggccagtca gagcctcctg cacagtaatg gaacaccta tttgtattgg   120 ttccgacaga agccaggcca gtctccagag ggcctgatct ataaggtgtc caaccgcttc   180
actggcgtgt cagacaggtt cagtggcagc gggtcaggga cagatttcac cctgagaatc   240
agcagagtgg aggctgacga tgctggagtt tattactgcg ggcaaaattt acagttt     297

<210> SEQ ID NO 91
<211> LENGTH: 294
<212> TYPE: DNA
<213> ORGANISM: Canis familiaris

<400> SEQUENCE: 91
attgtcatga cacagacgcc accgtccctg tctgtcagcc tagagagac ggcctccatc     60 tcctgcaagg ccagtcagag cctcctgcac agtgatggaa acacctattt ggattggtac   120
ctgcaaaagc caggccagtc tccacagctt ctgatctact ggtttccaa ccgcttcact    180 ggcgtgtcag acaggttcag tggcagcggg tcagggacag atttcaccct gagaatcagc   240
agagtggagg ctaacgatac tggagtttat tactgcgggc aaggtacaca gctt         294

<210> SEQ ID NO 92
<211> LENGTH: 293
<212> TYPE: DNA

<213> ORGANISM: Canis familiaris

<400> SEQUENCE: 92

| gatattgtca tgacacagac cccactgtcc ctgtccgtca gccctggaga gccggcctcc | 60 |
| atctcctgca aggccagtca gagcctcctg cacagtaatg ggaacaccta tttgtattgg | 120 |
| ttccgacaga agccaggcca gtctccacag cgtttgatct ataaggtctc caacagagac | 180 |
| cctggggtcc cagacaggtt cagtggcagc gggtcaggga cagatttcac cctgagaatc | 240 |
| agcagagtgg aggctgatga tgctggagtt tattactgcg ggcaaggtat aca | 293 |

<210> SEQ ID NO 93
<211> LENGTH: 293
<212> TYPE: DNA
<213> ORGANISM: Canis familiaris

<400> SEQUENCE: 93

| gatattgtca tgacacagac cccactgtcc ctgtctgtca gccctggaga gactgcctcc | 60 |
| atctcctgca aggccagtca gagcctcctg cacagtgatg gaaacacgta tttgaactgg | 120 |
| ttccgacaga agccaggcca gtctccacag cgtttaatct ataaggtctc caacagagac | 180 |
| cctggggtcc cagacaggtt cagtggcagc gggtcaggga cagatttcac cctgagaatc | 240 |
| agcagagtgg aggctgacga tactggagtt tattactgcg ggcaaggtat aca | 293 |

<210> SEQ ID NO 94
<211> LENGTH: 293
<212> TYPE: DNA
<213> ORGANISM: Canis familiaris

<400> SEQUENCE: 94

| gatattgtca tgacacagaa cccactgtcc ctgtccgtca gccctggaga gacggcctcc | 60 |
| atctcctgca aggccagtca gagcctcctg cacagtaacg ggaacaccta tttgaattgg | 120 |
| ttccgacaga agccaggcca gtctccacag ggcctgatct ataaggtctc caacagagac | 180 |
| cctggggtcc cagacaggtt cagtggcagc gggtcaggga cagatttcac cctgagaatc | 240 |
| agcagagtgg aggctgacga tgctggagtt tattactgca tgcaaggtat aca | 293 |

<210> SEQ ID NO 95
<211> LENGTH: 290
<212> TYPE: DNA
<213> ORGANISM: Canis familiaris

<400> SEQUENCE: 95

| attgtcatga cacagacccc accgtccctg tccgtcagcc ctggagagcc ggcctccatc | 60 |
| tcctgcaagg ccagtcagag cctcctgcac agtaacggga cacctatttt gaattggttc | 120 |
| cgacagaagc caggccagtc tccacagggc ctgatctata gggtgtccaa ccgctccact | 180 |
| ggcgtgtcag acaggttcag tggcagcggg tcagggacag atttcaccct gagaatcagc | 240 |
| agagtggagg ctgacgatgc tggagtttat tactgcgggc aaggtataca | 290 |

<210> SEQ ID NO 96
<211> LENGTH: 293
<212> TYPE: DNA
<213> ORGANISM: Canis familiaris

<400> SEQUENCE: 96

| gatattgtca tgacacagac cccactgtcc ctgtctgtca gccctggaga gactgcctcc | 60 |
| atctcttgca aggccagtca gagcctcctg cacagtgatg gaaacacgta tttgaattgg | 120 |

```
ttccgacaga agccaggcca gtctccacag cgtttgatct ataaggtctc caacagagac      180
cctggggtcc cagacaggtt cagtggcagc gggtcaggga cagatttcac cctgagaatc      240
agcagagtgg aggctgacga tactggagtt tattactgcg ggcaagttat aca             293
```

<210> SEQ ID NO 97
<211> LENGTH: 294
<212> TYPE: DNA
<213> ORGANISM: Canis familiaris

<400> SEQUENCE: 97

```
attgtcatga cacagacccc actgtccctg tccgtcagcc ctggagagac tgcctccatc       60
tcctgcaagg ccagtcagag cctcctgcac agtgatggaa acacgtattt gaattggttc      120
cgacagaagc caggccagtc tccacagcgt ttgatctata aggtctccaa cagagaccct      180
ggggtcccag acaggttcag tggcagcggg tcagggacag atttcaccct gagaatcagc      240
agagtggagg ctgacgatac tggagtttat tactgcatgc aaggtacaca gttt            294
```

<210> SEQ ID NO 98
<211> LENGTH: 289
<212> TYPE: DNA
<213> ORGANISM: Canis familiaris

<400> SEQUENCE: 98

```
tcgtcatgac acagacccca ctgtccctgt ccgtcagccc tggagagact gcctccatct       60
cctgcaaggc cagtcagagc ctcctgcaca gtaacgggaa cacctatttg ttttggttcc      120
gacagaagcc aggccagtct ccacagcgcc tgatcaactt ggtttccaac agagaccctg      180
gggtcccaca caggttcagt ggcagcgggt cagggacaga tttcaccctg agaatcagca      240
gagtggaggc tgacgatgct ggagtttatt actgcgggca aggtataca                  289
```

<210> SEQ ID NO 99
<211> LENGTH: 297
<212> TYPE: DNA
<213> ORGANISM: Canis familiaris

<400> SEQUENCE: 99

```
gatattgtca tgacacaggc cccaccgtct ctgtccgtca gccctagaga gccggcctcc       60
atctcctgca aggccagtca gagcctcctg cacagtaatg ggaacaccta tttgtattgg      120
ttccgacaga agccaggcca gtctccagag ggcctgatct ataaggtgtc caaccgcttc      180
actggcgtgt cagacaggtt cagtggcagc gggtcaggga cagatttcac cctgagaatc      240
agcagagtgg aggctgacga tgctggagtt tattactgcg ggcaaggtat acagttt         297
```

<210> SEQ ID NO 100
<211> LENGTH: 297
<212> TYPE: DNA
<213> ORGANISM: Canis familiaris

<400> SEQUENCE: 100

```
gatatcgtca tgacacagac cccactgtcc ctgtccgtca gccctggaga gccggcctcc       60
atctcctgca aggccagtca gagcctcctg cacagtaacg ggaacaccta tttgttttgg      120
tttcgacaga agccaggcca gtctccacag cgtttgatct ataaggtctc caacagagac      180
actggggtcc cagacaggtt cagtggcagc gggtcaggga cagatttcac cctgagaatc      240
agcacagtgg aggctgacga tactggagtt tattactgcg ggcaaggtac acagttt         297
```

<210> SEQ ID NO 101
<211> LENGTH: 293
<212> TYPE: DNA
<213> ORGANISM: Canis familiaris

<400> SEQUENCE: 101

```
gatattgtca tgacacagac cccactgtcc ctgtctgtca gccctggaga gactgcctcc      60
atctcctgca aggccagtca gagcctcctg cacagtgatg gaaacacgta tttgaattgg     120
ttccgacaga agccaggcca gtctccacag cgtttgatct ataaggtctc caacagagac     180
actggggtcc cagacaggtt cagtggcagc gggtcaggga cagatttcac cctgagaatc     240
agcagagtgg aggctgacga tactggagtt tattactgtg ggcaagttat aca            293
```

<210> SEQ ID NO 102
<211> LENGTH: 297
<212> TYPE: DNA
<213> ORGANISM: Canis familiaris

<400> SEQUENCE: 102

```
gatattgtca tgacacagac cccactgtcc ctgtccgtca gccctggaga gactgcctcc      60
atctcctgca aggccagtca gagcctcctg cacagtgatg gaaacacgta tttgaattgg     120
ttccgacaga agccaggcca gtctccacag cgtttgatct ataaggtctc caacagagac     180
actggggtcc cagacaggtt cagtggcagc gggtcaggga cagatttcac cctgagaatc     240
agcacagtgg aggctgacga tactggagtt tattactgcg ggcaaggtac acagttt       297
```

<210> SEQ ID NO 103
<211> LENGTH: 293
<212> TYPE: DNA
<213> ORGANISM: Canis familiaris

<400> SEQUENCE: 103

```
gatattgtca tgacacagaa cccactgtcc ctgtctgtca gccctggaga gacggcctcc      60
atctcctgca aggccagtca gagcctcctg cacagtgatg gaaacacgta tttgaactgg     120
ttccgacaga agccaggcca gtctccacag cgtttaatct ataaggtctc caacagagac     180
cctggggtcc cagacaggtt cagtggcagc gggtcaggga cagatttcac cctgagaatc     240
agcagagtgg aggctgacga tactggagtt tattactgcg ggcaaggtat aca            293
```

<210> SEQ ID NO 104
<211> LENGTH: 293
<212> TYPE: DNA
<213> ORGANISM: Canis familiaris

<400> SEQUENCE: 104

```
gatattgtca tgacacagac cccactgtcc ctgtccgtca gccctggaga gccggcctcc      60
atctcctgca aggccagtca gagcctcctg cacagtaatg ggaacaccta tttgtattgg     120
ttccaacaga agccaggcca gtctccacag cgtttgatct ataaggtctc caacagagac     180
cctggggtcc cagacaggtt cagtggcagc gggtcaggga cagatttcac cctgagaatc     240
agcagagtgg aggctgatga tgctggagtt tattactgcg ggcaaggtat aca            293
```

<210> SEQ ID NO 105
<211> LENGTH: 293
<212> TYPE: DNA
<213> ORGANISM: Canis familiaris

<400> SEQUENCE: 105

```
gatattgtca tgacacagac cccactgtcc ctgtccgtca gccctggaga gacggcctcc    60
atctcctgca aggccagtca gagcctcctg cacagtaacg ggaacaccta tttgaattgg   120
ttccgacaga agccaggcca gtctccacag ggcctgatct ataaggtctc caacagagac   180
cctggggtcc cagacaggtt cagtggcagc gggtcaggga cagatttcac cctgagaatc   240
agcagagtgg aggctgacga tgctggagtt tattactgca tgcaaggtat aca           293
```

<210> SEQ ID NO 106
<211> LENGTH: 293
<212> TYPE: DNA
<213> ORGANISM: Canis familiaris

<400> SEQUENCE: 106

```
gatatcgtca tgacacagac cccactgtcc ctgtccgtca gccctggaga gccggcctcc    60
atctcctgca aggccagtca gagcctcctg cacagtaatg ggaacaccta tttgtattgg   120
ttccgacaga agccaggcca gtctccagag ggcctgatct ataaggtgtc caaccgcttc   180
actggcgtgt cagacaggtt cagtggcagc gggtcaggga cagatttcac cctgagaatc   240
agcagagtgg aggctgacga tgctggagtt tattactgcg gcaaggtat aca            293
```

<210> SEQ ID NO 107
<211> LENGTH: 275
<212> TYPE: DNA
<213> ORGANISM: Canis familiaris

<400> SEQUENCE: 107

```
tcttgaccta gtctccagcc tccctggcta tttcccaagg ggacagagtc aaccatcacc    60
tatgggacca gcaccagtaa aagctccagc aacttaacct ggtaccaaca gaactctgga   120
gcttcttcta agctccttgt ttacagcaca gcaagcctgg cttctgggat cccagctggc   180
ttcattggca gtggatgtgg gaactcttcc tctctcacaa tcaatggcat ggaggctgaa   240
ggtgctgcct actattacta ccagcagtag ggtag                               275
```

<210> SEQ ID NO 108
<211> LENGTH: 38
<212> TYPE: DNA
<213> ORGANISM: Canis familiaris

<400> SEQUENCE: 108

```
gtggacgttc ggagcaggaa ccaaggtgga gctcaaac                             38
```

<210> SEQ ID NO 109
<211> LENGTH: 38
<212> TYPE: DNA
<213> ORGANISM: Canis familiaris

<400> SEQUENCE: 109

```
ttatactttc agccagggaa ccaagctgga gataaaac                             38
```

<210> SEQ ID NO 110
<211> LENGTH: 38
<212> TYPE: DNA
<213> ORGANISM: Canis familiaris

<400> SEQUENCE: 110

```
gttcactttt ggccaaggga ccaaactgga gatcaaac                             38
```

<210> SEQ ID NO 111

```
<211> LENGTH: 38
<212> TYPE: DNA
<213> ORGANISM: Canis familiaris

<400> SEQUENCE: 111
gcttacgttc ggccaaggga ccaaggtgga gatcaaac                              38

<210> SEQ ID NO 112
<211> LENGTH: 38
<212> TYPE: DNA
<213> ORGANISM: Canis familiaris

<400> SEQUENCE: 112
gatcaccttt ggcaaaggga cacatctgga gattaaac                              38

<210> SEQ ID NO 113
<211> LENGTH: 440
<212> TYPE: DNA
<213> ORGANISM: Canis familiaris

<400> SEQUENCE: 113
tcctcttgtc taaagaaaag aacatcactc tctctgtgtc tctcccctt tcagggtcct       60 gggaccagtc tgtgctgact cagccgccct cagtgtcggg atctgtgggc cagagaatca    120
ccatctcctg ctctggaagc acaaacagct accaacagct ctcaggaaag gcctctaaac    180
tcctcgtaga tggtactggg aaccgaccct caggggtccc cgaccgattt tctggctcca    240
aatctggcaa ctcaggcact ctgaccatca ctgggcttgg gacgaggctg aggacgaggc    300
tgaggacgag gctgattatt attgttagtc cactgatctc acgcttggtg ctcccacagt    360
gctctgggcc tacggggaag tgagacacaa acctgctgtc cctagaacaa tggcactgcc    420
tgtgcaaccc tggccttagg                                                440

<210> SEQ ID NO 114
<211> LENGTH: 435
<212> TYPE: DNA
<213> ORGANISM: Canis familiaris

<400> SEQUENCE: 114
cagtctgtac tgactcagcc ggcctcagtg tctgggtccc tgggccagag ggtcaccatc      60
tcctgcactg gaagcagctc caacatcggt ggatattatg tgagctggct ctagcagctc    120
ccgggaacag gccccagaac catcatctat agtagtagta accgaccttc aggggtccct    180
gatcgattct ctggctccag gtcaggcagc acagccaccc tgaccatctc tgggctccag    240
gctgaggatg aggctgatta ttactgttca acatacgaca gcagtctcaa agctcccaca    300
gtgctccagg cctgtgggga agtgagacaa aaacccattt acctatctgc aatgtgagtg    360
agcgccccag gagcttcctg cgtaggctcc cctgggtttc tgctgattct tcagttgatg    420
ccctgagccc aggtg                                                     435

<210> SEQ ID NO 115
<211> LENGTH: 298
<212> TYPE: DNA
<213> ORGANISM: Canis familiaris

<400> SEQUENCE: 115
atcccaggct gtggtgaccc agcttccttc tctgcatccc tgggaacaac agccagactc       60
acatgcaccc tgagctgtgg cttcagtatt gatagatatg ctataaactg gttccagcag     120
aaggcagaga gccttcccctg gtacctactg tgctattact ggtactcaag tacacagttg    180
```

```
ggcttcagcg tccccagctg catctctgga tccaagacaa ggccacattc acaaacgagt    240
agacccatct ctggttgggt ctagagctcc agccccacct gagactgatg cacaattg     298
```

<210> SEQ ID NO 116
<211> LENGTH: 290
<212> TYPE: DNA
<213> ORGANISM: Canis familiaris

<400> SEQUENCE: 116

```
ggcccaggct gtgctgactc agctgccctc agtgtctgca gccctgggac agagggtcac    60
catctgcact ggaagcagca ccaacatcgg cagtggttat tatacactat ggtaccagca   120
gctgcaggaa agtcccctaa aactatcatc tatggtaata gcaatcgacc cttgagggtc   180
ccggatcgat tctctggctc caagtatggc aattcagcca cgctgaccat cactgggctc   240
caggctgagg acgaggatga ttattactgc cagtcctctg atgacaacct              290
```

<210> SEQ ID NO 117
<211> LENGTH: 324
<212> TYPE: DNA
<213> ORGANISM: Canis familiaris

<400> SEQUENCE: 117

```
cagtctgtgc tgactcagcc ggcctcggtg tctgggtccc tgggccagag ggtcaccatc    60
tcctgcactg gaagcagctc caatgttggt tatggcaatt atgtgggctg gtaccagcag   120
cttccaggaa caggccccag aaccattatc tgttatacca atactcgacc ctctggggtt   180
cctgatcgat actctggctc caagtcaggc agcacagcca ccctgaccat ctctgggctc   240
caggctgaag acgagactga ttattactgt actacgtgtg acagcagtct caatgctagc   300
acagtgctcc aggcctttgg agag                                          324
```

<210> SEQ ID NO 118
<211> LENGTH: 233
<212> TYPE: DNA
<213> ORGANISM: Canis familiaris

<400> SEQUENCE: 118

```
gtgatggtga gggcgacttt gttcccagag atggatccag agaagcgatc agggacccca    60
gaagggtgtc tgcttgtgct gtagataagc atgcaaggag cctggccttg gtctgctgg    120 taccagctgg ggtagtttct tgtagagact tacccagagc tgaggccaca tgtgaatgtg   180
actgtccctc ctggagacac tgagagtgac ggatcctggg tgaccacagt ctg          233
```

<210> SEQ ID NO 119
<211> LENGTH: 291
<212> TYPE: DNA
<213> ORGANISM: Canis familiaris

<400> SEQUENCE: 119

```
cagactgtgg taacccagga gccatcactc tcagtgtctc caggagggac agtcacactc    60
acatgtggcc tcagctctgg gtcagtctct acaagtaatt accctggctg gtaccagcag   120
acccaaggcc gggctcctcg cacgattatc tacaacacaa gcagccgccc ctctggggtc   180
cctaatcgct tctctggatc catctctgga aacaaagccg ccctcaccat cacaggagcc   240
cagcccgagg atgaggctga ctattactgt tccttgtata cgggtagtta c             291
```

<210> SEQ ID NO 120

```
<211> LENGTH: 288
<212> TYPE: DNA
<213> ORGANISM: Canis familiaris

<400> SEQUENCE: 120
cagtctgtgc tgactcagcc tccctcagtg tccgggttcc tgggccagag ggtcaccatc    60
tcctgcactg gaagcagctc caacatcggt agaggttatg tgcactggta ccaacagctc   120
ccaggaacag gccccagaac cctcatctat ggtattagta accgacctc agggtcccc     180 gatcgattct ctggctccag gtcaggcagc acagccactc tgacaatctc tgggctccag   240
gctgaggatg aggctgatta ttactgctca tcctgggaca gcagtctc               288

<210> SEQ ID NO 121
<211> LENGTH: 299
<212> TYPE: DNA
<213> ORGANISM: Canis familiaris

<400> SEQUENCE: 121
cagcctgtga tgacccagct gtcctccctc tctgcatccc tggaaacaac aaccagacac    60
acctgcaccc tgagcagtgg cttcagaaat aacagctgtg taataagttg attccagcag   120
aagtcaggga gccctccctg gtgtctcctg tactattact cagactcaag tatacatttg   180
ggctctgagg ttcccagctg cttctctgga tccaagacaa ggccacaccc acactgagta   240
gacccatccc tgggtgggtc tagagctcca gccccactgg aggctgatgc acaattgca    299

<210> SEQ ID NO 122
<211> LENGTH: 282
<212> TYPE: DNA
<213> ORGANISM: Canis familiaris

<400> SEQUENCE: 122
ctgactcaaa cggcctccat gtctgggtct ctgggccaga gggtcaccgt ctcctgcact    60
ggaagcagtt ccaacgttgg ttatagaagt tatgtgggct ggtaccagca gctcccagga   120
acaggcccca gaaccatcat ctataatacc aatactcgac cctctggggt tcctgatcga   180
ttctctggct ccatatcagg cagcacagcc accctgacta ttgctggact ccaggctgag   240
gacgaggctg attattactg ctcatcctat gacagcagtc tc                     282

<210> SEQ ID NO 123
<211> LENGTH: 271
<212> TYPE: DNA
<213> ORGANISM: Canis familiaris

<400> SEQUENCE: 123
cagtctgtgc tgaatcagct gccttcagtg ttaggatccc tgggccagag aatcaccatc    60
tcctgctctg aagcacgaa tgacatcggt atgcttggtg tgaactggta ccaagagccg   120
ccaggaaagg cccctaaact cctcgtagat ggtactggga atcgaccctc agggtccctg   180
ccgattttct ggctccaaat ctggcaactc aggcactctg accatcactg ggctccaggc   240
tgaggacgag gctgattatt attgtcagtc c                                 271

<210> SEQ ID NO 124
<211> LENGTH: 284
<212> TYPE: DNA
<213> ORGANISM: Canis familiaris

<400> SEQUENCE: 124
ctgctgtccc aggatgagca gtaataatca gcctcatcct cagcctggaa cccagagatt    60
```

| | |
|---|---|
| gtcagagtgt ctgtgctgcc tgacctggag ccagagaatt gattggggac ccctgagggt | 120 |
| tggttactac taccatatat gagggttctt gggcgtgttc ccaggagctg ttggtaccag | 180 |
| atcacataac ctctaccgac gttggagctg cttccagtgc aggatatagt gaccctctgg | 240 |
| cccagggacc tgaacactga gggaggctga gtcagcacag actg | 284 |

<210> SEQ ID NO 125
<211> LENGTH: 364
<212> TYPE: DNA
<213> ORGANISM: Canis familiaris

<400> SEQUENCE: 125

| | |
|---|---|
| cagtctgtgc tgactcaacc agtctcagtg tctggggccc tgtgccagag ggtcaccatc | 60 |
| tcctgcactg gaaacagctc caacattggt tatagcagtt gtgtgagctg atatcagcag | 120 |
| ctcccaggaa caggccccag aaccatcatc tatagtatga atactcaacc ctctggggtt | 180 |
| cctgatcgat tctctggctc caggtcaggc aactcagcca ccctaaccat ctctgggctc | 240 |
| caggctgagg acaaggctga ctattactgc tcaacatatg acagcagtct cagtgctcac | 300 |
| acggtgctcc aggcctgtgg ggaattgaga caaaaaccta cttatctgtc tgcagtgagc | 360 |
| ggag | 364 |

<210> SEQ ID NO 126
<211> LENGTH: 37
<212> TYPE: DNA
<213> ORGANISM: Canis familiaris

<400> SEQUENCE: 126

| | |
|---|---|
| agtgtgttcg gcggaggcac ccatctgacc gtcctcg | 37 |

<210> SEQ ID NO 127
<211> LENGTH: 37
<212> TYPE: DNA
<213> ORGANISM: Canis familiaris

<400> SEQUENCE: 127

| | |
|---|---|
| tacgtgttcg gctcaggaac ccaactgacc gtccttg | 37 |

<210> SEQ ID NO 128
<211> LENGTH: 38
<212> TYPE: DNA
<213> ORGANISM: Canis familiaris

<400> SEQUENCE: 128

| | |
|---|---|
| tattgtgttc ggcggaggca cccatctgac cgtcctcg | 38 |

<210> SEQ ID NO 129
<211> LENGTH: 38
<212> TYPE: DNA
<213> ORGANISM: Canis familiaris

<400> SEQUENCE: 129

| | |
|---|---|
| tggtgtgttc ggcggaggca cccacctgac cgtcctcg | 38 |

<210> SEQ ID NO 130
<211> LENGTH: 38
<212> TYPE: DNA
<213> ORGANISM: Canis familiaris

<400> SEQUENCE: 130

```
tgctgtgttc ggcggaggca cccacctgac cgtcctcg                    38

<210> SEQ ID NO 131
<211> LENGTH: 100
<212> TYPE: DNA
<213> ORGANISM: Canis familiaris

<400> SEQUENCE: 131
atttctgtac ctgatctatg tcaatatctg taccatggct ctagcagaga tgaaatatga    60
gacagtctga tgtcatgtgg ccatgcctgg tccagacttg                         100

<210> SEQ ID NO 132
<211> LENGTH: 100
<212> TYPE: DNA
<213> ORGANISM: Canis familiaris

<400> SEQUENCE: 132
gtcaatcagc agaaatccat catacatgag acaaagttat aatcaagaaa tgttgcccat    60
aggaaacaga ggatatctct agcactcaga gactgagcac                        100
```